United States Patent
Peters

(10) Patent No.: US 9,539,245 B2
(45) Date of Patent: Jan. 10, 2017

(54) COMBINATION OF IMMUNOTHERAPIES WITH ACTIVATORS OF TIE-2

(71) Applicant: Aerpio Therapeutics, Inc., Cincinnati, OH (US)

(72) Inventor: Kevin Peters, Cincinnati, OH (US)

(73) Assignee: AERPIO THERAPEUTICS, INC., Cincinnati, OH (US)

( * ) Notice: Subject to any disclaimer, the term of this patent is extended or adjusted under 35 U.S.C. 154(b) by 0 days.

(21) Appl. No.: 14/819,871

(22) Filed: Aug. 6, 2015

(65) Prior Publication Data

US 2016/0038467 A1 Feb. 11, 2016

Related U.S. Application Data

(60) Provisional application No. 62/034,695, filed on Aug. 7, 2014.

(51) Int. Cl.
| | | |
|---|---|---|
| *A61K 39/00* | (2006.01) | |
| *C07D 277/30* | (2006.01) | |
| *A61K 31/427* | (2006.01) | |
| *A61K 38/45* | (2006.01) | |
| *A61K 39/395* | (2006.01) | |
| *A61K 31/00* | (2006.01) | |

(52) U.S. Cl.
CPC .............. *A61K 31/427* (2013.01); *A61K 31/00* (2013.01); *A61K 38/45* (2013.01); *A61K 39/395* (2013.01); *A61K 39/3955* (2013.01); *A61K 2039/505* (2013.01); *C07K 2319/55* (2013.01)

(58) Field of Classification Search
CPC .............. A61K 31/427; A61K 39/3955; A61K 2039/505; A61K 31/00; A61K 38/45; A61K 39/395; C07K 2319/55
USPC .............. 514/444; 424/134.1, 142.1; 548/204
See application file for complete search history.

(56) References Cited

U.S. PATENT DOCUMENTS

| | | | |
|---|---|---|---|
| 6,930,117 B2 | 8/2005 | Warshakoon et al. |
| 6,946,479 B2 | 9/2005 | Warshakoon et al. |
| 7,226,755 B1 | 6/2007 | Peters et al. |
| 7,247,632 B2 | 7/2007 | Warshakoon et al. |
| 7,247,648 B2 | 7/2007 | Warshakoon et al. |
| 7,507,568 B2 | 3/2009 | Evdokimov et al. |
| 7,589,212 B2 | 9/2009 | Gray et al. |
| 7,622,593 B2 | 11/2009 | Gray et al. |
| 7,632,862 B2 | 12/2009 | Peters et al. |
| 7,769,575 B2 | 8/2010 | Evdokimov et al. |
| 7,790,748 B2 | 9/2010 | Warshakoon et al. |
| 7,795,444 B2 | 9/2010 | Gray et al. |
| 7,973,142 B2 | 7/2011 | Rotello et al. |
| 8,029,808 B2 | 10/2011 | Srivastava |
| 8,106,078 B2 | 1/2012 | Gray et al. |
| 8,133,894 B2 | 3/2012 | Warshakoon et al. |
| 8,188,125 B2 | 5/2012 | Gray et al. |
| 8,258,311 B2 | 9/2012 | Gray et al. |
| 8,309,537 B2 | 11/2012 | Gardner et al. |
| 8,329,916 B2 | 12/2012 | Gray et al. |
| 8,338,615 B2 | 12/2012 | Gray et al. |
| 8,524,235 B2 | 9/2013 | Rotello et al. |
| 8,536,181 B2 | 9/2013 | Gardner et al. |
| 8,569,348 B2 | 10/2013 | Shalwitz et al. |
| 8,591,890 B2 | 11/2013 | Srivastava et al. |
| 8,778,412 B2 | 7/2014 | Shalwitz et al. |
| 8,846,685 B2 | 9/2014 | Gray et al. |
| 8,883,774 B2 | 11/2014 | Shalwitz et al. |
| 8,883,832 B2 | 11/2014 | Shalwitz et al. |
| 8,895,563 B2 | 11/2014 | Gray et al. |
| 8,946,232 B2 | 2/2015 | Gray et al. |
| 8,999,325 B2 | 4/2015 | Peters et al. |
| 8,999,971 B2 | 4/2015 | Shalwitz et al. |
| 9,045,495 B2 | 6/2015 | Gardner et al. |
| 9,096,555 B2 | 8/2015 | Shalwitz et al. |
| 9,126,958 B2 | 9/2015 | Gray et al. |
| 9,174,950 B2 | 11/2015 | Shalwitz et al. |
| 2004/0077065 A1 | 4/2004 | Evdokimov et al. |
| 2004/0097559 A1 | 5/2004 | Warshakoon et al. |
| 2004/0097560 A1 | 5/2004 | Warshakoon et al. |
| 2005/0234045 A1 | 10/2005 | Warshakoon et al. |
| 2005/0256126 A1 | 11/2005 | Warshakoon et al. |
| 2007/0238722 A1 | 10/2007 | Warshakoon et al. |
| 2007/0270407 A1 | 11/2007 | Warshakoon et al. |

(Continued)

FOREIGN PATENT DOCUMENTS

| | | |
|---|---|---|
| WO | WO 2004/043927 A1 | 5/2004 |
| WO | WO 2004/043928 A2 | 5/2004 |

(Continued)

OTHER PUBLICATIONS

Callahan, et al. Immunomodulatory Therapy for Melanoma: Ipilimumab and Beyond. Clin Dermatol. 2013; 31(2): 191-199.
Dirkx, et al. Anti-angiogenesis therapy can overcome endothelial cell anergy and promote leukocyte-endothelium interactions and infiltration in tumors. The FASEB Journal. 2006; 20:621-630.
Drake. Combination immunotherapy approaches. Annals of Oncology. 2012; 23 (Supplement 8): viii41-viii46.
Eggermont, et al. Harnessing the immune system to provide long-term survival in patients with melanoma and other solid tumors. OncoImmunology 3, e27560; Jan. 2014, pp. 1-7.

(Continued)

*Primary Examiner* — My-Chau T Tran
(74) *Attorney, Agent, or Firm* — Wilson Sonsini Goodrich & Rosati

(57) ABSTRACT

The present invention relates to combination therapies comprising at least one activator of Tie-2 and immunotherapies that target immune checkpoints. Combination therapies of the disclosure can provide therapeutic effects not obtained with singly-administered immunotherapies. Combination therapies can be used to increase the therapeutic efficacy of an immunotherapy, to provide lower dosages of an immunotherapy being administered, to lower a toxicity of an immunotherapy, or to manage a side effect of an immunotherapy.

40 Claims, 19 Drawing Sheets

(56) References Cited

U.S. PATENT DOCUMENTS

| | | |
|---|---|---|
| 2007/0299116 A1 | 12/2007 | Gray et al. |
| 2008/0004267 A1 | 1/2008 | Gray et al. |
| 2008/0051464 A1 | 2/2008 | Yi |
| 2008/0076764 A1 | 3/2008 | Peters et al. |
| 2008/0108631 A1 | 5/2008 | Gray et al. |
| 2009/0022715 A1 | 1/2009 | Rotello et al. |
| 2009/0227639 A1 | 9/2009 | Gray et al. |
| 2010/0016336 A1 | 1/2010 | Gray et al. |
| 2010/0030487 A1 | 2/2010 | Evdokimov et al. |
| 2010/0056610 A1 | 3/2010 | Peters et al. |
| 2010/0069448 A1 | 3/2010 | Gray et al. |
| 2010/0305097 A1 | 12/2010 | Warshakoon et al. |
| 2011/0110961 A1 | 5/2011 | Gardner et al. |
| 2011/0111058 A1 | 5/2011 | Shalwitz et al. |
| 2011/0112055 A1 | 5/2011 | Gardner et al. |
| 2011/0112282 A1 | 5/2011 | Rochrig et al. |
| 2011/0212951 A1 | 9/2011 | Gray et al. |
| 2011/0268694 A1 | 11/2011 | Shalwitz et al. |
| 2011/0274699 A1 | 11/2011 | Rotello et al. |
| 2011/0319455 A1 | 12/2011 | Klein et al. |
| 2012/0077853 A1 | 3/2012 | Gray et al. |
| 2012/0077975 A1 | 3/2012 | Gray et al. |
| 2012/0115876 A1 | 5/2012 | Warshakoon et al. |
| 2012/0128625 A1 | 5/2012 | Shalwitz et al. |
| 2012/0129847 A1 | 5/2012 | Peters et al. |
| 2013/0023542 A1 | 1/2013 | Gray et al. |
| 2013/0023543 A1 | 1/2013 | Gray et al. |
| 2013/0064831 A1 | 3/2013 | Humphrey |
| 2013/0095065 A1 | 4/2013 | Peters et al. |
| 2013/0095105 A1 | 4/2013 | Peters et al. |
| 2013/0096140 A1 | 4/2013 | Gray et al. |
| 2013/0158010 A1 | 6/2013 | Shalwitz et al. |
| 2013/0158045 A1 | 6/2013 | Gardner et al. |
| 2013/0324558 A1 | 12/2013 | Gray et al. |
| 2013/0331386 A1 | 12/2013 | Shalwitz et al. |
| 2014/0044707 A1 | 2/2014 | Rotello et al. |
| 2014/0066458 A1 | 3/2014 | Shalwitz et al. |
| 2014/0107391 A1 | 4/2014 | Srivastava et al. |
| 2014/0179693 A1 | 6/2014 | Shalwitz et al. |
| 2014/0221666 A1 | 8/2014 | Gray et al. |
| 2014/0242026 A1 | 8/2014 | Shalwitz et al. |
| 2014/0249100 A1 | 9/2014 | Shalwitz et al. |
| 2014/0275103 A1 | 9/2014 | Peters et al. |
| 2014/0288134 A1 | 9/2014 | Peters et al. |
| 2014/0364419 A1 | 12/2014 | Shalwitz et al. |
| 2015/0050277 A1 | 2/2015 | Peters et al. |
| 2015/0157617 A1 | 6/2015 | Shalwitz et al. |
| 2015/0210656 A1 | 7/2015 | Gray et al. |
| 2015/0218098 A1 | 8/2015 | Gardner et al. |
| 2015/0232425 A1 | 8/2015 | Alberico |
| 2015/0232575 A1 | 8/2015 | Peters et al. |
| 2015/0259335 A1 | 9/2015 | Janusz et al. |
| 2016/0008327 A1* | 1/2016 | Shalwitz ............... A61K 31/41 424/85.2 |
| 2016/0082129 A1* | 3/2016 | Peters ................... A61K 48/00 514/44 R |

FOREIGN PATENT DOCUMENTS

| | | |
|---|---|---|
| WO | WO 2007/116360 A2 | 10/2007 |
| WO | WO 2008/002569 A2 | 1/2008 |
| WO | WO 2008/002570 A2 | 1/2008 |
| WO | WO 2008/002571 A2 | 1/2008 |
| WO | WO 2010/081172 A1 | 7/2010 |
| WO | WO 2011/005330 A1 | 1/2011 |
| WO | WO 2011/057112 A1 | 5/2011 |
| WO | WO 2011/057115 A1 | 5/2011 |
| WO | WO 2011/057121 A1 | 5/2011 |
| WO | WO 2012/047966 A2 | 4/2012 |
| WO | WO 2013/056233 A1 | 4/2013 |
| WO | WO 2013/056240 A1 | 4/2013 |
| WO | WO 2014/036412 A2 | 3/2014 |
| WO | WO 2014/145068 A1 | 9/2014 |
| WO | WO 2015/126860 A1 | 8/2015 |
| WO | WO 2015/138882 A1 | 9/2015 |
| WO | WO 2016/022813 A1 | 2/2016 |
| WO | WO 2016/049183 A1 | 3/2016 |

OTHER PUBLICATIONS

Emens. Breast cancer immunobiology driving immunotherapy: vaccines and immune checkpoint blockade. Expert Rev Anticancer Ther. Dec. 2012; 12(12): 1597-1611.
Gajewski, et al. Innate and adaptive immune cells in the tumor microenvironment. Nature Immunology, vol. 14, No. 10, Oct. 2013, pp. 1014-1022.
Goel, et al. Effects of vascular-endothelial protein tyrosine phosphatase inhibition on breast cancer vasculature and metastatic progression. J Natl Cancer Inst. Aug. 21, 2013;105(16):1188-201. doi: 10.1093/jnci/djt164. Epub Jul. 30, 2013.
Griffioen. Anti-angiogenesis: making the tumor vulnerable to the immune system. Cancer Immunol Immunother. (2008) 57:1553-1558.
Harris, et al. Primer on tumor immunology and cancer immunotherapy. Journal for Immunotherapy of Cancer 2013; 1:12.
Hoos. Evolution of end points for cancer immunotherapy trials. Annals of Oncology 23 (Suppl. 8): vii47-vii52, 2012.
International search report and written opinion dated Jul. 30, 2015 for PCT/US2015/020425.
Kirkwood, et al. Adjuvant Immunotherapy of Melanoma, and Development of New Approaches Using the Neo-Adjuvant Approach in Melanoma. Clin Dermatol. 2013; 31(3): 237-250.
Pubchem. Compound Summary for: CID 52799544. Create Date: May 20, 2011. Retrieved on Apr. 27, 2015. https://pubchem.ncbi.nlm nih.gov/compound/52799544.
Quezada, et al. Exploiting CTLA-4, PD-1 and PD-L1 to reactivate the host immune response against cancer. British Journal of Cancer (2013) 108, 1560-1565 | doi: 10.1038/bjc.2013.117.
Rozali, et al. Programmed Death Ligand 2 in Cancer-Induced Immune Suppression. Hindawi Publishing Corporation, Clinical and Developmental Immunology, vol. 2012, pp. 1-8.
Scarpati, et al. Ipilimumab in the treatment of metastatic melanoma: management of adverse events. OncoTargets and Therapy, Feb. 2014, pp. 203-209.
Spranger, et al. Mechanism of tumor rejection with doublets of CTLA-4, PD-1/PD-L1, or IDO blockade involves restored IL-2 production and proliferation of CD8+ T cells directly within the tumor microenvironment. Journal for Immunotherapy of Cancer 2014, 2:3.
Terme, et al. Modulation of Immunity by Antiangiogenic Molecules in Cancer. Clinical and Developmental Immunology. 2012; Article ID 492920, 8 pages.
Vonderheide, et al. CD40 immunotherapy for pancreatic cancer. Cancer Immunol Immunother. May 2013; 62(5): 949-954.
Voskoboynik, et al. Combination Therapies for the Treatment of Advanced Melanoma: A Review of Current Evidence. Hinawi Publishing Corporation, Biochemistry Research International, vol. 2014, 9 pgs.
International search report and written opinion dated Jan. 6, 2016 for PCT/US2015/044030.

* cited by examiner

COMBINATION OF IMMUNOTHERAPIES WITH ACTIVATORS OF TIE-2

CROSS REFERENCE

This application claims the benefit of U.S. Provisional Application No. 62/034,695, filed Aug. 7, 2014, the entire content of which is incorporated herein by reference in its entirety.

BACKGROUND OF THE INVENTION

Immunotherapies can provide relief from disease states associated with the immune system. Some diseases, such as cancer, involve evasion, confusion or manipulation of the immune system to allow progression of disease, or to protect pathogens from ameliorative efforts by the immune system. Administration of immunotherapies can have unwanted effects on a subject owing to the tendency to over-modulate the subject's immune system.

SUMMARY OF THE INVENTION

In some embodiments, the invention provides a method of treating cancer, the method comprising administering to a subject in need thereof: a) a therapeutically-effective amount of a Tie-2 activator; and b) a therapeutically-effective amount of a modulator of an immune checkpoint molecule.

In some embodiments, the invention provides a pharmaceutical composition comprising: a) a Tie-2 activator; and b) a modulator of an immune checkpoint molecule, wherein the Tie-2 activator and the modulator of the immune checkpoint molecule are in the same unit dosage form.

In some embodiments, the invention provides a method of killing a cancer cell in a human, the method comprising administering to the human an amount of a Tie-2 activator that is effective to kill the cancer cell, wherein the cancer cell is killed in the human by the Tie-2 activator.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
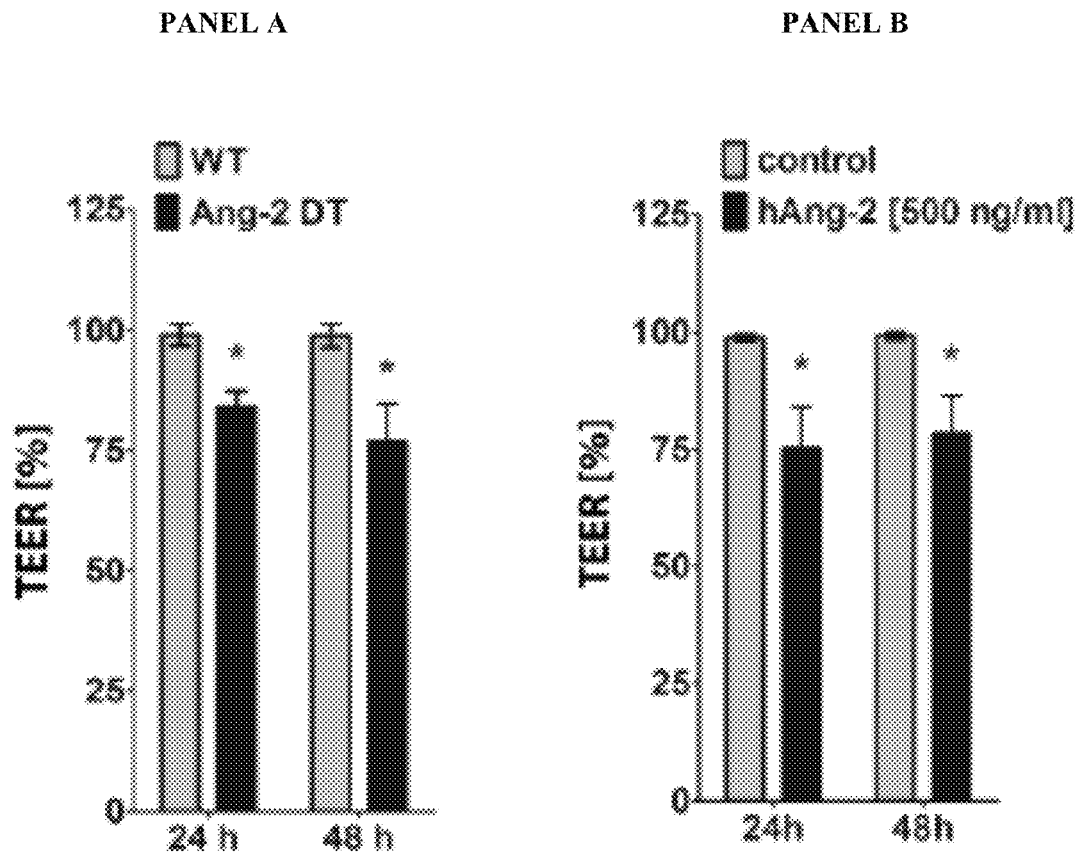
FIG. 1 is a graph illustrating transendothelial electrical resistance (TEER) measurements of primary mouse brain endothelial cells (MBMECs). PANEL A illustrates a decrease in TEER of MBMECs upon transgenic endothelial-specific overexpression of human angiopoeitin 2 (hAng-2). PANEL B illustrates a decrease in TEER of MBMECs upon recombinant human angiopoeitin 2 (rhAng-2) treatment.

Described herein are combination therapies using small molecule compounds and immunotherapies for treatment of cancer. A small molecule of the disclosure can activate Tie-2 signaling by promoting protein phosphorylation, such as phosphorylation of the Tie-2 protein. Immunotherapies can target checkpoint molecules that modulate antitumor immune responses.

Tie-2 (tyrosine kinase with immunoglobulin and epidermal growth factor homology domains 2) is a membrane receptor tyrosine kinase expressed primarily in vascular endothelial cells and a subset of hematopoietic stem cells (HSCs) and macrophages. The principle regulators of Tie-2 phosphorylation are angiopoietin 1 (Ang-1) and angiopoietin 2 (Ang-2). Ang-1 is an agonist of Tie-2, and binding of Ang-1 to Tie-2 promotes receptor phosphorylation. Ang-2 is a Tie-2 ligand that acts in a context-dependent antagonistic or agonistic manner. Binding of Ang-1 to Tie-2 increases the level of endogenous Tie-2 receptor phosphorylation and initiates downstream AKT signaling. This binding initiates a signaling cascade that can induce distinctive vascular remodeling through highly organized angiogenesis and tightening of the endothelial cell junctions (endothelium cell proximity). Within the vascular endothelium, Ang-1-Tie-2 signaling promotes endothelial cell proximity. In the HSC microenvironment, Ang-1-Tie-2 signaling contributes in a paracrine manner to the long-term repopulation of HSCs.

Under physiological conditions, the duration of Tie-2 phosphorylation is regulated by the human protein tyrosine phosphatase beta (often abbreviated as HPTPβ or HPTP beta), which removes the phosphate from the Tie-2 receptor. By inhibiting HPTPβ, the level of Tie-2 phosphorylation substantially increases, restoring proper cell proximity. HPTPβ plays a functional role in endothelial cell proliferation, viability, differentiation, vasculogenesis, and angiogenesis. HPTPβ and vascular endothelial protein tyrosine phosphatase (VE-PTP; the mouse orthologue of HPTPβ) are expressed in vascular endothelial cells throughout development. A small molecule of the disclosure can activate Tie-2 downstream signaling by inhibiting HPTPβ/VE-PTP.

Mobilization, recruitment, and adhesion of immune cells to endothelial cells, such as bone marrow-derived circulating progenitor cells (BMCPCs), promote neovascularization by supplying angiogenic growth factors to the vasculature and facilitating the incorporation of this cell population into the tissues. Angiogenesis and tumor escape from immunity are also associated with angiogenesis-mediated suppression of endothelial cell adhesion molecules involved in leukocyte-vessel wall interactions. A proper immune response to an antigen, such as an antigen present in a tumor cell, requires T-cell activation. T-cell activation in turn requires the recognition of cognate antigenic peptides through the T-cell receptor as well as the delivery of co-stimulatory signals via members of the CD28 receptor family. CD28 is constitutively expressed on T cells and binds to CD80 and CD86 on the surface of antigen presenting cells (APCs).

Upon activation, T cells transiently up-regulate the expression of checkpoint molecules. Under physiological conditions, expression of checkpoint molecules restricts the risk of autoimmune disorders. However, by restricting the risk of self-recognition by the immune system, immune checkpoints limit the ability of the immune system to recognize unwanted antigens, such as the antigens expressed by tumor cells. Some tumors can evade immune detection by up-regulating the expression of checkpoint molecules on immune cells. Other tumors can down-regulate major histocompatibility complex molecules (MHC) to escape from T cell recognition. Some tumors are able to down-regulate adhesion molecules on the vascular endothelium, including those necessary for the interaction between cells of the immune system, such as macrophages, NK cells, lymphocytes, and granulocytes with the endothelium. The inability of immune cells to interact with the endothelium impairs the ability of immune cells to infiltrate the cancer, and reduces immune-regulated killing of cancer cells.

Disclosed herein are combination therapies, and methods of using the same, comprising a Tie-2 activator and an immunotherapy that targets an immune checkpoint. Combination therapies of the disclosure can be co-administered to a subject to improve the outcome of a cancer treatment. Most immunological checkpoint molecules are members of the immunoglobulin superfamily, and are often inhibitory receptors that prevent uncontrolled immune reactions. The adaptive immune response is controlled by such checkpoint molecules, which are crucial for maintaining self-tolerance and minimizing collateral tissue damage that can occur during an immune response.

Also disclosed herein are combination therapies comprising oncolytic viruses as immunotherapies. The immune system can modify the immunogenicity and behavior of tumors, and tumors can subvert antitumor immunity, generating an immunosuppressive tumor microenvironment by various mechanisms. Oncolytic viruses can be self-replicating, tumor-selective viruses that directly lyze cancer cells. The viruses can be tumor-selective in wild-type or attenuated forms, or can be engineered to provide tumor selectivity. In some cases, the administration to a subject of a combination therapy comprising a therapeutically-effective amount of a Tie-2 activator and an oncolytic virus can provide an environment suitable to exploit the immunotherapeutic potential of oncolytic viruses. Administration of a cancer-specific oncolytic virus and a Tie-2 activator of the disclosure can specifically target a tumor while modulating vascular leakage and edema associated with the cancer or the therapy.

A combination therapy that targets immune checkpoints and promotes Tie-2 receptor phosphorylation can yield a beneficial outcome for subjects afflicted with various cancers. The integration of therapeutic agents with distinct mechanisms of action can be used to treat a cancer, to provide treatments with reduced toxic effects, and to yield better outcomes for subjects afflicted with solid or hematogical malignancies.

A combination therapy of the disclosure can be provided to subjects afflicted with various cancers to overcome tumor anergy or antigen escape from immunity. Many factors can contribute to anergy or antigen escape from immunity. Some factors include, for example, loss of T cell recognition of the antigen, an intrinsic resistance to apoptosis, accumulation of T regulatory cells ($T_{regs}$), amino acid depletion, immune inactivation of tumor-derived cytokines, and expression of ligands that negatively regulate receptors on T cells. Some tumor cells, or microorganisms, can up-regulate the expression of immune checkpoints to avoid recognition by the immune system.

A combination therapy of the disclosure can also modulate the delivery of a therapy to the brain. The blood-brain barrier (BBB) is composed of a network of vessels that form a structural and chemical barrier between the brain and systemic circulation. The vessels of the BBB have unique structures and features as compared to other vessels. Vessels of the BBB can be composed of specialized endothelial cells that lack fenestration (pores that allow rapid exchange of molecules between vessels and tissue). The endothelial cells of the BBB can also have few pinocytic vesicles that can be involved in the uptake of extracellular substances. In general, the network of vessels that form the BBB can also have extensive tight junctions that restrict cell permeability and accessibility by many existing drugs. In some cases, a Tie-2 activator of the disclosure can tighten the BBB in neurological disorders associated with vascular leakage and brain edema.

The disclosure also provides a method of modulating tumor infiltration by immune cells and immune cell trafficking. In some embodiments, the combination therapy of the disclosure can modulate tumor infiltration by modulating the expression of adhesion protein on tumor endothelial cells.

Some tumor cells, or microorganisms, could also escape immune surveillance by extravasation, or leaking from circulation into the interstitial space. A combination therapy of the disclosure can reduce leakage, or provide reduced leakage relative to a corresponding monotherapy, thus reducing cancer cell extravasation from the site of drug activity.

Immune Checkpoints.

Immune checkpoints are co-stimulatory and inhibitory elements intrinsic to the immune system. Immune checkpoints aid in maintaining self-tolerance and modulating the duration and amplitude of physiological immune responses to prevent injury to tissues when the immune system responds to pathogenic infection. An immune response can also be initiated when a T-cell recognizes antigens that are unique to a tumor cell (e.g. non-self antigens or tumor neo-antigens) or are characteristic of a tumor cell (e.g. tumor-associated antigens (TAAs)). The equilibrium between the co-stimulatory and inhibitory signals used to control the immune response from T-cells can be modulated by immune checkpoint proteins. After T-cells mature and activate in the thymus, T-cells can travel to sites of inflammation and injury to perform repair functions. T-cell function can occur either via direct action or through the recruitment of cytokines and membrane ligands involved in the immune system. The steps involved in T-cell maturation, activation, proliferation, and function can be regulated through co-stimulatory and inhibitory signals, namely through immune checkpoint proteins. Tumors can dysregulate checkpoint protein function as an immune-resistance mechanism. Thus, the development of modulators of checkpoint proteins can have therapeutic value. Non-limiting examples of immune checkpoint molecules include LAG3, BTLA, KR, CTLA4, ICOS, TIM3, A2aR, PD-1, PD-L1, PD-L2, CD40L, OX40L, CD137L, CD47, B7-H3, and B7-H4. These checkpoint molecules can operate upstream of IL-2 in a pathway.

Checkpoint molecules guard against unwanted and harmful self-directed activation of the immune system (autoimmunity). Although necessary in aiding in the suppression of autoimmunity, these molecules can hinder immunotherapies aimed at targeting malignant self-cells that largely display the same array of surface molecules as the parent cells. Therapies aimed at overcoming these mechanisms of peripheral tolerance, particularly by blocking the inhibitory checkpoints, offer the potential to generate antitumor activity, either as monotherapies or in combination with other therapies that directly or indirectly enhance presentation of tumor epitopes to the immune system.

Immunological checkpoints can be molecules that regulate inhibitory signaling pathways (for example, LAG3, CTLA4, PD-1, and TIM3) or molecules that regulate stimulatory signaling pathways (for example, by ICOS). Several proteins in the extended immunoglobulin superfamily can be ligands for immunological checkpoints. Non-limiting examples of immune checkpoint ligand proteins include B7-H4, ICOSL, PD-L1, PD-L2, CD40L, OX40L, CD86, and CD137L.

LAG3 (Lymphocyte-activation gene 3) is expressed on activated antigen-specific cytotoxic T cells, and can enhance the function of regulatory T-cells and independently inhibit CD8$^+$ effector T-cell activity. LAG3 is a CD-4-like negative regulatory protein with a high affinity binding site to MHC Class II, which are upregulated on some epithelial cancers, to provide tolerance of T cell proliferation and homeostasis. Blockage of the LAG-3/Class II interaction using a LAG-3-IG fusion protein enhances antitumor immune responses. Therapeutics targeting LAG3 include IMP321 and other monoclonal antibodies.

BTLA (B- and T-lymphocyte attenuator) can inhibit T-cells when associated with HVEM (herpes-virus entry mediator) as a ligand. HVEM can be expressed on melanoma and endothelial cancer cells. BTLA levels can be high on TILs from subjects with melanoma, and BTLA-expressing T-cells can be inhibited in the presence of HVEM.

KIR (killer immunoglobulin-like receptor) is expressed by Natural Killer (NK) cells and a subset of T lymphocytes. KIRs are largely cell surface inhibitory receptors specific for allelic forms of human leukocyte antigen (HLA) class I molecules. Upon engagement with HLA class I molecules, KIRs block NK cell activation and function. Blockage of KIRs can lead to blockage of NK cell activation and function.

CTLA4 (cytotoxic T-lymphocyte antigen 4) is also known as CD152 (Cluster of differentiation 152). CTLA4 shares sequence homology and ligands (CD80/B7-1 and CD86/B7-2) with the costimulatory molecule CD28, but differs by delivering inhibitory signals to T cells expressing CTLA4 as a receptor. CTLA4 has a much higher overall affinity for both ligands and can out-compete CD28 for binding when ligand densities are limiting.

CTLA4 is expressed on the surface of CD8$^+$ effector T-cells, and plays a functional role in the initial activation stages of both naive and memory T cells. CTLA4 counteracts the activity of CD28 via increased affinity for CD80 and CD86 during the early stages of T-cell activation. The major functions of CTLA4 include downmodulation of helper T-cells and enhancement of regulatory T-cell immunosuppressive activity. Evidence for the importance of CTLA4 can be demonstrated through the lethal systemic immune hyperactivation phenotype in Ctla4 −/−mice.

CTLA4 can also downregulate immune system functions via inhibition of IL-2 production and IL-2 receptor expression. CTLA4 can inhibit CD28-dependent upregulation of IL-2, and the inhibition of IL-2 production can lead to cell cycle arrest. The decrease in IL-2 and subsequent cell cycle arrest can account for the reduced T-cell proliferation observed in the presence of CTLA4.

CTLA4 includes an extracellular domain, a transmembrane domain, and a cytoplasmic tail. Alternate transcriptional splice variants encoding different isoforms exist. The membrane-bound isoform can function as a homodimer interconnected by a disulfide bond, and the soluble isoform can function as a monomer. Mutations in CTLA4 can be associated with, for example, insulin-dependent diabetes mellitus, Graves' disease, Hashimoto thyroiditis, celiac disease, systemic lupus erythematosus, thyroid-associated orbitopathy, and other autoimmune diseases.

Therapies targeting CTLA4 can be developed to circumvent tumor resistance mechanisms. Inhibition of CTLA4 can lead to a broad enhancement of immune responses that are dependent on helper T-cells. Thus, therapeutics aimed at blocking CTLA4 can assist in evading tumor cell resistance mechanisms. Examples of therapies targeting CTLA4 include ipilimumab and tremelimumab, monoclonal antibodies that can target CTLA4 and can be used in the treatment of, for example, melanoma. Therapies can also be directed toward increasing the activity of CTLA4 for the treatment of autoimmune diseases. Fusion proteins of CTLA4 and antibodies can increase the immune response in patients with, for example, rheumatoid arthritis, or patients sensitized to the Epstein Barr Virus (EPV) undergoing renal transplantation.

ICOS (Inducible T-cell COStimulator), also known as CD278, is a CD28-superfamily costimulatory molecule that is expressed on activated T cells. CD40 and CD134 are examples of additional co-stimulatory molecules.

TIM3 (T-cell immunoglobulin and mucin domain-containing protein 3), also known as Hepatitis A virus cellular receptor 2 (HAVCR2) is a Th1-specific cell surface protein that regulates macrophage activation. TIM3 can inhibit helper T-cell responses via association with the TIM3 ligand, galectin 9. Galectin 9 can be upregulated in various types of cancer, including breast cancer. TIM3 can be co-expressed with PD-1 on tumor specific CD8$^+$ T-cells and inhibition of both molecules can significantly enhance the proliferation and cytokine production of T-cells.

Four types of adenosine receptors, A1, A2A, A2B, and A3 receptors, are expressed on the surface of immune cells. On T cells, the predominant subtype expressed is A2A adenosine receptor (A2aR). Immunosupressive signaling through the A2aR receptor can control the cytokine secretion pattern of NK cells and function to protect inflamed tissues from excessive damage by immune cells. A2aR receptors inhibit T-cell responses by driving CD4$^+$ T-cells to express FOXP3 (forkhead box P3). FOXP3 can then cause the CD4$^+$ T-cells to develop into regulatory T-cells. Deletion of A2aR can lead to pathological inflammatory responses to infection.

PD-1 is an inhibitory receptor belonging to the CD28/CTLA4 family and is expressed on the surface of activated T lymphocytes, B cells, monocytes, DCs, NK cells, and $T_{regs}$. In contrast to CTLA4, the major role of PD-1 is limitation of activity of T cells in peripheral tissues at the time of an inflammatory response to infection and to limit autoimmunity. Chronic antigen exposure can lead to persistently-high levels of PD-1 expression, which can induce a state of exhaustion or anergy of antigen-specific T-cells, which can be at least partially reversed by PD-1 blockade.

Two ligands for PD-1, PD-L1 and PD-L2, are expressed on T cells, APCs, and malignant cells, and function to suppress self-reactive lymphocytes and to inhibit the effector function of TAA-specific cytotoxic T lymphocytes (CTLs). Accordingly, a therapy that targets PD-1, PD-L1, or PD-L2 has the potential to restore the cytotoxic activity of TAA-specific T cells.

Upon engagement of ligands, PD-1 can inhibit kinases involved in T-cell activation through the phosphatase, SHP2. PD-1 can limit the activity of T-cells in peripheral tissues at the time of an inflammatory response to an infection and limit autoimmunity. The decrease in the proliferation of T-cells can lead to a decrease in IL-2 secretion. PD-1 can also be highly expressed on $T_{regs}$, which can have an immunosuppressive function, and further increase the proliferation of $T_{regs}$. Tumors can be highly infiltrated with $T_{regs}$; thus, blockade of PD-1 can diminish the immunosuppressive function of the intratumoral $T_{regs}$.

Due to the broad expression pattern, PD-1 can also enhance NK activity in tumors or tissues. PD-1 can increase antibody production through PD-1$^+$ B-cells. Chronic antigen exposure observed in viral infection and cancer can lead to persistent PD-1 activation, and can T-cell anergy among cognate antigen-specific T-cells. This anergic state can be reversed through a blockade of PD-1.

PD-1 can also be expressed on tumor infiltrating lymphocytes (TILs) in many tumor types. The enhanced PD-1 expression of CD4$^+$ cells can reflect the high expression of PD-1 on regulatory T-cells within tumors. PD-1 can also be highly expressed on CD8$^+$ cells and can reflect an anergic state. Consistent with the increased expression of PD-1 on lymphocytes from many tumors, the ligands of PD-1 can also be highly expressed on the tumor cell surface. PD-L1 can be highly expressed on, for example, melanoma, ovarian cancer, lung cancer, and renal cancer cells. PD-L2 can be highly expressed on, for example, primary mediastinal B-cell lymphoma, follicular cell B-cell lymphoma, and Hodgkin's lymphoma. Anti-PD-1 antibodies can induce regression of several tumor types including colon, renal, lung, and melanoma. Therapies targeting PD-1 directly or the interaction between PD-1 and a ligand include nivolumab, pembrolizumab, pidilizumab, and AMP-224.

B7-H3 can costimulate proliferation of both CD4$^+$ and CD8$^+$ T cells, enhance the induction of cytotoxic T cells, and selectively stimulate interferon γ (IFN-γ) production in the presence of T cell receptor signaling. The B7-H3 receptor can be expressed in dendritic cells and monocytes.

B7-H4, also known as B7S 1 or B7x, is a coinhibitory member of the B7 family that negatively regulates neutrophil-mediated innate immune responses. The B7-H4 receptor can be expressed in B cells and antigen presenting cells. The B7-H4 receptor can also be overexpressed in breast, ovarian, lung cancer, and other solid tumors.

Immunotherapies of the invention include those that modulate a checkpoint molecule or a checkpoint protein. Non-limiting examples of agents that modulate a checkpoint molecule or a checkpoint protein include cytokines, immunotoxins, recombinant proteins, antibodies, monoclonal antibodies, tumor-specific monoclonal antibodies, antibody-drug conjugates, immunotoxins, and any agent that modulates, up-regulates, down-regulates, agonizes, antagonizes, inhibits, or induces one or more of LAG3, BTLA, KIR, CTLA4, ICOS, TIM3, A2aR, PD-1, B7-H3, B7-H4, ICOSL, PD-L1, PD-L2, CD40L, OX40L, CD47, CD86, and CD137L. In some embodiments, the immunotoxin therapy is a therapy against one or more of CD5, CD7, CD19, CD22, CD25 (T-NHL), CD30, and CD38 (B-NHL). In some embodiments, the immunotherapy is ipilimumab, nivolumab, tremelimumab, pembrolizumab, pidilizumab, AMP-224 or Resimmune™ (also called A-dmDT390-bisFv (UCHT1)). The agent can be administered in the same unit dosage form as a small molecule described herein, or in a separate dosage form.

Non-limiting examples of cells whose activity can be modulated by a combination therapy include: endothelial cells; B cells; CD4; CD8; blood cells, including red blood cells and white blood cells; dendritic cells, including dendritic antigen presenting cells; leukocytes; macrophages; memory B cells; memory T cells; monocytes; NK cells; neutrophil granulocytes; helper T cells; and cytotoxic T cells. A combination therapy disclosed herein can modulate the interaction of cells of the immune system with the endothelium of a subject.

Oncolytic Viruses.

Oncolytic viruses (OVs) can selectively infect, replicate in, and kill tumor cells with minimal impact on normal tissue. These tumor-specific properties can be dependent on the expression of surface receptors that allow viral binding and entry, and on the permissiveness of the tumor cell toward viral replication. Genetic manipulation of the viral genome can improve the therapeutic value of OVs by enhancing capacity for targeted tumor killing. Through transgene insertion, OVs can serve as directed gene-delivery vehicles, and thus accommodate a diverse array of therapeutic strategies. Killing directed by OVs can be direct via the lytic replication cycle of the virus or indirect by induction of endogenous cell death. The latter can occur via the expression of transgenes from a modified viral genome and can include expression of: pro-cell death genes such as TRAIL and Fas ligand; tumor suppressors such as p53 or p16; and short hairpin RNAs that target oncogenes such as KRAS, NRAS, HRAS, hTERT, MYC, and MYCN. Tumor cell killing can also occur via induction of autophagy either intrinsic to OV infection or enhanced by transgene-mediated expression of autophagy inducers like Beclin-1 or components of the mammalian target of rapamycin (mTOR) pathway. Further tumor cell killing can be tumor cell extrinsic, including long-term suppression of the tumor vasculature or induction of an immune response.

Some oncolytic viruses, in the course of infection, can stimulate angiogenesis and increase the vascular permeability of tumors. This increased vascular leakage can generate unwanted pathologies, like edema, that limit the effective dose of OVs in a subject. In some embodiments, administration to a subject in need thereof of a therapeutically-effective amount of a Tie-2 activator and a therapeutically-effective amount of an OV can be used to treat a cancer while suppressing the swelling, edema, and vascular leak caused by the OV.

Some oncolytic viruses can cross the blood brain barrier and target a brain tumor, such as a glioma. In some embodiments, administration to a subject in need thereof of a Tie-2 activator and a therapeutically-effective amount of an OV can effectively treat a brain tumor while reducing swelling, edema, and vascular leak in the brain. For instance, brain tumor-related edema (BTRE) can be caused by two main mechanisms, vasogenic and cytotoxic. While BTRE is classically associated with vasogenic edema, cytotoxic edema can also be associated in the pathophysiology of peritumoral swelling. Vasogenic edema can be caused by the disruption of the BBB, disruption of which allows leakage of fluids from the blood into the brain parenchyma. The disturbance of the BBB can be due to two main mechanisms: (1) decreased expression of functioning tight-junctions and disruption of normally expressed tighjunctions; and (2) increased endothelial pinocytosis and endothelial fenestrations. Cytotoxicedema can be associated with glioma-induced neuronal cell death and neurodegeneration, and lead to further brain swelling and neurological deficits. Administration of a Tie-2 activator of the disclosure in conjunction with an oncolytic virus can effectively treat a brain tumor while modulating vascular leak, swelling and brain edema.

Induction of a tumor immune response by OVs can be either indirect or direct. Indirect induction of a tumor immune response by OVs can be subsequent to the lysing of cancer cells, resulting in the release of TAAs, proinflammatory cytokines, chemokines, and other danger signals, and facilitating immune cell recruitment and activation within tumors. Direct induction of a tumor immune response by OVs can occur through transgene-mediated delivery of immunomodulatory factors to the tumor cell. Non-limiting examples of such immunomodulatory factors include cytokines such as IL-12, IL-2, IL-4, IL-18, IL-24, TNFα, GM-CSF, Fms-like tyrosine kinase-3 ligand (FLT3L), CCL5, CCL3, and CCL19. Direct induction of a tumor immune response by OVs can also occur through transgene-mediated delivery of tumor-associated antigens (TAAs), including ovalbumin (OVA), LacZ, and human dopachrome tautomerase (hDCT).

Non-limiting examples of oncolytic viruses include reovirus, Newcastle disease virus (NDV), vesicular stomatitis virus (VSV), Herpes simplex virus (HSV), oncorine (H101), poliovirus, parvovirus, adenovirus, alphavirus, poxvirus, vaccinia virus, and human rhinovirus type-2.

Adenovirus-based OVs can be used in methods of the disclosure. Adenovirus is a non-enveloped virus with a linear double-stranded DNA genome. Adenoviruses can enter host cells using interactions between viral surface proteins and host cell receptors that lead to endocytosis of the adenovirus particle. Once inside the host cell cytoplasm, the adenovirus particle is released by the degradation of the endosome. Using cellular microtubules, the adenovirus particle gains entry into the host cell nucleus, where adenoviral DNA is released. Inside the host cell nucleus, the adenoviral DNA is transcribed and translated. Adenoviral DNA is not integrated into the host cell genome. Adenoviral DNA is not replicated during host cell division.

Herpes simplex virus (HSV)-based OVs can be used in methods of the disclosure. HSV is an enveloped virus with a linear double-stranded DNA genome. Interactions between surface proteins on the host cell and HSV lead to pore formation in the host cell membrane. These pores allow HSV to enter the host cell cytoplasm. Inside the host cell, HSV uses the nuclear entry pore to enter the host cell nucleus where HSV DNA is released. HSV can persist in host cells in a state of latency. Herpes simplex virus 1 and 2 (HSV-1 and HSV-2), also known as human herpes virus 1 and 2 (HHV-1 and HHV-2), are members of the herpes virus family.

Alphavirus-based OVs can be used to deliver nucleic acids in methods of the disclosure. Examples of alphavirus-based vectors include vectors derived from semliki forest virus and sindbis virus. Alphavirus-based OVs can provide high transgene expression and the ability to transduce a wide variety of cells. Alphaviruses can be modified to target specific tissues. Alphaviruses can persist in a latent state in host cells, thereby offering the advantage of long-term transgeneA production in the cell.

Poxvirus and vaccinia-based OVs such as orthopox or avipox OVs can be used in methods of the disclosure. Pox virus is a double stranded DNA virus that can infect diving and non-dividing cells. Pox viral genome can accommodate up to 25 kilobases (kb) of transgene sequence. Multiple transgenes can be delivered using a single vaccinia virus.

Poliovirus-based OVs can be used in methods of the disclosure. Poliovirus is a non-enveloped virus with a single-stranded positive-sense RNA genome about 7500 nucleotides in length with a protein capsid. Poliovirus infects human cells by binding to an immunoglobulin-like receptor, CD155, on the cell surface. Attached to the host cell membrane, the virus is taken up by receptor-mediated endocytosis. After internalization, the viral RNA is released. The viral RNA then acts as a messenger RNA and is immediately translated by the host cell translation machinery. Translation causes inhibition of cellular protein synthesis in favor of virus-specific protein production.

Unlike host cell mRNA, the 5' end of poliovirus RNA is extremely long—over 700 nucleotides—and highly structured. This region of the viral genome is called the internal ribosome entry site (IRES) and directs translation of the viral RNA. Poliovirus mRNA is translated as one long polypeptide. This polypeptide is then auto-cleaved by internal proteases into approximately 10 individual viral proteins. Once synthesized, the poliovirus proteins use an RNA dependent RNA polymerase to synthesize additional copies of the viral genome. The poliovirus proteins and newly synthesized viral genomes assemble into new viral particles, followed by cell lysis and release of poliovirus virions.

A hybrid OV having properties of two or more OVs can be used for OV therapy. Hybrid vectors can be engineered to reduce toxicity or improve therapeutic transgene expression in target cells. Non-limiting examples of hybrid OVs include HSV/adenovirus, poxvirus/HSV, poliovirus/human rhinovirus type-2, and poxvirus/adenovirus.

Tie-2 Activators.

Compounds disclosed herein can be effective as Tie-2 activators. The compounds can promote that activity, for example, by binding to or inhibiting HPTPβ. Such compounds can bind to HPTPβ, for example, by mimicking the binding mechanism of a native substrate, such as a phosphorylated compound. A compound can be a phosphate mimetic or bioisostere, for example, a sulfamic acid. The compound could also be derived from an amino acid building block or comprise an amino acid backbone for efficiency and economy of synthesis.

In some embodiments, a compound of the invention is a compound of the formula:

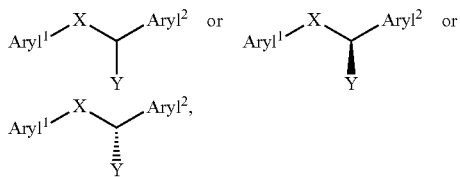

wherein:
Aryl¹ is an aryl group which is substituted or unsubstituted;
Aryl² is an aryl group which is substituted or unsubstituted;
X is alkylene, alkenylene, alkynylene, an ether linkage, an amine linkage, an amide linkage, an ester linkage, a thioether linkage, a carbamate linkage, a carbonate linkage, a sulfone linkage, any of which is substituted or unsubstituted, or a chemical bond; and Y is H, aryl, heteroaryl, NH(aryl), NH(heteroaryl), $NHSO_2R^g$, or $NHCOR^g$, any of which is substituted or unsubstituted, or

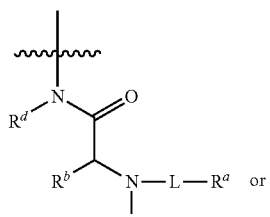

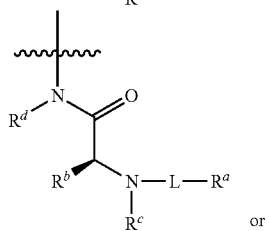

wherein:
L is alkylene, alkenylene, or alkynylene, any of which is substituted or unsubstituted, or together with the nitrogen atom to which L is bound forms an amide linkage, a carbamate linkage, or a sulfonamide linkage, or a chemical bond, or together with any of $R^a$, $R^b$, $R^c$, and $R^d$ forms a ring that is substituted or unsubstituted; $R^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, $R^b$, $R^c$, and $R^d$ forms a ring that is substituted or unsubstituted; $R^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, $R^a$, $R^c$, and $R^d$ forms a ring that is substituted or unsubstituted; $R^c$ is H or alkyl which is substituted or unsubstituted, or together with any of L, $R^a$, $R^b$, and $R^d$ forms a ring that is substituted or unsubstituted; $R^d$ is H or alkyl which is substituted or unsubstituted, or together with any of L, $R^a$, $R^b$, and $R^c$ forms a ring that is substituted or unsubstituted; and $R^g$ is H, alkyl, alkenyl, alkynyl, aryl, arylalkyl, heterocyclyl, heterocyclylalkyl, heteroaryl, or heteroarylalkyl, any of which is substituted or unsubstituted, or a pharmaceutically-acceptable salt, tautomer, or zwitterion thereof.

In some embodiments, aryl¹ is substituted or unsubstituted phenyl, aryl² is substituted or unsubstituted heteroaryl, and X is alkylene. In some embodiments, aryl¹ is substituted phenyl, aryl² is substituted heteroaryl, and X is methylene.

In some embodiments, a compound is of the formula:

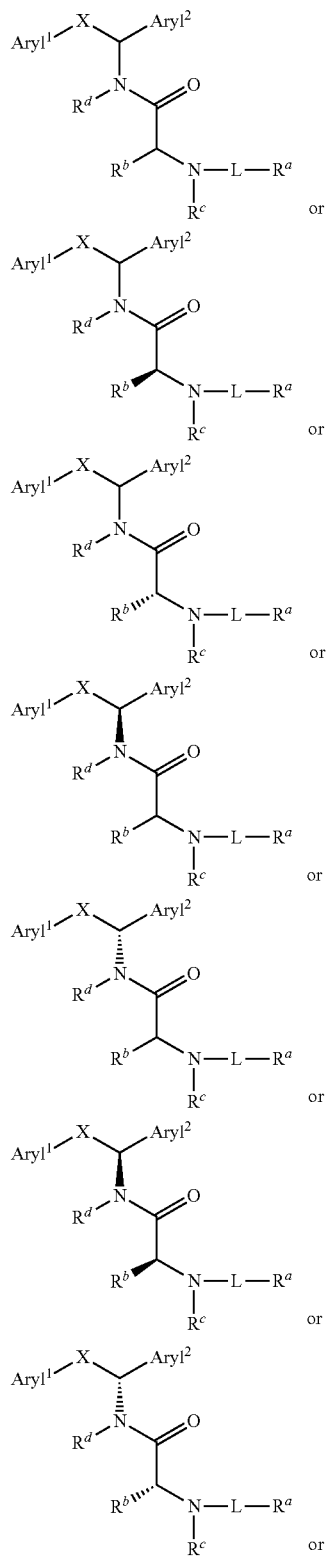

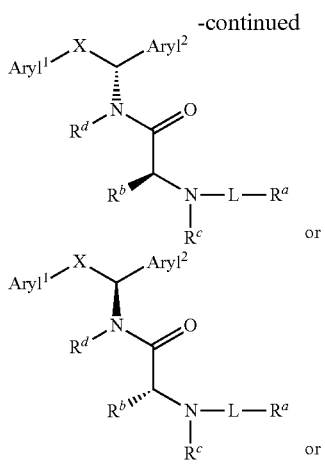

wherein aryl¹ is para-substituted phenyl, aryl² is substituted heteroaryl; X is methylene; L is alkylene, alkenylene, or alkynylene, any of which is substituted or unsubstituted, or together with the nitrogen atom to which L is bound forms an amide linkage, a carbamate linkage, or a sulfonamide linkage, or a chemical bond; $R^a$ is H, alkyl, alkenyl, alkynyl, aryl, arylalkyl, heterocyclyl, heterocyclylalkyl, heteroaryl, or heteroarylalkyl, any of which is substituted or unsubstituted; $R^b$ is H, alkyl, alkenyl, alkynyl, aryl, arylalkyl, heterocyclyl, heterocyclylalkyl, heteroaryl, or heteroarylalkyl, any of which is substituted or unsubstituted; $R^c$ is H or alkyl which is substituted or unsubstituted; and $R^d$ is H or alkyl which is substituted or unsubstituted.

In some embodiments, aryl¹ is para-substituted phenyl; aryl² is a substituted thiazole moiety; X is methylene; L together with the nitrogen atom to which L is bound forms a carbamate linkage; $R^a$ is alkyl, which is substituted or unsubstituted; $R^b$ is arylalkyl, which is substituted or unsubstituted; $R^c$ is H; and $R^d$ is H.

In some embodiments, Aryl² is:

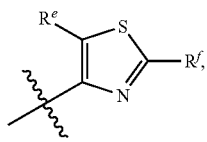

wherein $R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted; and $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted.

In some embodiments, $R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and $R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted. In some embodiments, $R^e$ is H, OH, F, Cl, Br, I, alkyl, or an alkoxy group, any of which is substituted or unsubstituted and $R^f$ is alkyl, aryl, heterocyclyl, or heteroaryl, any of which is substituted or unsubstituted. In some embodiments, aryl¹ is 4-phenylsulfamic acid; $R^a$ is alkyl, which is substituted or unsubstituted; $R^b$ is arylalkyl, which is substituted or unsubstituted; $R^e$ is H; and $R^f$ is heteroaryl. In some embodiments, aryl¹ is 4-phenylsulfamic acid; $R^a$ is alkyl; which is substituted or unsubstituted; $R^b$ is arylalkyl, which is substituted or unsubstituted; $R^e$ is H; and $R^f$ is alkyl.

In some embodiments, Aryl² is:

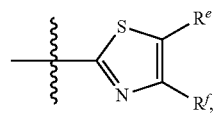

wherein $R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted, $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl, any of which is substituted or unsubstituted. In some embodiments, $R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and $R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted. In some embodiments, $R^e$ is H, OH, F, Cl, Br, I, alkyl, or an alkoxy group, any of which is substituted or unsubstituted; and $R^f$ is alkyl, aryl, heterocyclyl, or heteroaryl, any of which is substituted or unsubstituted. In some embodiments, aryl¹ is 4-phenylsulfamic acid; $R^a$ is alkyl, which is substituted or unsubstituted; $R^b$ is arylalkyl, which is substituted or unsubstituted; $R^e$ is H; and $R^f$ is heteroaryl.

In some embodiments, a substituted phenyl group is:

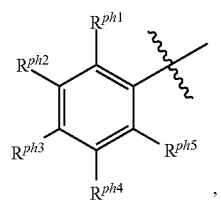

wherein:
each of $R^{ph1}$, $R^{ph2}$, $R^{ph3}$, $R^{ph4}$, and $R^{ph5}$ is independently H, OH, F, Cl, Br, I, CN, sulfamic acid, tosylate, mesylate, triflate, besylate, alkyl, alkenyl, alkynyl, an alkoxy group, a sulfhydryl group, a nitro group, a nitroso group, an azido group, a sulfoxide group, a sulfone group, a sulfonamide group, an ether group, a carboxylic acid group, a carboxaldehyde group, an ester group, an amine group, an amide group, a carbonate group, a carbamate group, a thioether group, a thioester group, a thioacid group, aryl, arylalkyl, heterocyclyl, heterocyclylalkyl, heteroaryl, or heteroarylalkyl.
Illustrative compounds include the following:
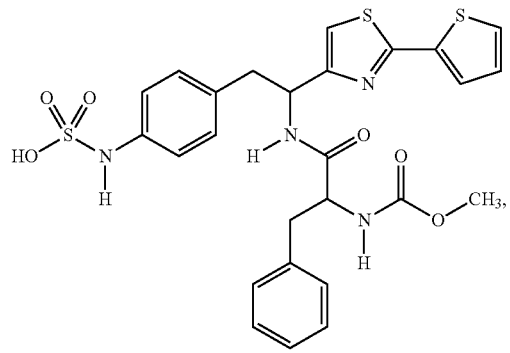 [SMILES: COC(=O)NC(Cc1ccccc1)C(=O)NC(Cc1ccc(NS(=O)(=O)O)cc1)c1csc(-c2cccs2)n1]
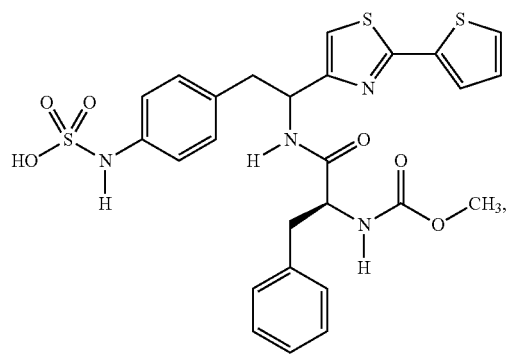
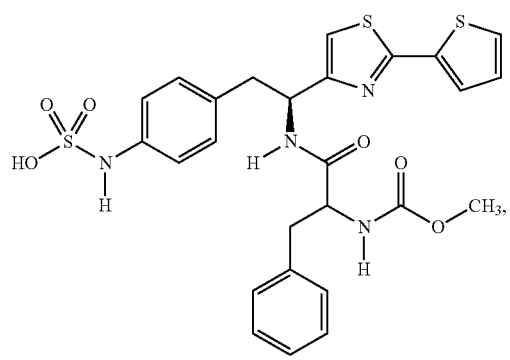
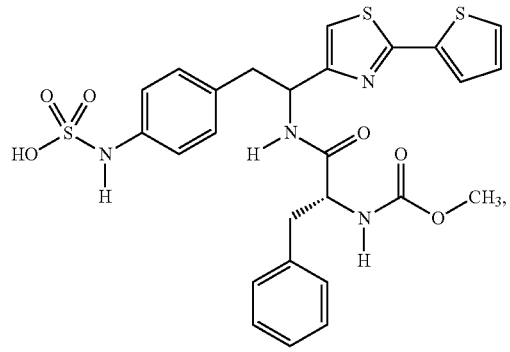
-continued
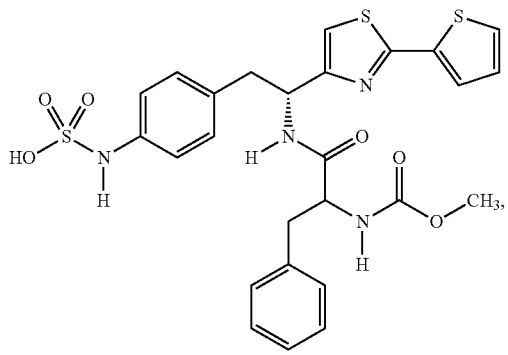 [SMILES: COC(=O)NC(Cc1ccccc1)C(=O)NC(Cc1ccc(NS(=O)(=O)O)cc1)c1csc(-c2cccs2)n1]
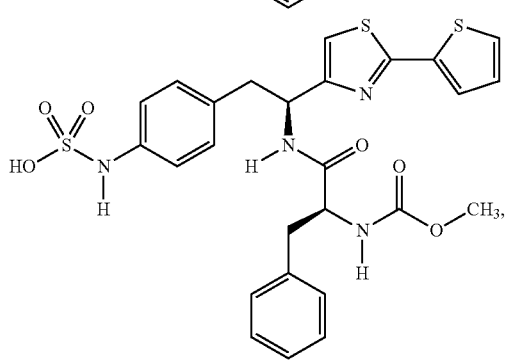
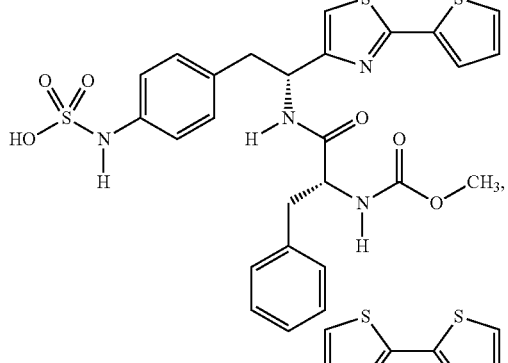
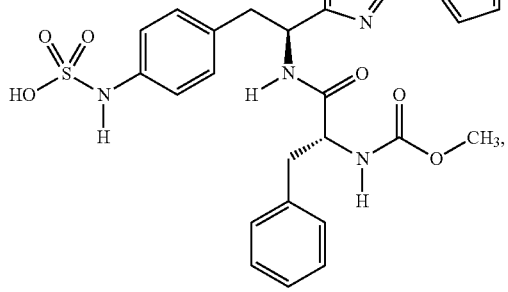
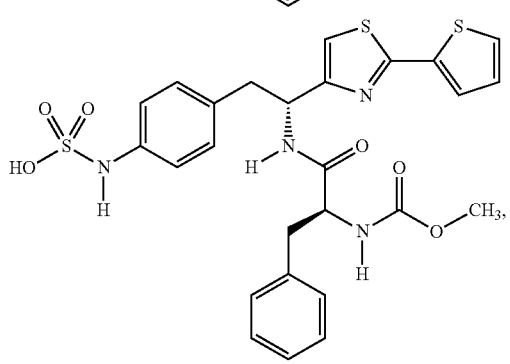

-continued

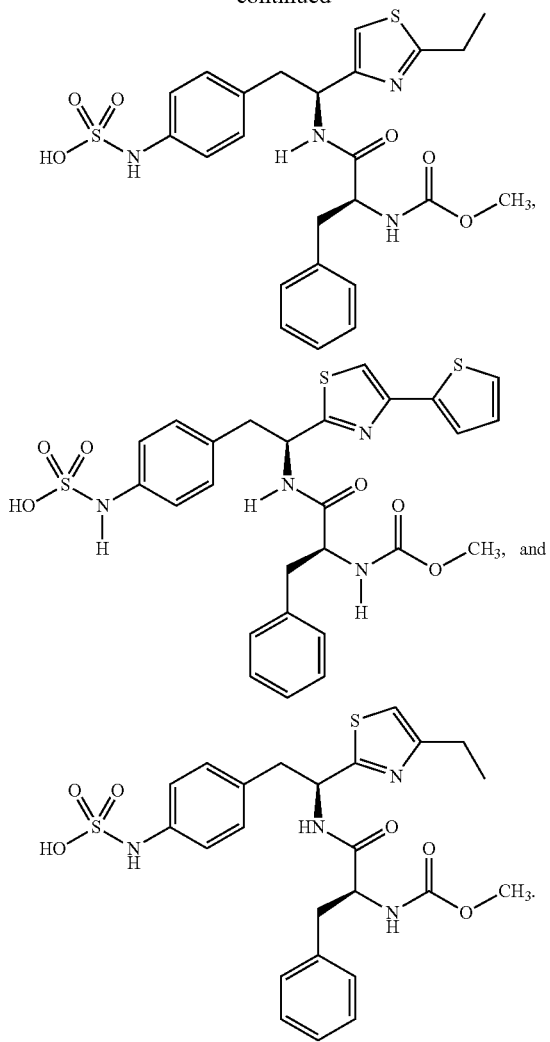

Optional Substituents for Chemical Groups.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, and ester groups.

Non-limiting examples of alkyl and alkylene groups include straight, branched, and cyclic alkyl and alkylene groups. An alkyl group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of cyclic alkyl groups include cyclopropyl, cyclobutyl, cyclopentyl, cyclohexyl, cycloheptlyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_r$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl.

An aryloxy group can be, for example, an oxygen atom substituted with any aryl group, such as phenoxy.

An aralkyl group can be, for example, any alkyl group substituted with any aryl group, such as benzyl.

An arylalkoxy group can be, for example, an oxygen atom substituted with any aralkyl group, such as benzyloxy.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

An acyl group can be, for example, a carbonyl group substituted with hydrocarbyl, alkyl, hydrocarbyloxy, alkoxy, aryl, aryloxy, aralkyl, arylalkoxy, or a heterocycle. Non-limiting examples of acyl include acetyl, benzoyl, benzyloxycarbonyl, phenoxycarbonyl, methoxycarbonyl, and ethoxycarbonyl.

An acyloxy group can be an oxygen atom substituted with an acyl group. An ester or an ester group comprises an acyloxy group. A non-limiting example of an acyloxy group, or an ester group, is acetate.

A carbamate group can be an oxygen atom substituted with a carbamoyl group, wherein the nitrogen atom of the carbamoyl group is unsubstituted, monosubstituted, or disubstituted with one or more of hydrocarbyl, alkyl, aryl, heterocyclyl, or aralkyl. When the nitrogen atom is disubstituted, the two substituents together with the nitrogen atom can form a heterocycle.

Pharmaceutically-Acceptable Salts.

The invention provides the use of pharmaceutically-acceptable salts of any compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, piprazole, imidazole, or pyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a piprazole salt, an imidazole salt, or a pyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, or a maleate salt.

A compound herein can be a salt of an acidic group, for example:

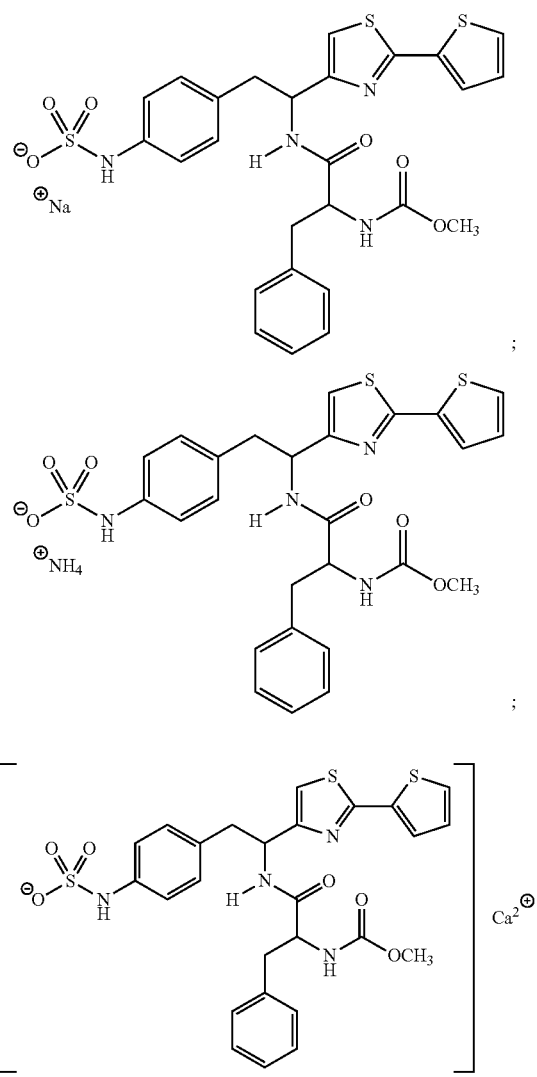

21
-continued

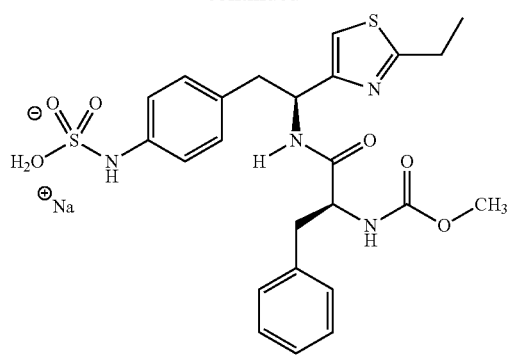

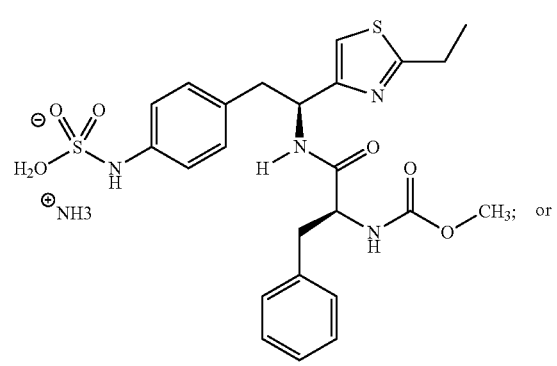

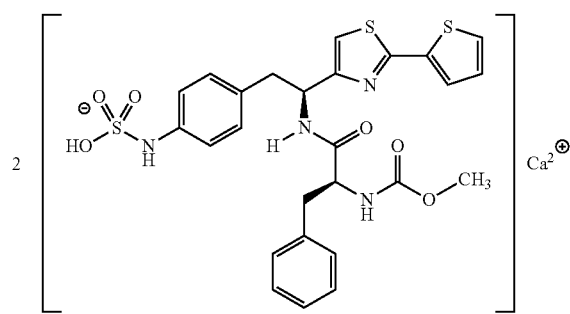

A compound herein can be a salt of a basic group formed from a strong acid, for example:

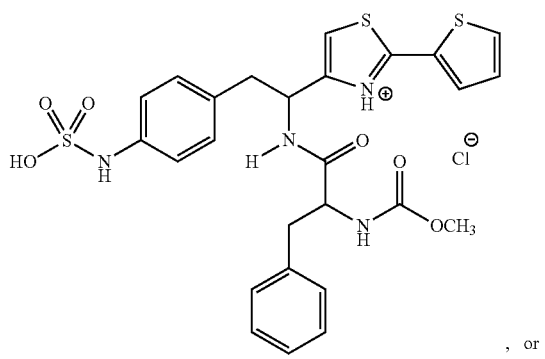

, or

22
-continued

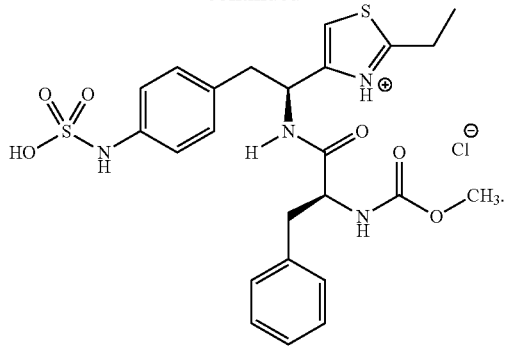

A compound herein can also exist in a zwitterionic form, for example:

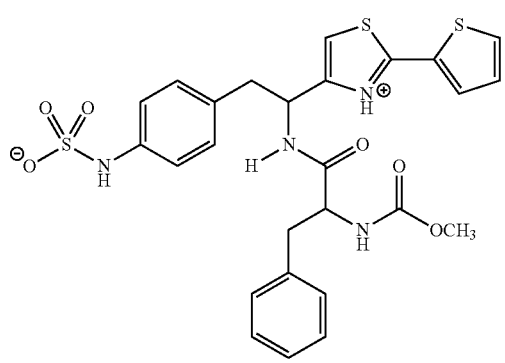

, or

Formulations.

A pharmaceutical composition of the disclosure can provide a therapeutically-effective amount of an activator of Tie-2 and an immunotherapy.

The disclosed formulations can comprise one or more pharmaceutically acceptable agents, which alone or in combination solubilize a compound herein or a pharmaceutically acceptable salt thereof.

In some embodiments, a compound or pharmaceutically-acceptable salt thereof is present in a formulation in an amount of about 0.1 mg/mL to about 100 mg/mL, about 0.1 mg/mL to about 1 mg/mL, about 0.1 mg/mL to about 5 mg/mL, about 5 mg/mL to about 10 mg/mL, about 10 mg/mL to about 15 mg/mL, about 15 mg/mL to about 20 mg/mL, about 20 mg/mL to about 25 mg/mL, about 25 mg/mL to about 30 mg/mL, about 30 mg/mL to about 35 mg/mL, about 35 mg/mL to about 40 mg/mL, about 40 mg/mL to about 45 mg/mL, about 45 mg/mL to about 50 mg/mL, about 50 mg/mL to about 55 mg/mL, about 55 mg/mL to about 60 mg/mL, about 60 mg/mL to about 65 mg/mL, about 65 mg/mL to about 70 mg/mL, about 70 mg/mL to about 75 mg/mL, about 75 mg/mL to about 80 mg/mL, about 80 mg/mL to about 85 mg/mL, about 85 mg/mL to about 90 mg/mL, about 90 mg/mL to about 95 mg/mL, or about 95 mg/mL to about 100 mg/mL.

In some embodiments, a compound or pharmaceutically-acceptable salt thereof is present in a formulation in an amount of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL about 62 mg/mL, about 63 mg/mL, about 64 mg/mL, about 65 mg/mL, about 66 mg/mL, about 67 mg/mL, about 68 mg/mL, about 69 mg/mL, about 70 mg/mL, about 71 mg/mL about 72 mg/mL, about 73 mg/mL, about 74 mg/mL, about 75 mg/mL, about 76 mg/mL, about 77 mg/mL, about 78 mg/mL, about 79 mg/mL, about 80 mg/mL, about 81 mg/mL about 82 mg/mL, about 83 mg/mL, about 84 mg/mL, about 85 mg/mL, about 86 mg/mL, about 87 mg/mL, about 88 mg/mL, about 89 mg/mL, about 90 mg/mL, about 91 mg/mL about 92 mg/mL, about 93 mg/mL, about 94 mg/mL, about 95 mg/mL, about 96 mg/mL, about 97 mg/mL, about 98 mg/mL, about 99 mg/mL, or about 100 mg/mL.

A formulation that is disclosed herein can be made more soluble by the addition of an additive or agent. The improvement of solubility of the formulation can increase by about 5%, about 10%, about 15%, about 20%, about 25%, about 30%, about 35%, about 40%, about 45%, about 50%, about 55%, about 60%, about 65%, about 70%, about 75% about 80%, about 85%, about 90%, about 95%, about 100%, about 110%, about 120%, about 130%, about 140%, about 150%, about 160%, about 170%, about 180%, about 190%, about 200%, about 225%, about 250%, about 275%, about 300%, about 325%, about 350%, about 375%, about 400%, about 450%, or about 500%.

A formulation disclosed herein can be stable for about 1 day, about 2 days, about 3 days, about 4 days, about 5 days, about 6 days, about 7 days, about 8 days, about 9 days, about 10 days, about 2 weeks, about 4 weeks, about 6 weeks, about 8 weeks, about 10 weeks, about 12 weeks, about 3 months, about 4 months, about 5 months, about 6 months, about 7 months, about 8 months, about 9 months, about 10 months, about 11 months, or about one year. A formulation disclosed herein can be stable, for example, at about 0° C., about 5° C., about 10° C., about 15° C., about 20° C., about 25° C., about 30° C., about 35° C., about 40° C., about 45° C., about 50° C., about 60° C., about 70° C., or about 80° C. Alcohols.

A non-limiting example of a solubilizing agent includes an organic solvent. Non-limiting examples of organic solvents include alcohols, for example, $C_1$-$C_4$ linear alkyl, $C_3$-$C_4$ branched alkyl, ethanol, ethylene glycol, glycerin, 2-hydroxypropanol, propylene glycol, maltitol, sorbitol, xylitol; substituted or unsubstituted aryl, and benzyl alcohol. Cyclodextrins.

Non-limiting examples of cyclodextrins include β-cyclodextrin, methyl β-cyclodextrin, 2-hydroxypropyl-β-cyclodextrin, sulfobutyl ether-β-cyclodextrin sodium salt, and 2-hydroxypropyl-β-cyclodextirn. A cyclodextrin can possess a large cyclic structure with a channel passing through the center of the structure. The interior of the cyclodextrin can be hydrophobic, and interact favorably with hydrophobic molecules. The exterior of the cyclodextrin can be highly hydrophilic owing to the several hydroxyl groups exposed to bulk solvent. Capture of a hydrophobic molecule, such as a compound disclosed herein, in the channel of the cyclodextrin can result in the formation of a complex stabilized by non-covalent hydrophobic interactions. The complex can be soluble in water, and carry the captured hydrophobic molecule into the bulk solvent.

The disclosed solubilizing systems comprise 2-hydroxypropyl-beta-cyclodextrin (HPβ-CD). 2-Hydroxypropyl-β-cyclodextrin [CAS No. 128446-35-5] is commercially available as Cavitron™. 2-Hydroxypropyl-β-cyclodextrin, also described known as hydroxypropyl-β-cyclodextrin, 2-hydroxypropyl-beta-cyclodextrin, hydroxypropyl-beta-cyclodextrin or HPβCD, can be represented by either of the following formulae:

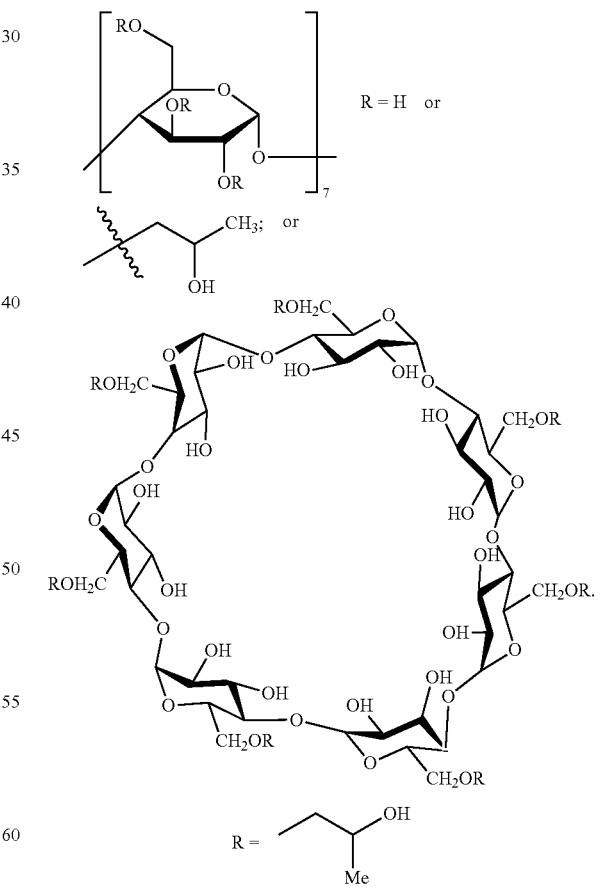

The average molecular weight of Cavitron™, is approximately 1396 Da, wherein the average degree of substitution is from about 0.5 to about 1.3 units of 2-hydroxypropyl per ring glucose unit.

In one embodiment, a formulation disclosed herein can comprise a ratio of about 20 parts of a compound herein or a pharmaceutically acceptable salt thereof to about 1 part solubilizing system (about 20:about 1), to about 1 part of the compound herein or a pharmaceutically acceptable salt thereof to about 20 parts solubilizing system (about 1:about 20). For example, a formulation containing about 100 mg of a compound herein or a pharmaceutically acceptable salt thereof can contain from about 5 mg to about 2000 mg of a solubilizing agent, such as a cyclodextrin. In another embodiment, the ratio can be based on number, or moles, or compound compared to number, or moles, of the solubilizing system.

The following are non-limiting examples of ratios of a compound herein and a solubilizing agent, such as a cyclodextrin. The following examples alternatively describe the ratio of a solubilizing agent, such as a cyclodextrin, and a compound herein. The ratio can be: about 20:about 1; about 19.9:about 1; about 19.8:about 1; about 19.7:about 1; about 19.6: about 1; about 19.5:about 1; about 19.4:about 1; about 19.3:about 1; about 19.2:about 1; about 19.1:about 1; 1:about 19:about 1; about 18.9:about 1; about 18.8:about 1; about 18.7:about 1; about 18.6:about 1; about 18.5:about 1; about 18.4:about 1; about 18.3:about 1; about 18.2:about 1; about 18.1:about 1; about 18:about 1; about 17.9:about 1; about 17.8:about 1; about 17.7:about 1; about 17.6:about 1; about 17.5:about 1; about 17.4:about 1; about 17.3:about 1; about 17.2:about 1; about 17.1:about 1; about 17:about 1; about 16.9:about 1; about 16.8:about 1; about 16.7:about 1; about 16.6:about 1; about 16.5:about 1; about 16.4:about 1; about 16.3:about 1; about 16.2:about 1; about 16.1:about 1; about 16:about 1; about 15.9:about 1; about 15.8:about 1; about 15.7:about 1; about 15.6:about 1; about 15.5:about 1; about 15.4:about 1; about 15.3:about 1; about 15.2:about 1; about 15.1:about 1; about 15:about 1; about 14.9:about 1; about 14.8:about 1; about 14.7:about 1; about 14.6:about 1; about 14.5:about 1; about 14.4:about 1; about 14.3:about 1; about 14.2:about 1; about 14.1:about 1; about 14:about 1; about 13.9:about 1; about 13.8:about 1; about 13.7:about 1; about 13.6:about 1; about 13.5:about 1; about 13.4:about 1; about 13.3:about 1; about 13.2:about 1; about 13.1:about 1; about 13:about 1; about 12.9:about 1; about 12.8:about 1; about 12.7:about 1; about 12.6:about 1; about 12.5:about 1; about 12.4:about 1; about 12.3:about 1; about 12.2:about 1; about 12.1:about 1; about 12:about 1; about 11.9:about 1; about 11.8:about 1; about 11.7:about 1; about 11.6:about 1; about 11.5:about 1; about 11.4:about 1; about 11.3:about 1; about 11.2:about 1; about 11.1:about 1; about 11:about 1; about 10.9:about 1; about 10.8:about 1; about 10.7:about 1; about 10.6:about 1; about 10.5:about about 1; about 10.4:about 1; about 10.3:about 1; about 10.2:about 1; about 10.1:about 1; about 10:about 1; about 9.9:about 1; about 9.8:about 1; about 9.7:about 1; about 9.6:about 1; about 9.5:about 1; about 9.4:about 1; about 9.3:about 1; about 9.2:about 1; about 9.1:about 1; about 9:about 1; about 8.9:about 1; about 8.8:about 1; about 8.7:about 1; about 8.6:about 1; about 8.5:about 1; about 8.4:about 1; about 8.3:about 1; about 8.2:about 1; about 8.1:about 1; about 8:about 1; about 7.9:about 1; about 7.8:about 1; about 7.7:about 1; about 7.6:about 1; about 7.5:about about 1; about 7.4:about 1; about 7.3:about 1; about 7.2:about 1; about 7.1:about 1; about 7:about about 1; about 6.9:about 1; about 6.8:about 1; about 6.7:about 1; about 6.6:about 1; about 6.5:about about 1; about 6.4:about 1; about 6.3:about 1; about 6.2:about 1; about 6.1:about 1; about 6:about 1; about 5.9:about 1; about 5.8:about 1; about 5.7:about 1; about 5.6:about 1; about 5.5:about about 1; about 5.4:about 1; about 5.3:about 1; about 5.2:about 1; about 5.1:about 1; about 5:about 1; about 4.9:about 1; about 4.8:about 1; about 4.7:about 1; about 4.6:about 1; about 4.5:about 1; about 4.4:about 1; about 4.3:about 1; about 4.2:about 1; about 4.1:about 1; about 4:about 1; about 3.9:about 1; about 3.8:about 1; about 3.7:about 1; about 3.6:about 1; about 3.5:about 1; about 3.4:about 1; about 3.3:about 1; about 3.2:about 1; about 3.1:about 1; about 3:about 1; about 2.9:about 1; about 2.8:about 1; about 2.7:about 1; about 2.6:about 1; about 2.5:about 1; about 2.4:about 1; about 2.3:about 1; about 2.2:about 1; about 2.1:about 1; about 2:about 1; about 1.9:about 1; about 1.8:about 1; about 1.7:about 1; about 1.6:about 1; about 1.5:about 1; about 1.4:about 1; about 1.3:about 1; about 1.2:about 1; about 1.1:about 1; or about 1:about 1.

Polyvinylpyrrolidone.

Another non-limiting example of a solubilizing agent is polyvinylpyrrolidone (PVP), having the formula:

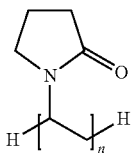

wherein the index n is from about 40 to about 200. PVP's can have an average molecular weight from about 5500 to about 28,000 g/mol. One non-limiting example is PVP-10, having an average molecular weight of approximately 10,000 g/mol.

Polyakyleneoxides and Ethers Thereof.

Another non-limiting example of solubilizing agents includes polyalkyleneoxides, and polymers of alcohols or polyols. Polymers can be mixed, or contain a single monomeric repeat subunit. For example, polyethylene glycols having an average molecular weight of from about 200 to about 20,000, for example, PEG 200, PEG 400, PEG 600, PEG 1000, PEG 1450, PEG 1500, PEG 4000, PEG 4600, and PEG 8000. In a same embodiment, a composition comprises one or more polyethylene glycols chosen from PEG 400, PEG 1000, PEG 1450, PEG 4600 and PEG 8000.

Other polyalkyleneoxides are polypropylene glycols having the formula:

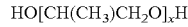

wherein the index x represents the average number of propyleneoxy units in the polymer. The index x can be represented by a whole number or a fraction. For example, a polypropylene glycol having an average molecular weight of 8,000 g/mole (PEG 8000) can be represented by the formulae:

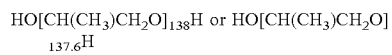

or the polypropylene glycol can be represented by the common, short hand notation: PEG 8000.

Another example of polypropylene glycols can have an average molecular weight from about 1200 g/mol to about 20,000 g/mol, i.e., a polypropylene glycol having an average molecular weight of about 8,000 g/mol, for example, PEG 8000.

Another solubilizing agent is Polysorbate 80 (Tween™ 80), which is an oleate ester of sorbitol and its anhydrides copolymerized with approximately 20 moles of ethylene oxide for each mole of sorbitol and sorbitol anhydrides.

Polysorbate 80 is made up of sorbitan mono-9-octadecanoate poly(oxy-1,2-ethandiyl) derivatives.

Solubilizing agents also include poloxamers having the formula:

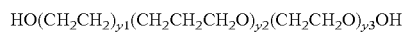

which are nonionic block copolymers composed of a polypropyleneoxy unit flanked by two polyethyleneoxy units. The indices $y^1$, $y^2$, and $y^3$ have values such that the poloxamer has an average molecular weight of from about 1000 g/mol to about 20,000 g/mol.

Excipients.

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, rectal, aerosol, parenteral, ophthalmic, pulmonary, transdermal, vaginal, otic, nasal, and topical administration.

A pharmaceutical composition can be administered in a local or systemic manner, for example, via injection of the compound directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated readily by combining the active compounds with pharmaceutically-acceptable carriers or excipients. Such carriers can be used to formulate tablets, powders, pills, dragees, capsules, liquids, gels, syrups, elixirs, slurries, suspensions and the like, for oral ingestion by a subject.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Cores can be provided with suitable coatings. For this purpose, concentrated sugar solutions can be used, which can contain an excipient such as gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings, for example, for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. A gelatin can be alkaline-processed. The push-fit capsules can contain the active ingredients in admixture with filler such as lactose, binders such as starches, and/or lubricants such as talc or magnesium stearate and, stabilizers. In soft capsules, the active compounds can be dissolved or suspended in suitable liquids, such as fatty oils, liquid paraffin, or liquid polyethylene glycols. Stabilizers can be added. All formulations for oral administration are provided in dosages suitable for such administration.

For buccal or sublingual administration, the compositions can be tablets, lozenges, or gels.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

Formulations suitable for transdermal administration of the active compounds can employ transdermal delivery devices and transdermal delivery patches, and can be lipophilic emulsions or buffered aqueous solutions, dissolved and/or dispersed in a polymer or an adhesive. Such patches can be constructed for continuous, pulsatile, or on demand delivery of pharmaceutical compounds. Transdermal delivery can be accomplished by means of iontophoretic patches. Additionally, transdermal patches can provide controlled delivery. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices can be in the form of a bandage comprising a backing member, a reservoir containing compounds and carriers, a rate controlling barrier to deliver the compounds to the skin of the subject at a controlled and predetermined rate over a prolonged period of time, and adhesives to secure the device to the skin or the eye.

For administration by inhalation, the active compounds can be in a form as an aerosol, a mist, or a powder. Pharmaceutical compositions are conveniently delivered in the form of an aerosol spray presentation from pressurized packs or a nebuliser, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone and PEG. In suppository forms of the compositions, a low-melting wax such as a mixture of fatty acid glycerides or cocoa butter can be used.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compounds described herein can be manufactured, for example, by mixing, dissolving, granulating, dragee-making, levigating, emulsifying, encapsulating, entrapping, or compression processes.

The pharmaceutical compositions can include at least one pharmaceutically acceptable carrier, diluent, or excipient and compounds described herein as free-base or pharmaceutically-acceptable salt form. The methods and pharmaceutical compositions described herein include the use of crystalline forms (also known as polymorphs), and active metabolites of these compounds having the same type of activity.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, cachets, and suppositories. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals, and any combination thereof.

Non-limiting examples of pharmaceutically-acceptable excipients suitable for use in the invention include granulating agents, binding agents, lubricating agents, disintegrating agents, sweetening agents, glidants, anti-adherents, antistatic agents, surfactants, anti-oxidants, gums, coating agents, coloring agents, flavouring agents, coating agents, plasticizers, preservatives, suspending agents, emulsifying agents, anti-microbial agents, plant cellulosic material and spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that drug release rates and drug release profiles can be matched to physiological and chronotherapeutic requirements or, alternatively, has been formulated to effect release of a drug at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

The disclosed compositions can optionally comprise from about 0.001% to about 0.005% weight by volume pharmaceutically acceptable preservatives. One non-limiting example of a suitable preservative is benzyl alcohol.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), each of which is incorporated by reference in its entirety.

The disclosed methods include administration of a HPTPβ inhibitor, or a pharmaceutically acceptable salt thereof, in combination with a pharmaceutically acceptable carrier. The carrier can be selected to minimize any degradation of the active ingredient and to minimize any adverse side effects in the subject.

The HPTPβ inhibitor or a pharmaceutically acceptable salt thereof herein can be conveniently formulated into pharmaceutical compositions composed of one or more pharmaceutically acceptable carriers. See e.g., *Remington's*

*Pharmaceutical Sciences*, latest edition, by E. W. Martin Mack Pub. Co., Easton, Pa., which discloses typical carriers and conventional methods of preparing pharmaceutical compositions that can be used in conjunction with the preparation of formulations of the compound described herein and which is incorporated by reference herein. Such pharmaceuticals can be standard carriers for administration of compositions to humans and non-humans, including solutions such as sterile water, saline, and buffered solutions at physiological pH. Other compositions can be administered according to standard procedures. For example, pharmaceutical compositions can also include one or more additional active ingredients such as antimicrobial agents, anti-inflammatory agents, and anesthetics.

Non-limiting examples of pharmaceutically-acceptable carriers include, but are not limited to, saline, Ringer's solution and dextrose solution. The pH of the solution can be from about 5 to about 8, and can be from about 7 to about 7.5. Further carriers include sustained release preparations such as semipermeable matrices of solid hydrophobic polymers containing the HPTPβ inhibitor or a pharmaceutically-acceptable salt thereof, where the matrices are in the form of shaped articles, e.g., films, liposomes, microparticles, or microcapsules.

The disclosed methods relate to administering the HPTPβ inhibitor or a pharmaceutically acceptable salt thereof as part of a pharmaceutical composition. In various embodiments, compositions of the invention can comprise a liquid comprising an active agent in solution, in suspension, or both. Liquid compositions can include gels. In one embodiment, the liquid composition is aqueous. Alternatively, the composition can take form of an ointment. In another embodiment, the composition is an in situ gellable aqueous composition. In some embodiments, the composition is an in situ gellable aqueous solution.

Pharmaceutical formulations can include additional carriers, as well as thickeners, diluents, buffers, preservatives, and surface active agents in addition to the compounds disclosed herein. Pharmaceutical formulations can also include one or more additional active ingredients such as antimicrobial agents, anti-inflammatory agents, anesthetics, and the like.

An excipient can fill a role as simple and direct as being an inert filler, or an excipient as used herein can be part of a pH stabilizing system or coating to insure delivery of the ingredients safely to the stomach.

The HPTPβ inhibitor or a pharmaceutically-acceptable salt thereof can also be present in liquids, emulsions, or suspensions for delivery of active therapeutic agents in aerosol form to cavities of the body such as the nose, throat, or bronchial passages. The ratio of HPTPβ inhibitor or a pharmaceutically-acceptable salt thereof to the other compounding agents in these preparations can vary as the dosage form requires.

Depending on the intended mode of administration, the pharmaceutical compositions administered as part of the disclosed methods can be in the form of solid, semi-solid or liquid dosage forms, such as, for example, tablets, suppositories, pills, capsules, powders, liquids, suspensions, lotions, creams, gels, or the like, for example, in unit dosage form suitable for single administration of a precise dosage. The compositions can contain, as noted above, an effective amount of the HPTPβ inhibitor or a pharmaceutically-acceptable salt thereof in combination with a pharmaceutically-acceptable carrier and, in addition, can include other medicinal agents, pharmaceutical agents, carriers, adjuvants, diluents, etc.

For solid compositions, nontoxic solid carriers include, for example, pharmaceutical grades of mannitol, lactose, starch, magnesium stearate, sodium saccharin, talc, cellulose, glucose, sucrose, and magnesium carbonate. In one embodiment, a composition comprising the HPTPβ inhibitor or a pharmaceutically acceptable salt thereof in an amount of approximately 4 mg per 0.1 mL liquid is prepared. The liquid phase comprises sterile water and an appropriate amount of a saccharide or polysaccharide.

Pharmaceutical Compositions.

Pharmaceutical compositions containing the compounds described herein can be administered for prophylactic and/or therapeutic treatments. Compositions can contain any number of active agents, including a Tie-2 activator in combination with any number of checkpoint modulators, such as 1, 2, 3, 4, 5, 6, 7, 8, 9, or 10 checkpoint modulators. In therapeutic applications, the compositions can be administered to a subject already suffering from a disease or condition, in an amount sufficient to cure or at least partially arrest the symptoms of the disease or condition, or to cure, heal, improve, reduce, lessen or ameliorate the disease or condition. Compounds can also be administered to lessen or reduce a likelihood of developing, contracting, or worsening a condition. Amounts effective for this use can vary based on the severity and course of the disease or condition, previous therapy, the subject's health status, weight, response to the drugs, and the judgment of the treating physician.

Multiple therapeutic agents can be administered in any order or simultaneously. If simultaneously, the multiple therapeutic agents can be provided in a single, unified form, or in multiple forms, for example, as multiple separate pills or injections. The compounds can be packed together or separately, in a single package or in a plurality of packages. One or all of the therapeutic agents can be given in multiple doses. If not simultaneous, the timing between the multiple doses can vary.

Compounds and compositions of the invention can be packaged as a kit. In some embodiments, the invention provides a kit comprising a compound disclosed herein, or a pharmaceutically-acceptable salt thereof, and written instructions on use of the kit in the treatment of a condition described herein. In some embodiments, the invention provides a kit comprising a compound disclosed herein, or a pharmaceutically-acceptable salt thereof, an antibody, and written instructions on use of the kit in the treatment of a condition described herein.

The compounds described herein can be administered before, during, or after the occurrence of a disease or condition, and the timing of administering the composition containing a compound can vary. For example, the compounds can be used as a prophylactic and can be administered continuously to subjects with a propensity to conditions or diseases in order to lessen or reduce a likelihood of the occurrence of the disease or condition. The compounds and compositions can be administered to a subject during or as soon as possible after the onset of the symptoms. The administration of the compounds can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein.

A compound can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for parenteral injection can be presented in unit dosage form, for example, in ampoules, or in multi-dose containers with a preservative.

A compound described herein can be present in a composition in a range of from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, from about 30 mg to about 35 mg, from about 35 mg to about 40 mg, from about 40 mg to about 45 mg, from about 45 mg to about 50 mg, from about 50 mg to about 55 mg, from about 55 mg to about 60 mg, from about 60 mg to about 65 mg, from about 65 mg to about 70 mg, from about 70 mg to about 75 mg, from about 75 mg to about 80 mg, from about 80 mg to about 85 mg, from about 85 mg to about 90 mg, from about 90 mg to about 95 mg, from about 95 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, or from about 250 mg to about 300 mg.

A compound described herein can be present in a composition in an amount of about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 225 mg, about 250 mg, or about 300 mg.

Combination Treatment of Subjects with an Immunotherapy or Oncolytic Virus Therapy.

The invention discloses methods for treating a subject with a combination of an immunotherapy or an oncolytic virus (OV) therapy and an activator of Tie-2. A method of the invention can also comprise treating a subject afflicted with a cancer with an activator of Tie-2, an immunotherapy or OV therapy, and a distinct modality of treatment, such as radiation, chemotherapy, targeted therapy, or surgery. The subject can be a human. Treatment can include treating a human in a clinical trial. A treatment can comprise administering to a subject a pharmaceutical composition comprising one or more of the activators or Tie-2 and immunotherapies or OV therapies described throughout the disclosure. A treatment can comprise administrating to a subject a combination therapy that promotes the phosphorylation of a Tie-2 molecule and inhibits a checkpoint molecule or induces cancer cell viral lysis.

In some embodiments, the invention provides a combination of a Tie-2 activator and a modulator of an immune checkpoint molecule or OV for use in treatment of cancer. In some embodiments, the invention provides a pharmaceutical composition comprising a therapeutically-effective amount of a Tie-2 activator and a therapeutically-effective amount of a modulator of an immune checkpoint molecule or OV for use in treatment of cancer. In some embodiments, the invention provides a combination of a Tie-2 activator a modulator of an immune checkpoint molecule or OV for use in the manufacture of a medicament for the treatment of cancer.

In some embodiments, the invention provides a Tie-2 activator for use in treatment of cancer. In some embodiments, the invention provides a HPTPβ inhibitor for use in treatment of cancer. In some embodiments, the invention provides a Tie-2 activator for use in the manufacture of a medicament for the treatment of cancer. In some embodiments, the invention provides a HPTPβ inhibitor for use in the manufacture of a medicament for the treatment of cancer.

Non-limiting examples of possible subjects for administration include the following. Subjects can be humans, non-human primates such as chimpanzees, and other apes and monkey species; farm animals such as cattle, horses, sheep, goats, and swine; domestic animals such as rabbits, dogs, and cats; and laboratory animals including rats, mice, and guinea pigs. A subject can be of any age. Subjects can be, for example, elderly adults, adults, adolescents, pre-adolescents, children, toddlers, and infants.

Components of combination therapies described herein can be administered concomitantly or sequentially. An activator of Tie-2 can be administered at least 1 hour, at least 6 hours, at least 12 hours, at least 24 hours, at least 48 hours, at least 72 hours, at least 96 hours, at least 1 week, at least 2 weeks, at least 3 weeks, at least 4 weeks, at least 1 month, at least 2 months, at least 3 months, at least 4 months, at least 5 months, or at least 6 months before the administration of an immunotherapy or OV therapy. An immunotherapy or OV therapy of the disclosure can be administered at least 1 hour, at least 6 hours, at least 12 hours, at least 24 hours, at least 48 hours, at least 72 hours, at least 96 hours, at least 1 week, at least 2 weeks, at least 3 weeks, at least 4 weeks, at least 1 month, at least 2 months, at least 3 months, at least 4 months, at least 5 months, or at least 6 months before the administration of an activator of Tie-2.

In some embodiments, an activator of Tie-2 can be administered at most 1 hour, at most 6 hours, at most 12 hours, at most 24 hours, at most 48 hours, at most 72 hours, at most 96 hours, at most 1 week, at most 2 weeks, at most 3 weeks, at most 4 weeks, at most 1 month, at most 2 months, at most 3 months, at most 4 months, at most 5 months, or at most 6 months before the administration of an immunotherapy or OV therapy. An immunotherapy or OV therapy of the disclosure can be administered at most 1 hour, at most 6 hours, at most 12 hours, at most 24 hours, at most 48 hours, at most 72 hours, at most 96 hours, at most 1 week, at most 2 weeks, at most 3 weeks, at most 4 weeks, at most 1 month, at most 2 months, at most 3 months, at most 4 months, at most 5 months, or at most 6 months before the administration of an activator of Tie-2.

Some conditions, including some cancers, can lead to an increase in the levels of Ang-2, altering the ratio of Ang-1/Ang-2 in circulation. In some aspects, a combination therapy can improve the outcome of a cancer by altering the ratio of Ang-1/Ang-2 in circulation. A combination therapy can provide an Ang-1/Ang-2 ratio or an Ang-2/Ang-1 ratio of about 1:about 1, about 2:about 1, about 3:about 1, about 4:about 1, about 5:about 1, about 6:about 1, about 7:about 1, about 8:about 1, about 9:about 1, or about 10:about 1.

In some embodiments the cancer is melanoma. In some embodiments the cancer is renal cell carcinoma. Non-limiting examples of cancers include: acute lymphoblastic leukemia, acute myeloid leukemia, adrenocortical carcinoma, AIDS-related cancers, AIDS-related lymphoma, anal cancer, appendix cancer, astrocytomas, neuroblastoma, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell cancer, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

In some embodiments, administration of the Tie-2 activator to the subject reduces a toxicity of an immunotherapy or OV therapy. In some embodiments, the Tie-2 activator reduces the toxicity of an immunotherapy or OV therapy by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%. In some embodiments, the activator of Tie-2 reduces the toxicity of an immunotherapy by at most about 1%, at most about 5%, at most about 10%, at most about 15%, at most about 20%, at most about 25%, at most about 30%, at most about 35%, at most about 40%, at most about 45%, at most about 50%, at most about 55%, at most about 60%, at most about 65%, at most about 70%, at most about 75%, at most about 80%, at most about 85%, at most about 90%, at most about 95%, or at most about 99%.

Pharmacodynamic and Pharmacokinetic Parameters.

Pharmacokinetic and pharmacodynamic data can be obtained by various experimental techniques. Appropriate pharmacokinetic and pharmacodynamic profile components describing a particular composition can vary due to variations in the metabolism of an immunotherapy or OV therapy or an activator of Tie-2 in different subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean is determined by calculating the average of all subject's measurements for each parameter measured.

A combination therapy can be used to inhibit a specific biological or biochemical function at a lower dosage. A dose can be modulated to achieve a desired pharmacokinetic or pharmacodynamics profile, such as a desired or effective blood profile, as described herein. The half maximum inhibitory concentration ($IC_{50}$) is a measure of the effectiveness of a substance in inhibiting a specific biological or biochemical function. This quantitative measure indicates how much of a particular drug or compound is needed to inhibit a given biological process, such as the activity of HPTPβ, PD-1 or CTLA4 by half. Combination drug treatments can present lower $IC_{50}$ values as compared to monotherapies.

The outcome of treating a human subject with a combination therapy can be measured by calculating pharmacodynamic and pharmacokinetic parameters. Non-limiting examples of pharmacodynamic and pharmacokinetic parameters that can be used to determine the effect of treatment of a subject with a combination therapy of the disclosure include: a) the amount of drug administered, which can be represented as a dose D; b) the dosing interval, which can be represented as τ; c) the apparent volume in which a drug is distributed, which can be represented as a volume of distribution $V_d$, where $V_d = D/C_0$; d) the amount of drug in a given volume of plasma, which can be represented as concentration $C_0$ or $C_{ss}$, where $C_0$ or $C_{ss} = D/Vd$; e) the half-life of a drug $t_{1/2}$, where $t_{1/2} = \ln(2)/k_e$; f) the rate at which a drug is removed from the body $k_e$, where $k_e = \ln(2)/t_{1/2} = CL/V_d$; g) the rate of infusion required to balance the equation $K_{in}$, where $K_{in} = C_{ss}$, CL; h) the integral of the concentration-time curve after administration of a single dose, which can be represented as $AUC_{0-\infty}$, wherein $\int_0^\infty C\, dt$, or in steady-state, which can be represented as $AUC\tau_{,ss}$, wherein $\int_t^{t+\tau} C\, dt$; i)

the volume of plasma cleared of the drug per unit time, which can be represented as CL (clearance), wherein $CL = V_d \cdot k_e = D/AUC$; j) the systemically available fraction of a drug, which can be represented as f, where $$f = \frac{AUCpo \cdot Div}{AUCiv \cdot Dpo}; k)$$

the peak plasma concentration of a drug after administration $C_{max}$; l) the time taken by a drug to reach $C_{max}$, $t_{max}$; m) the lowest concentration that a drug reaches before the next dose is administered $C_{min}$; and n) the peak trough fluctuation within one dosing interval at steady state, which can be represented as $$\%PTF = 100 \cdot \frac{(Cmax, ss - Cmin, ss)}{Cav, ss}$$

where $$C_{av,ss} = \frac{AUC\tau, ss}{\tau}.$$

The pharmacokinetics parameters can be any parameters suitable for describing the plasma profiles of a combination therapy of the disclosure. For example, the pharmacokinetics profile can be obtained at a time after dosing of, for example, about zero minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about zero hours, about 0.5 hours, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or about 24 hours.

The pharmacokinetic parameters can be any parameters suitable for describing an immunotherapy. The $C_{max}$ can be, for example, not less than about 1 μg/mL; not less than about 5 μg/mL; not less than about 10 μg/mL; not less than about 15 μg/mL; not less than about 20 μg/mL; not less than about 25 μg/mL; not less than about 50 μg/mL; not less than about 75 μg/mL; not less than about 100 μg/mL; not less than about 200 μg/mL; not less than about 300 μg/mL; not less than about 400 μg/mL; not less than about 500 μg/mL; not less than about 600 μg/mL; not less than about 700 μg/mL; not less than about 800 μg/mL; not less than about 900 μg/mL; not less than about 1000 μg/mL; not less than about 1250 μg/mL; not less than about 1500 μg/mL; not less than about 1750 μg/mL; not less than about 2000 μg/mL; or any other $C_{max}$ appropriate for describing a pharmacokinetic profile of an immunotherapy described herein. The $C_{max}$ can be, for example, about 1 μg/mL to about 5,000 μg/mL; about 1 μg/mL to about 4,500 μg/mL; about 1 μg/mL to about 4,000 μg/mL; about 1 μg/mL to about 3,500 μg/mL; about 1 μg/mL to about 3,000 μg/mL; about 1 μg/mL to about 2,500 μg/mL; about 1 μg/mL to about 2,000 μg/mL; about 1 μg/mL to about 1,500 μg/mL; about 1 μg/mL to about 1,000 μg/mL; about 1 μg/mL to about 900 μg/mL; about 1 μg/mL to about 800 μg/mL; about 1 μg/mL to about 700 μg/mL; about 1 μg/mL to about 600 μg/mL; about 1 μg/mL to about 500 μg/mL; about 1 μg/mL to about 450 μg/mL; about 1 μg/mL to about 400 μg/mL; about 1 μg/mL to about 350 μg/mL; about 1 μg/mL to about 300 μg/mL; about 1 μg/mL to about 250 μg/mL; about 1 μg/mL to about 200 μg/mL; about 1 μg/mL to about 150 μg/mL; about 1 μg/mL to about 125 μg/mL; about 1 μg/mL to about 100 μg/mL; about 1 μg/mL to about 90 μg/mL; about 1 μg/mL to about 80 μg/mL; about 1 μg/mL to about 70 μg/mL; about 1 μg/mL to about 60 μg/mL; about 1 μg/mL to about 50 μg/mL; about 1 μg/mL to about 40 μg/mL; about 1 μg/mL to about 30 μg/mL; about 1 μg/mL to about 20 μg/mL; about 1 μg/mL to about 10 μg/mL; about 1 μg/mL to about 5 μg/mL; about 10 μg/mL to about 4,000 μg/mL; about 10 μg/mL to about 3,000 μg/mL; about 10 μg/mL to about 2,000 μg/mL; about 10 μg/mL to about 1,500 μg/mL; about 10 μg/mL to about 1,000 μg/mL; about 10 μg/mL to about 900 μg/mL; about 10 μg/mL to about 800 μg/mL; about 10 μg/mL to about 700 μg/mL; about 10 μg/mL to about 600 μg/mL; about 10 μg/mL to about 500 μg/mL; about 10 μg/mL to about 400 μg/mL; about 10 μg/mL to about 300 μg/mL; about 10 μg/mL to about 200 μg/mL; about 10 μg/mL to about 100 μg/mL; about 10 μg/mL to about 50 μg/mL; about 25 μg/mL to about 500 μg/mL; about 25 μg/mL to about 100 μg/mL; about 50 μg/mL to about 500 μg/mL; about 50 μg/mL to about 100 μg/mL; about 100 μg/mL to about 500 μg/mL; about 100 μg/mL to about 400 μg/mL; about 100 μg/mL to about 300 μg/mL; or about 100 μg/mL to about 200 μg/mL.

The pharmacokinetic parameters can be any parameters suitable for describing a small molecule activator of Tie-2. The $C_{max}$ can be, for example, not less than about 1 ng/mL; not less than about 5 ng/mL; not less than about 10 ng/mL; not less than about 15 ng/mL; not less than about 20 ng/mL; not less than about 25 ng/mL; not less than about 50 ng/mL; not less than about 75 ng/mL; not less than about 100 ng/mL; not less than about 200 ng/mL; not less than about 300 ng/mL; not less than about 400 ng/mL; not less than about 500 ng/mL; not less than about 600 ng/mL; not less than about 700 ng/mL; not less than about 800 ng/mL; not less than about 900 ng/mL; not less than about 1000 ng/mL; not less than about 1250 ng/mL; not less than about 1500 ng/mL; not less than about 1750 ng/mL; not less than about 2000 ng/mL; or any other $C_{max}$ appropriate for describing a pharmacokinetic profile of an activator of Tie-2 described herein. The $C_{max}$ can be, for example, about 1 ng/mL to about 5,000 ng/mL; about 1 ng/mL to about 4,500 ng/mL; about 1 ng/mL to about 4,000 ng/mL; about 1 ng/mL to about 3,500 ng/mL; about 1 ng/mL to about 3,000 ng/mL; about 1 ng/mL to about 2,500 ng/mL; about 1 ng/mL to about 2,000 ng/mL; about 1 ng/mL to about 1,500 ng/mL; about 1 ng/mL to about 1,000 ng/mL; about 1 ng/mL to about 900 ng/mL; about 1 ng/mL to about 800 ng/mL; about 1 ng/mL to about 700 ng/mL; about 1 ng/mL to about 600 ng/mL; about 1 ng/mL to about 500 ng/mL; about 1 ng/mL to about 450 ng/mL; about 1 ng/mL to about 400 ng/mL; about 1 ng/mL to about 350 ng/mL; about 1 ng/mL to about 300 ng/mL; about 1 ng/mL to about 250 ng/mL; about 1 ng/mL to about 200 ng/mL; about 1 ng/mL to about 150 ng/mL; about 1 ng/mL to about 125 ng/mL; about 1 ng/mL to about 100 ng/mL; about 1 ng/mL to about 90 ng/mL; about 1 ng/mL to about 80 ng/mL; about 1 ng/mL to about 70 ng/mL; about 1 ng/mL to about 60 ng/mL; about 1 ng/mL to about 50 ng/mL; about 1 ng/mL to about 40 ng/mL; about 1 ng/mL to about 30 ng/mL; about 1 ng/mL to about 20 ng/mL; about 1 ng/mL to about 10 ng/mL; about 1 ng/mL to about 5 ng/mL; about 10 ng/mL to about 4,000 ng/mL; about 10 ng/mL to about 3,000 ng/mL; about 10 ng/mL to about 2,000 ng/mL; about 10 ng/mL to about 1,500 ng/mL; about 10 ng/mL to about 1,000 ng/mL; about 10 ng/mL to about 900 ng/mL; about 10 ng/mL to about 800 ng/mL; about 10 ng/mL to about 700 ng/mL; about 10 ng/mL to about 600 ng/mL; about 10 ng/mL to about 500 ng/mL; about 10 ng/mL to about 400 ng/mL; about 10 ng/mL to about 300 ng/mL; about 10 ng/mL to about 200 ng/mL; about 10 ng/mL to about 100 ng/mL; about 10 ng/mL to about 50 ng/mL; about 25 ng/mL to about 500 ng/mL; about 25 ng/mL to about 100 ng/mL; about 50 ng/mL to about 500 ng/mL; about 50 ng/mL to about 100 ng/mL; about 100 ng/mL to about 500 ng/mL; about 100 ng/mL to about 400 ng/mL; about 100 ng/mL to about 300 ng/mL; or about 100 ng/mL to about 200 ng/mL.

The $T_{max}$ of an immunotherapy, OV therapy, or an activator of Tie-2 described herein can be, for example, not greater than about 0.5 hours, not greater than about 1 hours, not greater than about 1.5 hours, not greater than about 2 hours, not greater than about 2.5 hours, not greater than about 3 hours, not greater than about 3.5 hours, not greater than about 4 hours, not greater than about 4.5 hours, not greater than about 5 hours, or any other $T_{max}$ appropriate for describing a pharmacokinetic profile of an immunotherapy or an activator of Tie-2 described herein. The $T_{max}$ can be, for example, about 0.1 hours to about 24 hours; about 0.1 hours to about 0.5 hours; about 0.5 hours to about 1 hour; about 1 hour to about 1.5 hours; about 1.5 hours to about 2 hour; about 2 hours to about 2.5 hours; about 2.5 hours to about 3 hours; about 3 hours to about 3.5 hours; about 3.5 hours to about 4 hours; about 4 hours to about 4.5 hours; about 4.5 hours to about 5 hours; about 5 hours to about 5.5 hours; about 5.5 hours to about 6 hours; about 6 hours to about 6.5 hours; about 6.5 hours to about 7 hours; about 7 hours to about 7.5 hours; about 7.5 hours to about 8 hours; about 8 hours to about 8.5 hours; about 8.5 hours to about 9 hours; about 9 hours to about 9.5 hours; about 9.5 hours to about 10 hours; about 10 hours to about 10.5 hours; about 10.5 hours to about 11 hours; about 11 hours to about 11.5 hours; about 11.5 hours to about 12 hours; about 12 hours to about 12.5 hours; about 12.5 hours to about 13 hours; about 13 hours to about 13.5 hours; about 13.5 hours to about 14 hours; about 14 hours to about 14.5 hours; about 14.5 hours to about 15 hours; about 15 hours to about 15.5 hours; about 15.5 hours to about 16 hours; about 16 hours to about 16.5 hours; about 16.5 hours to about 17 hours; about 17 hours to about 17.5 hours; about 17.5 hours to about 18 hours; about 18 hours to about 18.5 hours; about 18.5 hours to about 19 hours; about 19 hours to about 19.5 hours; about 19.5 hours to about 20 hours; about 20 hours to about 20.5 hours; about 20.5 hours to about 21 hours; about 21 hours to about 21.5 hours; about 21.5 hours to about 22 hours; about 22 hours to about 22.5 hours; about 22.5 hours to about 23 hours; about 23 hours to about 23.5 hours; or about 23.5 hours to about 24 hours.

The $AUC_{(0-inf)}$ of an activator of Tie-2 described herein can be, for example, not less than about 1 ng·hr/mL, not less than about 5 ng·hr/mL, not less than about 10 ng·hr/mL, not less than about 20 ng·hr/mL, not less than about 30 ng·hr/mL, not less than about 40 ng·hr/mL, not less than about 50 ng·hr/mL, not less than about 100 ng·hr/mL, not less than about 150 ng·hr/mL, not less than about 200 ng·hr/mL, not less than about 250 ng·hr/mL, not less than about 300 ng·hr/mL, not less than about 350 ng·hr/mL, not less than about 400 ng·hr/mL, not less than about 450 ng·hr/mL, not less than about 500 ng·hr/mL, not less than about 600 ng·hr/mL, not less than about 700 ng·hr/mL, not less than about 800 ng·hr/mL, not less than about 900 ng·hr/mL, not less than about 1000 ng·hr/mL, not less than about 1250 ng·hr/mL, not less than about 1500 ng·hr/mL, not less than about 1750 ng·hr/mL, not less than about 2000 ng·hr/mL, not less than about 2500 ng·hr/mL, not less than about 3000 ng·hr/mL, not less than about 3500 ng·hr/mL, not less than about 4000 ng·hr/mL, not less than about 5000 ng·hr/mL, not less than about 6000 ng·hr/mL, not less than about 7000 ng·hr/mL, not less than about 8000 ng·hr/mL, not less than about 9000 ng·hr/mL, not less than about 10,000 ng·hr/mL, or any other $AUC_{(0-inf)}$ appropriate for describing a pharmacokinetic profile of a compound described herein. The $AUC_{(0-inf)}$ of an activator of Tie-2 can be, for example, about 1 ng·hr/mL to about 10,000 ng·hr/mL; about 1 ng·hr/mL to about 10 ng·hr/mL; about 10 ng·hr/mL to about 25 ng·hr/mL; about 25 ng·hr/mL to about 50 ng·hr/mL; about 50 ng·hr/mL to about 100 ng·hr/mL; about 100 ng·hr/mL to about 200 ng·hr/mL; about 200 ng·hr/mL to about 300 ng·hr/mL; about 300 ng·hr/mL to about 400 ng·hr/mL; about 400 ng·hr/mL to about 500 ng·hr/mL; about 500 ng·hr/mL to about 600 ng·hr/mL; about 600 ng·hr/mL to about 700 ng·hr/mL; about 700 ng·hr/mL to about 800 ng·hr/mL; about 800 ng·hr/mL to about 900 ng·hr/mL; about 900 ng·hr/mL to about 1,000 ng·hr/mL; about 1,000 ng·hr/mL to about 1,250 ng·hr/mL; about 1,250 ng·hr/mL to about 1,500 ng·hr/mL; about 1,500 ng·hr/mL to about 1,750 ng·hr/mL; about 1,750 ng·hr/mL to about 2,000 ng·hr/mL; about 2,000 ng·hr/mL to about 2,500 ng·hr/mL; about 2,500 ng·hr/mL to about 3,000 ng·hr/mL; about 3,000 ng·hr/mL to about 3,500 ng·hr/mL; about 3,500 ng·hr/mL to about 4,000 ng·hr/mL; about 4,000 ng·hr/mL to about 4,500 ng·hr/mL; about 4,500 ng·hr/mL to about 5,000 ng·hr/mL; about 5,000 ng·hr/mL to about 5,500 ng·hr/mL; about 5,500 ng·hr/mL to about 6,000 ng·hr/mL; about 6,000 ng·hr/mL to about 6,500 ng·hr/mL; about 6,500 ng·hr/mL to about 7,000 ng·hr/mL; about 7,000 ng·hr/mL to about 7,500 ng·hr/mL; about 7,500 ng·hr/mL to about 8,000 ng·hr/mL; about 8,000 ng·hr/mL to about 8,500 ng·hr/mL; about 8,500 ng·hr/mL to about 9,000 ng·hr/mL; about 9,000 ng·hr/mL to about 9,500 ng·hr/mL; or about 9,500 ng·hr/mL to about 10,000 ng·hr/mL.

The $AUC_{(0-inf)}$ of an immunotherapy or OV therapy described herein can be, for example, not less than about 100 µg·hr/mL, not less than about 125 µg·hr/mL, not less than about 150 µg·hr/mL, not less than about 175 µg·hr/mL, not less than about 200 µg·hr/mL, not less than about 250 µg·hr/mL, not less than about 300 µg·hr/mL, not less than about 350 µg·hr/mL, not less than about 400 µg·hr/mL, not less than about 500 µg·hr/mL, not less than about 600

µg·hr/mL, not less than about 700 µg·hr/mL, not less than about 800 µg·hr/mL, not less than about 900 µg·hr/mL, not less than about 1000 µg·hr/mL, not less than about 2000 µg·hr/mL, not less than about 3000 µg·hr/mL, not less than about 4000 µg·hr/mL, not less than about 5000 µg·hr/mL, not less than about 6000 µg·hr/mL, not less than about 7000 µg·hr/mL, not less than about 8000 µg·hr/mL, not less than about 9000 µg·hr/mL, not less than about 10000 µg·hr/mL, not less than about 11000 µg·hr/mL, not less than about 12000 µg·hr/mL, not less than about 13000 µg·hr/mL, not less than about 14000 µg·hr/mL, not less than about 15000 µg·hr/mL, not less than about 16000 µg·hr/mL, not less than about 17000 µg·hr/mL, not less than about 18000 µg·hr/mL, not less than about 19000 µg·hr/mL, not less than about 20000 µg·hr/mL, not less than about 21000 µg·hr/mL, not less than about 22000 µg·hr/mL, not less than about 23000 µg·hr/mL, not less than about 24000 µg·hr/mL, not less than about 25000 µg·hr/mL, not less than about 26000 µg·hr/mL, not less than about 27000 µg·hr/mL, not less than about 28000 µg·hr/mL, not less than about 29000 µg·hr/mL, not less than about 30000 µg·hr/mL, not less than about 31000 µg·hr/mL, not less than about 32000 µg·hr/mL, not less than about 33000 µg·hr/mL, not less than about 34000 µg·hr/mL, not less than about 35000 µg·hr/mL, or any other $AUC_{(0-inf)}$ appropriate for describing a pharmacokinetic profile of an immunotherapy described herein. The $AUC_{(0-inf)}$ of an immunotherapy can be, for example, about 1 µg·hr/mL to about 10,000 µg·hr/mL; about 1 µg·hr/mL to about 10 µg·hr/mL; about 10 µg·hr/mL to about 25 µg·hr/mL; about 25 µg·hr/mL to about 50 µg·hr/mL; about 50 µg·hr/mL to about 100 µg·hr/mL; about 100 µg·hr/mL to about 200 µg·hr/mL; about 200 µg·hr/mL to about 300 µg·hr/mL; about 300 µg·hr/mL to about 400 µg·hr/mL; about 400 µg·hr/mL to about 500 µg·hr/mL; about 500 µg·hr/mL to about 600 µg·hr/mL; about 600 µg·hr/mL to about 700 µg·hr/mL; about 700 µg·hr/mL to about 800 µg·hr/mL; about 800 µg·hr/mL to about 900 µg·hr/mL; about 900 µg·hr/mL to about 1,000 µg·hr/mL; about 1,000 µg·hr/mL to about 1,250 µg·hr/mL; about 1,250 µg·hr/mL to about 1,500 µg·hr/mL; about 1,500 µg·hr/mL to about 1,750 µg·hr/mL; about 1,750 µg·hr/mL to about 2,000 µg·hr/mL; about 2,000 µg·hr/mL to about 2,500 µg·hr/mL; about 2,500 µg·hr/mL to about 3,000 µg·hr/mL; about 3,000 µg·hr/mL to about 3,500 µg·hr/mL; about 3,500 µg·hr/mL to about 4,000 µg·hr/mL; about 4,000 µg·hr/mL to about 4,500 µg·hr/mL; about 4,500 µg·hr/mL to about 5,000 µg·hr/mL; about 5,000 µg·hr/mL to about 5,500 µg·hr/mL; about 5,500 µg·hr/mL to about 6,000 µg·hr/mL; about 6,000 µg·hr/mL to about 6,500 µg·hr/mL; about 6,500 µg·hr/mL to about 7,000 µg·hr/mL; about 7,000 µg·hr/mL to about 7,500 µg·hr/mL; about 7,500 µg·hr/mL to about 8,000 µg·hr/mL; about 8,000 µg·hr/mL to about 8,500 µg·hr/mL; about 8,500 µg·hr/mL to about 9,000 µg·hr/mL; about 9,000 µg·hr/mL to about 9,500 µg·hr/mL; or about 9,500 µg·hr/mL to about 10,000 µg·hr/mL.

The plasma concentration of an activator of Tie-2 described herein can be, for example, not less than about 1 ng/mL, not less than about 5 ng/mL, not less than about 10 ng/mL, not less than about 15 ng/mL, not less than about 20 ng/mL, not less than about 25 ng/mL, not less than about 50 ng/mL, not less than about 75 ng/mL, not less than about 100 ng/mL, not less than about 150 ng/mL, not less than about 200 ng/mL, not less than about 300 ng/mL, not less than about 400 ng/mL, not less than about 500 ng/mL, not less than about 600 ng/mL, not less than about 700 ng/mL, not less than about 800 ng/mL, not less than about 900 ng/mL, not less than about 1000 ng/mL, not less than about 1200 ng/mL, or any other plasma concentration of an activator of Tie-2 described herein. The plasma concentration can be, for example, about 1 ng/mL to about 2,000 ng/mL; about 1 ng/mL to about 5 ng/mL; about 5 ng/mL to about 10 ng/mL; about 10 ng/mL to about 25 ng/mL; about 25 ng/mL to about 50 ng/mL; about 50 ng/mL to about 75 ng/mL; about 75 ng/mL to about 100 ng/mL; about 100 ng/mL to about 150 ng/mL; about 150 ng/mL to about 200 ng/mL; about 200 ng/mL to about 250 ng/mL; about 250 ng/mL to about 300 ng/mL; about 300 ng/mL to about 350 ng/mL; about 350 ng/mL to about 400 ng/mL; about 400 ng/mL to about 450 ng/mL; about 450 ng/mL to about 500 ng/mL; about 500 ng/mL to about 600 ng/mL; about 600 ng/mL to about 700 ng/mL; about 700 ng/mL to about 800 ng/mL; about 800 ng/mL to about 900 ng/mL; about 900 ng/mL to about 1,000 ng/mL; about 1,000 ng/mL to about 1,100 ng/mL; about 1,100 ng/mL to about 1,200 ng/mL; about 1,200 ng/mL to about 1,300 ng/mL; about 1,300 ng/mL to about 1,400 ng/mL; about 1,400 ng/mL to about 1,500 ng/mL; about 1,500 ng/mL to about 1,600 ng/mL; about 1,600 ng/mL to about 1,700 ng/mL; about 1,700 ng/mL to about 1,800 ng/mL; about 1,800 ng/mL to about 1,900 ng/mL; or about 1,900 ng/mL to about 2,000 ng/mL.

The plasma concentration of an immunotherapy described herein can be, for example, not less than about 1 µg/mL, not less than about 2 µg/mL, not less than about 3 µg/mL, not less than about 4 µg/mL, not less than about 5 µg/mL, not less than about 6 µg/mL, not less than about 7 µg/mL, not less than about 8 µg/mL, not less than about 9 µg/mL, not less than about 10 µg/mL, not less than about 11 µg/mL, not less than about 12 µg/mL, not less than about 13 µg/mL, not less than about 14 µg/mL, not less than about 15 µg/mL, not less than about 16 µg/mL, not less than about 17 µg/mL, not less than about 18 µg/mL, not less than about 19 µg/mL, not less than about 20 µg/mL, not less than about 25 µg/mL, not less than about 30 µg/mL, not less than about 35 µg/mL, not less than about 40 µg/mL, not less than about 45 µg/mL, not less than about 50 µg/mL, not less than about 60 µg/mL, not less than about 70 µg/mL, not less than about 80 µg/mL, not less than about 90 µg/mL, not less than about 100 µg/mL, not less than about 110 µg/mL, not less than about 120 µg/mL, not less than about 130 µg/mL, not less than about 140 µg/mL, not less than about 150 µg/mL, not less than about 160 µg/mL, not less than about 170 µg/mL, not less than about 180 µg/mL, not less than about 190 µg/mL, not less than about 200 µg/mL, not less than about 210 µg/mL, not less than about 220 µg/mL, not less than about 230 µg/mL, not less than about 240 µg/mL, not less than about 250 µg/mL, or any other plasma concentration of a compound described herein.

The plasma concentration of an immunotherapy described herein can be, for example, about 1 µg/mL to about 2 µg/mL; about 1 µg/mL to about 5 µg/mL; about 5 µg/mL to about 10 µg/mL; about 10 µg/mL to about 25 µg/mL; about 25 µg/mL to about 50 µg/mL; about 50 µg/mL to about 75 µg/mL; about 75 ng/mL to about 100 µg/mL; about 100 µg/mL to about 150 µg/mL; about 150 µg/mL to about 200 µg/mL; about 200 µg/mL to about 250 µg/mL; about 250 µg/mL to about 300 µg/mL; about 300 µg/mL to about 350 µg/mL; about 350 µg/mL to about 400 µg/mL; about 400 µg/mL to about 450 µg/mL; about 450 µg/mL to about 500 µg/mL; about 500 µg/mL to about 600 µg/mL; about 600 µg/mL to about 700 µg/mL; about 700 µg/mL to about 800 µg/mL; about 800 µg/mL to about 900 µg/mL; about 900 µg/mL to about 1,000 µg/mL; about 1,000 µg/mL to about 1,100 µg/mL; about 1,100 µg/mL to about 1,200 µg/mL; about 1,200 µg/mL to about 1,300 µg/mL; about 1,300 µg/mL to about 1,400 µg/mL; about 1,400 µg/mL to about 1,500

µg/mL; about 1,500 µg/mL to about 1,600 µg/mL; about 1,600 µg/mL to about 1,700 µg/mL; about 1,700 µg/mL to about 1,800 µg/mL; about 1,800 µg/mL to about 1,900 µg/mL; or about 1,900 µg/mL to about 2,000 µg/mL.

An OV of the disclosure can be measured in a method or composition herein or in plasma as plaque forming units (pfu). The pfu of an OV can be, for example, from about $10^1$ to about $10^{18}$ pfu. An OV of the disclosure can be, for example, at least about $10^1$, at least about $10^2$, at least about $10^3$, at least about $10^4$, at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, at least about $10^{16}$, at least about $10^{17}$, or at least about $10^{18}$ pfu. An OV of the disclosure can be, for example, at most about $10^1$, at most about $10^2$, at most about $10^3$, at most about $10^4$, at most about $10^5$, at most about $10^6$, at most about $10^7$, at most about $10^8$, at most about $10^9$, at most about $10^{10}$, at most about $10^{11}$, at most about $10^{12}$, at most about $10^{13}$, at most about $10^{14}$, at most about $10^{15}$, at most about $10^{16}$, at most about $10^{17}$, or at most about $10^{18}$ pfu.

An OV of the disclosure can be measured in a method or composition herein or in plasma as vector genomes. An OV of the disclosure can be, for example, from about $10^1$ to about $10^{18}$ vector genomes. An OV of the disclosure can be, for example, at least about $10^1$, at least about $10^2$, at least about $10^3$, at least about $10^4$, at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, at least about $10^{16}$, at least about $10^{17}$, or at least about $10^{18}$ vector genomes. An OV of the disclosure can be, for example, at most about $10^1$, at most about $10^2$, at most about $10^3$, at most about $10^4$, at most about $10^5$, at most about $10^6$, at most about $10^7$, at most about $10^8$, at most about $10^9$, at most about $10^{10}$, at most about $10^{11}$, at most about $10^{12}$, at most about $10^{13}$, at most about $10^{14}$, at most about $10^{15}$, at most about $10^{16}$, at most about $10^{17}$, or at most about $10^{18}$ vector genomes.

An OV of the disclosure can be measured in a method or composition herein or in plasma using multiplicity of infection (MOI). MOI can be, for example, the ratio, or multiple of viral genomes to the cells to which the nucleic acid can be delivered. An OV of the disclosure can be, for example, from about $10^1$ to about $10^{18}$ MOI. An OV of the disclosure can be, for example, from about $10^1$ to about $10^{18}$ pfu. An OV of the disclosure can be, for example, at least about $10^1$, at least about $10^2$, at least about $10^3$, at least about $10^4$, at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, at least about $10^{16}$, at least about $10^{17}$, or at least about $10^{18}$ MOI. An OV of the disclosure can be, for example, at most about $10^1$, at most about $10^2$, at most about $10^3$, at most about $10^4$, at most about $10^5$, at most about $10^6$, at most about $10^7$, at most about $10^8$, at most about $10^9$, at most about $10^{10}$, at most about $10^{11}$, at most about $10^{12}$, at most about $10^{13}$, at most about $10^{14}$, at most about $10^{15}$, at most about $10^{16}$, at most about $10^{17}$, or at most about $10^{18}$ MOI.

Treatment of Brain Disorders and Cancers

The methods and combination therapies of this disclosure can provide a treatment for a disease or condition. The disease can be a brain or spinal cord disease. In treating the disease, a peptide can cross the blood brain barrier of a subject. The subject can be a human. Subjects can be humans; non-human primates such as chimpanzees, and other apes and monkey species; farm animals such as cattle, horses, sheep, goats, swine; domestic animals such as rabbits, dogs, and cats; and laboratory animals including rodents, such as rats, mice and guinea pigs. A subject can be of any age. Subjects can be, for example, elderly adults, adults, adolescents, pre-adolescents, children, toddlers, infants, and fetuses in utero.

Treatment can be provided to the subject before clinical onset of disease. Treatment can be provided to the subject after clinical onset of disease. Treatment can be provided to the subject after 1 day, 1 week, 6 months, 12 months, or 2 years or more after clinical onset of the disease. Treatment can be provided to the subject for more than 1 day, 1 week, 1 month, 6 months, 12 months, 2 years or more after clinical onset of disease. Treatment can be provided to the subject for less than 1 day, 1 week, 1 month, 6 months, 12 months, or 2 years after clinical onset of the disease. Treatment can also include treating a human in a clinical trial. A treatment can comprise simultaneous or sequential administration to a subject of a therapeutically-effective amount of a Tie-2 activator; a therapeutically-effective amount of a modulator of an immune checkpoint molecule; or an OV.

Examples of brain diseases or conditions that can be treated with a combination therapy of the disclosure include Acoustic Neuroma (Vestibular Schwannoma), Acute Subdural Hematomas, Addictions (e.g., alcoholism, drug addiction, nicotine or tobacco, etc.), Alzheimer's disease, Amyotrophic Lateral Sclerosis (ALS, or Lou Gehrig's Disease), Anaplastic Astrocytoma (AA), Anxiety and related disorders, Anorexia, Aqueductal Stenosis, Arachnoid Cysts, Arnold Chiari Malformation, Arteriovenous Malformation (AVM), Astrocytoma, Autism, Ballism, bipolar disorders, Brain Aneurysm, Brain Attack, Brain Metastases, Brainstem Glioma, Bulimia, Carotid Stenosis, Catastrophic Epilepsy in Children, Cavernous Angioma, Cerebral Aneurysms, Cerebral Contusion and Intracerebral Hematoma, Chiari Malformation, Chordomas, Chorea, Chronic Subdural Hematomas, Colloid Cyst, Coma, Concussion, Cranial GunShot Wounds, Craniopharyngioma, Craniosynostosis, Cushing's Disease, Cyst (Epidermoid Tumor), Depression and related disorders, eating disorders, Epidural Hematomas Epilepsy, Essential Tremor, Extratemporal Lobe Epilepsies, Facet Joint Syndrome, Ganglioglioma, GBM (Glioblastoma Multiforme), Germinoma, Glioblastoma Multiforme (GBM), Glioma, Glomus Jugulare Tumor, Glossopharyngeal Neuralgia, Hemangioblastomas, Hemi-Facial Spasm, Hydrocephalus, Huntington's disease, Intracerebral Hemorrhage, Intracranial Hypotension, JPA (Juvenile Pilocytic Astrocytoma), Lennox-Gestaut Syndrome, Lipomyelomeningocele, Low-Grade Astocytoma (LGA), Lymphocytic Hypophysitis, Lymphoma, Medulloblastoma, Meningioma, Mesial Temporal Lobe Epilepsy, Metastatic Brain Tumors, Moyamoya Disease, multiple sclerosis, Nelson's Syndrome, Neurocysticercosis, Neurofibroma, Nonfunctional Pituitary Adenoma, Normal Pressure Hydrocephalus, obsessive-compulsive disorders, Oligodendroglioma, Optic Nerve Glioma, Osteomyelitis, Parkinson's Syndrome, Paranoia and related disorders, Pediatric Hydrocephalus, Phantom Limb Pain, Pilocytic Astrocytoma, Pineal Tumor, Pineoblastoma, Pineocytoma, Pituitary Adenoma (Tumor), Pituitary Apoplexy, Pituitary Failure, Postherpetic Neuralgia, Post-Traumatic Seizures, Primary CNS Lymphoma, Prolactinoma, Pseudotumor Cerebri, Rathke's Cleft Cyst, Recurrent Adenomas, Rheumatoid Arthritis, Schizophrenia, Schwannomas, Scoliosis, Skull Fracture, Slit Ventricle Syndrome, Spasticity, Spontaneous Intracranial Hypotension, Stroke (Brain Attack, TIA), Subarachnoid Hemorrhage, Syrinx, Thyrotroph (TSH) Secreting Adenomas, Torticollis, Transient Ischemic Attacks (TIA), Traumatic Hematomas, Trigeminal Neuralgia, Vestibular Schwannoma, depression, mood disorders, memory disorders, disorders of spatial memory or navigation, stress-related disorders, post-traumatic stress disorder, pain, aging, hippocampal atrophy, brain infections including fungal infections and progressive multifocal leucoencepalopathy, or another brain disease or condition.

EXAMPLES

Example 1

Treatment of Human Subjects with a Combination of Immunotherapies and an Activator of Tie-2

A subject receives 30 mg of a sodium salt of compound 1 or compound 2, illustrated below, for example, 15 mg b.i.d. (total daily dosage of 30 mg/day), for 3 months. Ipilimumab or nivolumab is administered concurrently at a dose of 10 mg/kg, intravenously, every 3 weeks for up to 4 doses. The Maximum Observed Serum Concentrations ($C_{max}$) of compound 1 and ipilimumab or nivolumab in the subject are measured by enzyme-linked immunoabsorbent assay (ELISA). Single-dose Pharmacokinetic (PK) parameters of compound 1 and ipilimumab or nivolumab are derived from serum concentration versus time data. $C_{max}$ is measured from first dose prior to the administration of the second dose as micrograms per milliliter (μg/mL). Samples are obtained at 0 hour (predose) on days 1, 2, 3, and 4; samples are also obtained 1 hour and 30 minutes (min), 2 hours, 2.5 hours, 3.5 hours, 4.5 hours, 6 hours, and twelve hours post dose. Samples are obtained throughout weeks 2, 3, 4, 7, and 10. In calculating PK parameters, predose concentrations and concentrations prior to first quantifiable concentration below the lower limit of quantitation (LLOQ) is treated as missing for the calculation of summary statistics.

Compound 1

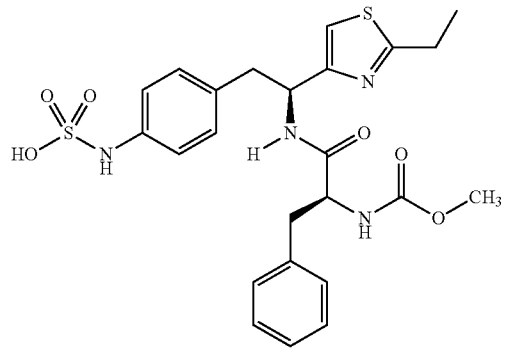

Compound 2

The Area Under the Serum Concentration-time Curve (AUC) From Time Zero to Day 21, $AUC_{(0-21d)}$, of compound 1 and ipilimumab or nivolumab are measured. Single-dose pharmacokinetic parameters are derived from serum concentration versus time data. $AUC_{(0-21d)}$ is measured from first dose to end of the induction period as micrograms*hours per milliliter (μg*h/mL). Samples are obtained at 0 hour (predose) on days 1, 2, 3, and 4; samples are also obtained 1.5 hours, 2 hours, 2.5 hours, 3.5 hours, 4.5 hours, 6 hours, and twelve hours post dose. Samples are obtained throughout weeks 2, 3, 4, 7, and 10. In calculating PK parameters, predose concentrations and concentrations prior to first quantifiable concentration below the lower limit of quantitation (LLOQ) are treated as missing for the calculation of summary statistics.

The overall tumor response is measured in: 1) human subjects receiving a single administration of one of compound 1, ipilimumab, and nivolumab; and 2) human subjects receiving a combination therapy treatment of either compound 1 and ipilimumab or compound 1 and nivolumab.

The overall tumor response is measured based on overall survival of human subjects. Overall survival is obtained with a delayed separation Kaplan-Meier survival curve over a period of at least 6 months. An imaging-based clinical response can be further determined as the combination of assessments of index and non-index lesions using the following modified WHO criteria: a) complete response is a complete disappearance of all lesions; b) partial response is a decrease relative to baseline of 50% or greater in the sum of the products of the two largest perpendicular diameters of all index lesions, in the absence of complete response; c) stable disease does not meet criteria for complete or partial response, in the absence of progressive disease, or a decrease or tumor stabilization of one or more non-index lesions; d) progressive disease is at least 25% increase in the sum of the products of all index lesions (taking as reference the smallest sum recorded at or following baseline) or the appearance of any new lesion, or progression of a non-index lesion.

Example 2

Treatment of Human Subjects Afflicted with Renal Cell Carcinoma, Lung Cancer, Melanoma, and Advanced Metastatic Solid Tumors Nivolumab (BMS-936558 or MDX1106) is an immunotherapy that acts as an immunomodulator by blocking ligand activation of the programmed cell death 1 (PD-1) receptors on activated T cells. When programmed cell death 1 ligand (PD-L1) binds to PD-1, the T cell dies or becomes anergic.

The following experiments can be conducted to evaluate the outcome of a combination therapy of the disclosure in treating human subjects with renal cell carcinoma, lung cancer, melanoma, and advanced metastatic solid tumors.

Purpose: to evaluate the outcome of treating human subjects with renal cell carcinoma, lung cancer, melanoma, and advanced metastatic solid tumors with compound 1 and nivolumab.

Rationale: administration of a combination treatment of the disclosure can enhance the immunologic responses of renal, lung, skin, and solid tumor cells expressing PD-1.

Methods: a study is designed with some, or all, of the following experimental arms. 1) experimental arm 1: a dose of a sodium salt of compound 1, from about 5 mg to about 60 mg, for example, 15 mg b.i.d. (total daily dosage of 30 mg/day), for about 3 months, is administered as a monotherapy to a first group of subjects. 2) experimental arm 2: a dosage of nivolumab of about 10 mg/kg, administered every 3 weeks, for up to 4 doses is administered as a monotherapy to a second group of subjects. 3) experimental arm 3: the treatments described in experimental arms 1) and 2) are co-administered. 4) control arm 4: a first placebo comprised of the reconstitution solution and solubilizing agents used for compound 1 is administered twice a day for about 3 months as a sham monotherapy. 5) control arm 5: a second placebo comprised of the reconstitution solution and solubilizing agents used for nivolumb is administered every 3 weeks, for up to 4 doses as a sham monotherapy; and 6) experimental arm 6: the treatments described in experimental arms 4) and 5) are co-administered.

Clinical response of the tumor is determined by measurement of the tumor volume from renal, lung, skin, and solid tumor cells measured as a prolate spheroid. Student's t test is used to assess the significance of the effects of different treatments against the tumors. A reduction in tumor volume with the combination therapies and methods of the disclosure can be used to measure the outcome of treating human subjects with monotherapies versus a combination therapy of the disclosure.

Clinical response is further measured using computed tomography scanning, magnetic resonance imaging, or positron emission tomography (PET), with $^{18}$F-fluorodeoxyglucose ($^{18}$FDG-PET) to determine tumor size and the rate of death of tumors. A reduction in tumor volume with the combination therapies and methods of the disclosure is used to measure the outcome of treating human subjects with monotherapies versus a combination therapy of the disclosure. Sequential rounds of imaging are performed to determine the durability of clinical response, time to relapse, and sensitivity to additional rounds of therapy.

The imaging-based clinical response can be further determined as the combination of assessments of index and non-index lesions using the following modified WHO criteria: a) complete response is a complete disappearance of all lesions; b) partial response is a decrease relative to baseline of 50% or greater in the sum of the products of the two largest perpendicular diameters of all index lesions, in the absence of complete response; c) stable disease does not meet criteria for complete or partial response, in the absence of progressive disease, or a decrease or tumor stabilization of one or more non-index lesions; d) progressive disease is at least 25% increase in the sum of the products of all index lesions (taking as reference the smallest sum recorded at or following baseline) or the appearance of any new lesion, or progression of a non-index lesion.

Clinical response is further measured by biopsy of the lesion before, during, or after therapy to determine the extent of an immune infiltrate. The biopsy is collected and the number of immune infiltrating cells, for example, cytotoxic T cells, NK cells, type 1 and type 2 macrophages, $T_{regs}$, and myeloid derived suppressor cells, is quantified. A post-treatment increase in cytotoxic T cells, NK cells, or type 1 macrophages, or a decrease in type 2 macrophages, $T_{regs}$, or myeloid derived suppressor cells, indicates that an immune checkpoint has been effectively blocked. Sequential rounds of immune infiltrate analysis are performed to determine the durability of clinical response, time to relapse, and sensitivity to additional rounds of therapy.

Clinical response is further measured by assessment of circulating tumor DNA (ctDNA) in plasma before, during, or after therapy. An increase in ctDNA during therapy, followed by a decrease after therapy, indicates tumor cell killing in response to therapy. Sequential rounds of ctDNA assessment are performed to determine the durability of clinical response, time to relapse, and sensitivity to additional rounds of therapy.

The overall tumor response is measured based on overall survival of human subjects. Overall survival is obtained with a delayed separation Kaplan-Meier survival curve over a period of at least 6 months.

Example 3

Blood-Brain Barrier Transendothelial Electrical Resistance (TEER) Measurements

To assess the role of Angiopoietin 1 (Ang-1), Angiopoietin 2 (Ang-2), and a Tie-2 activator in modulating permeability at the blood-brain barrier transendothelial electrical resistance (TEER) measurements were performed to obtain continuous barrier tightness index of primary mouse brain endothelial cells (MBMECs).

TEER measurements were performed as follows: isolated mouse brain microvascular endothelial cells (MBMECs) (100,000 cells/cm$^2$, 4-6 mice/prep) were seeded onto 1 µm pore 24-well PET transwell inserts (Greiner Bio-One) pre-coated with fibronectin (5 µg/cm$^2$, Sigma-Aldrich™). The inserts were transferred to a cellZscope® device placed in a humidified incubator (37° C., 5% CO$_2$) and impedance measurements obtained continuously. Treatment was started upon reaching a plateau in TEER levels.

Isolation of mouse brain microvascular endothelial cells (MBMECs) was conducted as follows: Meninges-free brains were pooled and homogenized followed by digesting the pellet with 0.75% Collagenase II (Worthington™) in buffer A (1:1:1 volume ratio) for 1 hour with shaking at 37° C. For removing myelin, samples were resuspended in 25% BSA and centrifuged at 1500×g for 30 min at 4° C., followed by digesting the pellet with Collagenase/Dispase® (Roche™) and DNase I (Worthington™) in buffer A for 12 min at 37° C. After centrifugation, MBMECs were resuspended in MCDB-131 complete medium and were seeded on 6-well plates pre-coated with type I Collagen (150 µg/cm$^2$, Corning®). After 4 hours of incubation, the medium was changed to puromycin (5 µg/ml) containing medium. Cells were placed in puromycin-free medium after 3 days.

MBMECs were isolated from CD1 and C57BL/6J mice pooling 4-6 animals in each preparation and cultured on transwell inserts. Permeability of the MBMEC monolayers to 0.45 kD Lucifer-Yellow (LY; Sigma™), Texas Red® 3 kD dextran (Invitrogen™), TMR 20 kD dextran (Sigma™) and 70 kD FITC dextran (Sigma™) was determined as follows.

Medium from the bottom chamber at each time point was read in a fluorescence plate reader (Tecan™) at the corresponding tracer excitation/emission and normalized to the apical chamber fluorescence with the ratio for the control condition set to 100%.

Figure 2:
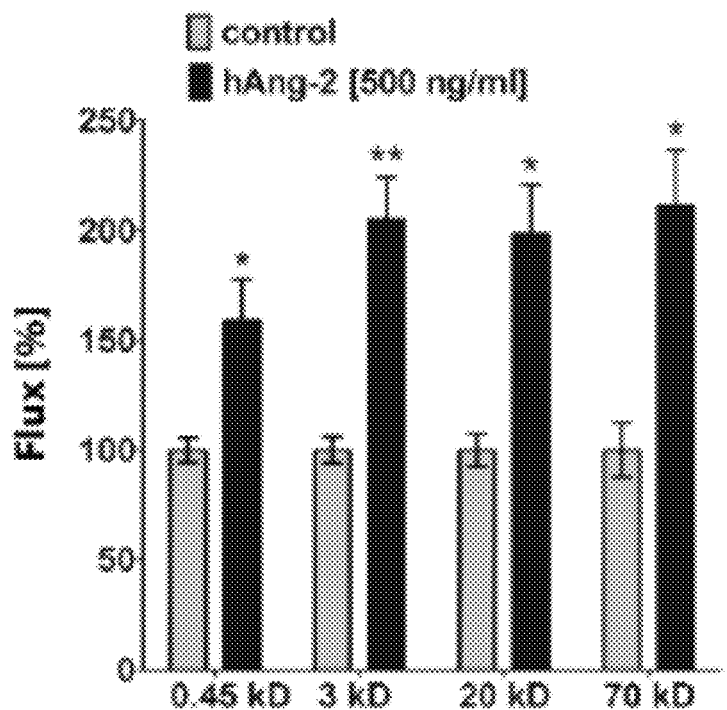
FIG. 2 is a graph illustrating a transwell assay demonstrating that treatment with angiopoeitin 2 (Ang-2) resulted in increased permeability to tracers.

The TEER measurements of MBMECs suggest a decrease in transendothelial electrical resistance at the blood-brain barrier upon transgenic endothelial-specific overexpression of hAng-2 (FIG. 1, PANEL A) or upon treatment with recombinant human Ang-2 (rhAng-2) treatment (FIG. 1, PANEL B). The results suggest a barrier-opening effect of Ang-2. To rule out the possibility that Ang-2-mediated permeability was specific to the CD1 strain of mice used in the experiment, transwell assays applying fluorescent dextrans (3 kD, 20 kD, and 70 kD) and Lucifer-Yellow (LY 0.45 kD), using C57BL/6J mice were conducted. FIG. 2 illustrates that Ang-2 treatment in C57BL/6J mice resulted in increased permeability to tracers of all sizes.

Example 4

Angiopoietin 2 (Ang-2) Increases Vascular Permeability at the Blood-Brain Barrier In Vitro and In Vivo To ascertain the permeability effects of Ang-2 in vivo on the brain endothelium, experiments were performed on an Ang-2 gain-of-function (GOF) mouse model. Briefly, a Tie1-tTA driver and a TetOS hAng-2 responder transgene were generated with standard techniques. CD1 background mice received doxycycline-containing food pellets (100 mg/kg, ssniff Spezialdiaeten GmbH, Soest, Germany) during breeding. Transgene overexpression was induced from birth ($P_0$) in newborn littermates by withdrawing doxycycline. Genotypes were determined by PCR analysis and expression levels of hAng-2 were confirmed by serum ELISA. All mice used were adult (8-12 weeks) on the CD1 background and were not distinguished by sex.

Experiments using fluorescent tracer assays including the Evans blue dye were performed. For the in vivo tracer studies, a mixture (1:2) of Texas Red® 3 kD dextran (1 mM, Invitrogen™) and Lucifer-Yellow (10 mM, Sigma™) was injected into the tail vein of mice (100 μl/mouse) and allowed to circulate for 4 min. This injection was followed by administration of anesthesia and transcardial perfusion for 1 min with PBS. Brain and kidneys were isolated. The brains were homogenized (hemi-brain) and a single kidney from each mice was placed in PBS at 4° C. The remaining kidney and hemi-brain were frozen down in Tissue TEK® O.C.T. Compound (Sakura™) on dry ice for immunohistochemical analysis. After spinning down the samples at 10,000×g for 15 min at 4° C., the supernatant was measured in a fluorescence plate reader (Tecan™) at excitation/emission wavelength of 425/525 nm for Lucifer-Yellow and 595/625 nm for Texas Red® 3 kD dextran.

In experiments using bigger tracers, 2% Evans blue (70 kD, albumin-bound form) was injected intravenously into the tail vein of mice and allowed to circulate for 2 hours. After transcardial perfusion with PBS, isolated brains were minced with a scalpel and transferred into a tube containing formamide. Samples were homogenized by incubating at 67° C. for 24 hours, followed by centrifugation at 10.000×g for 1 hour at 4° C. The absorbance of the supernatants was measured at 620 nm in a plate reader (Tecan™).

Figure 3:
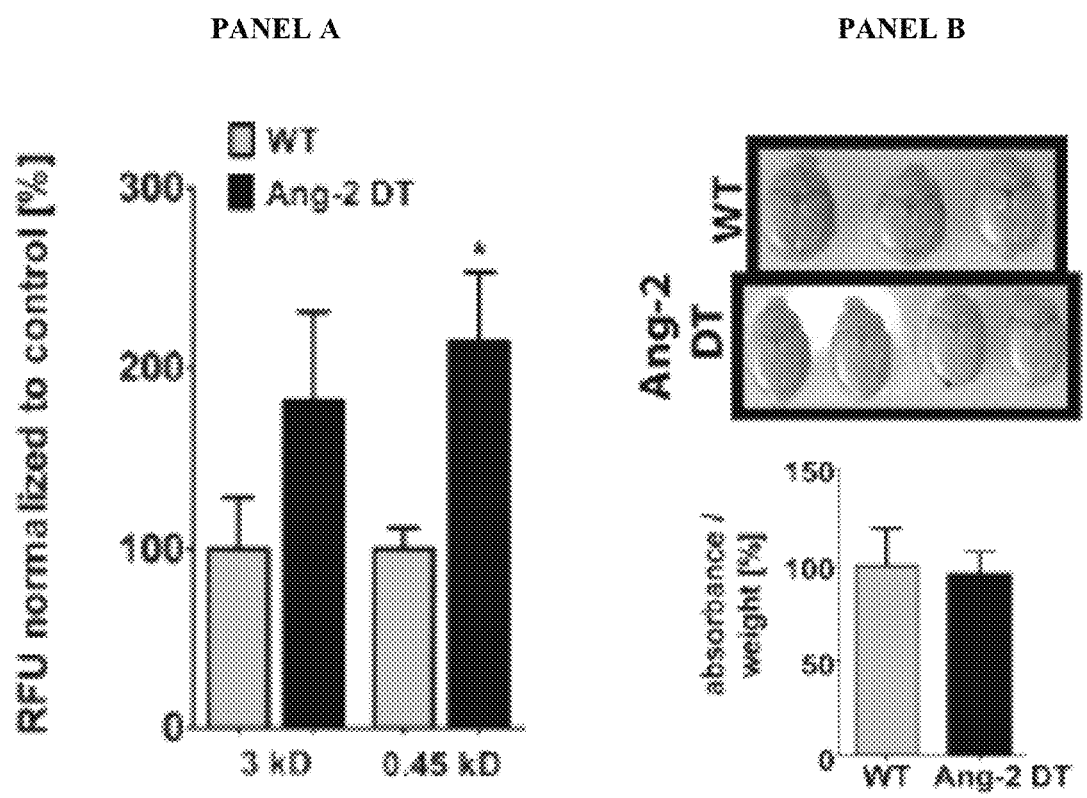
FIG. 3 illustrates the permeability effects of Ang-2 in vivo on the brain endothelium. PANEL A illustrates the diffusion of tracers. PANEL B illustrates the leakage of Evans blue in double transgenic (DT) and wild type (WT) mice.

The permeability to 0.45 kD Lucifer-Yellow was significantly increased in vivo in the brains of DT mice compared to WT mice (FIG. 3, PANEL A). An increase in the permeability to Texas Red® 3 kD dextran was also observed (FIG. 3, PANEL A). In contrast, no difference was observed in the permeability to Evans blue in vivo in the brains of DT mice compared to WT mice (FIG. 3, PANEL B). These results suggest that Ang-2 increases endothelial permeability in vivo in the brain for 0.45 kD Lucifer-Yellow and Texas Red® 3 kD dextran but not 70 kD Evans blue.

Example 5

Molecular Components of Ang-2 Mediated Permeability

To investigate the molecular components of Ang-2 mediated permeability immunohistochemistry (IHC) and electron microscopy (EM) experiments were performed analyzing the neurovascular unit (NVU) of DT mice.

For the Western blot experiments, samples were solubilized in urea/SDS buffer (2.3 M urea, 1.5% SDS, 50 mM Tris, 25 mM TCEP, and 0.01% BPB) for 1.5 h at 30° C. with shaking. Solubilized samples were loaded into Tris-HCl Bis-acrylamide gels (8-15%), electrophoresed, and subsequently transferred to nitrocellulose membranes at 4° C. overnight. Membranes were blocked for 1 hour at room temperature on a 1× Roti®-block (Roth™), incubated with primary antibodies overnight at 4° C., washed with PBS-T (0.5% Tween®-20), incubated with horseradish peroxidase-conjugated or fluorescent secondary antibodies (LI-COR™) for 1 h at room temperature. Membranes were imaged in Odyssey® (LI-COR™) imaging device and quantitation was performed on exported raw tiff files using Image Studio™ 2.1 software (LI-COR™).

For the electron microscopy (EM) experiments, mice (8 week old, n=3 for each genotype) were anesthetized and transcardially perfused with PBS for 1 min followed by a 4 min treatment with 4% PFA/2% glutaraldehyde in PBS. Isolated brains were fixed at room temperature for 2.5 hour in 1% $OsO_4$ and then stained in 2% uranyl acetate at 4° C. overnight. Brains were dehydrated in graded acetone with 15-20 min per step. Brains were immersed 1:1 in acetone/Durcupan™ for 1 hour and subsequently in Durcupan™ for 1 hour at room temperature, and polymerized at 60° C. for 72 hours.

To stain for the glycocalyx, mice (n=3 each genotype) were anesthetized as described above and perfused with 2% glutaraldehyde, 2% saccharose, 0.1 M sodium cacodylate buffer, and 2% lanthanum nitrate (pH 7.4). Brains were isolated and fixed for 2 hours in the perfusion solution and subjected to 2% $H_2O_2$, 2% saccharose, 0.1 M sodium cacodylate buffer, and 2% lanthanum nitrate for 12 hours at 4° C. followed by rinsing with 0.03 M NaOH and 2% saccharose.

The contrast was increased by using a 2% $OsO_4$ and 2% lanthanum nitrate followed by dehydration in graded ethanol/propylene oxide, and embedding in araldite. The polymerization was performed at 60° C. for 12 hours. For standard processing, ultrathin sections were contrasted with uranyl-acetate and lead citrate. Analysis of glyxocalyx was performed without any contrast enhancement to rule out an unspecific precipitation of these staining solutions. Sections were analysed using Tecnai™ Spirit BioTWIN FEI electron microscope (EM) at 120 kV. Images were taken with an Eagle™ 4K CCD bottom-mount camera.

Figure 4:
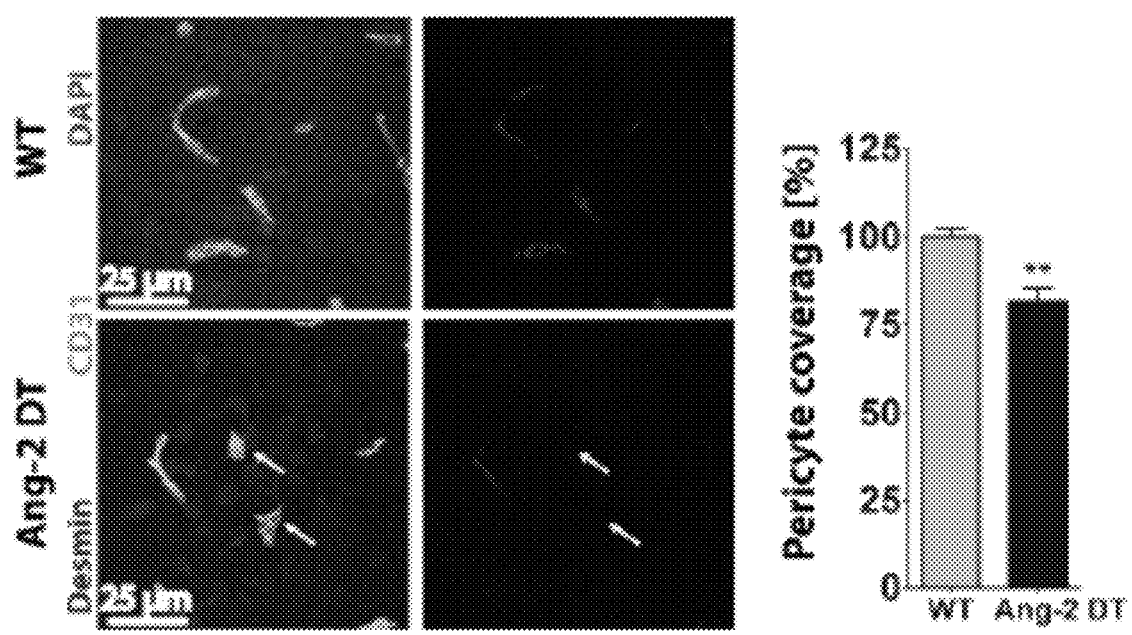
FIG. 4 illustrates the quantification of pericytes (desmin+) normalized to the number of CD31+ vessels in brain sections.
Figure 5:
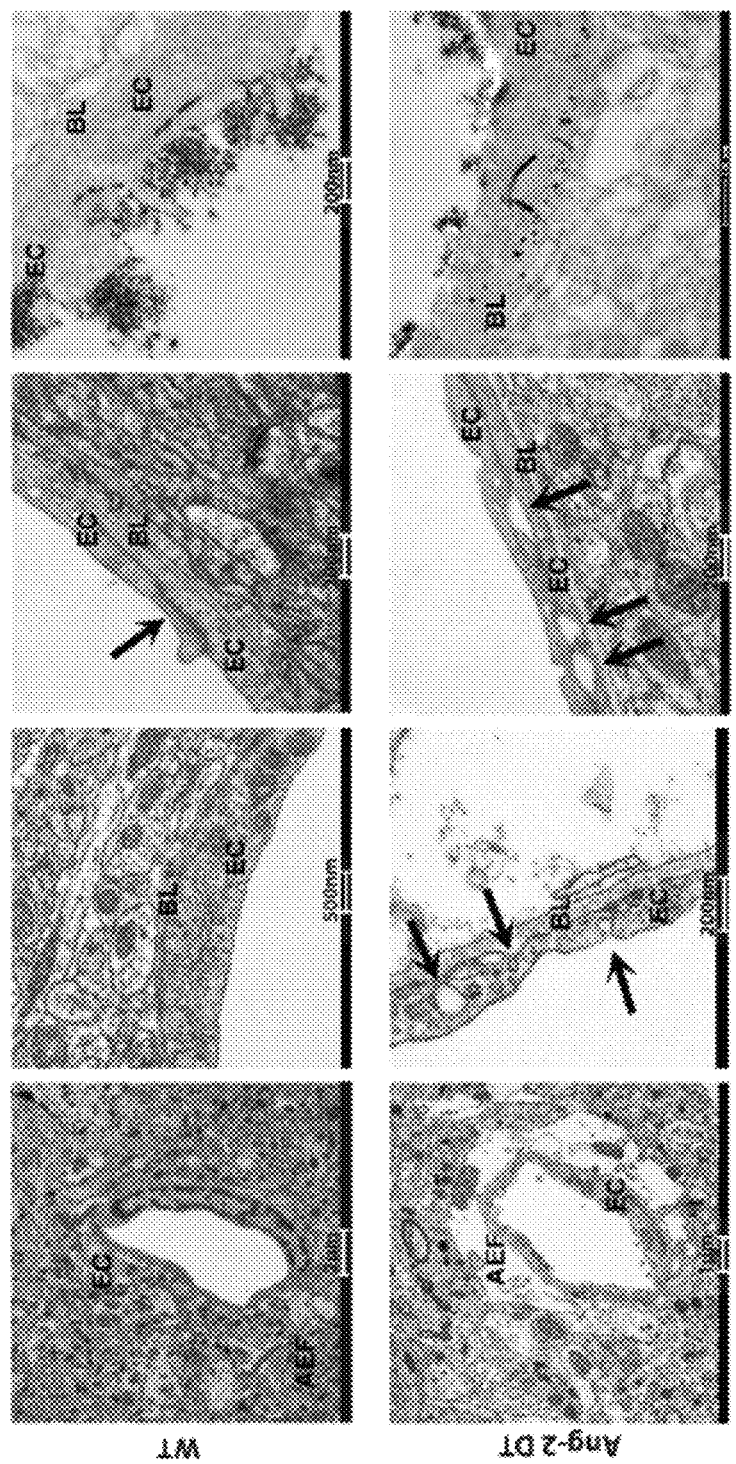
FIG. 5 illustrates the ultrastructural and biochemical histology analysis of endothelial permeability features in DT mice.
Figure 17:
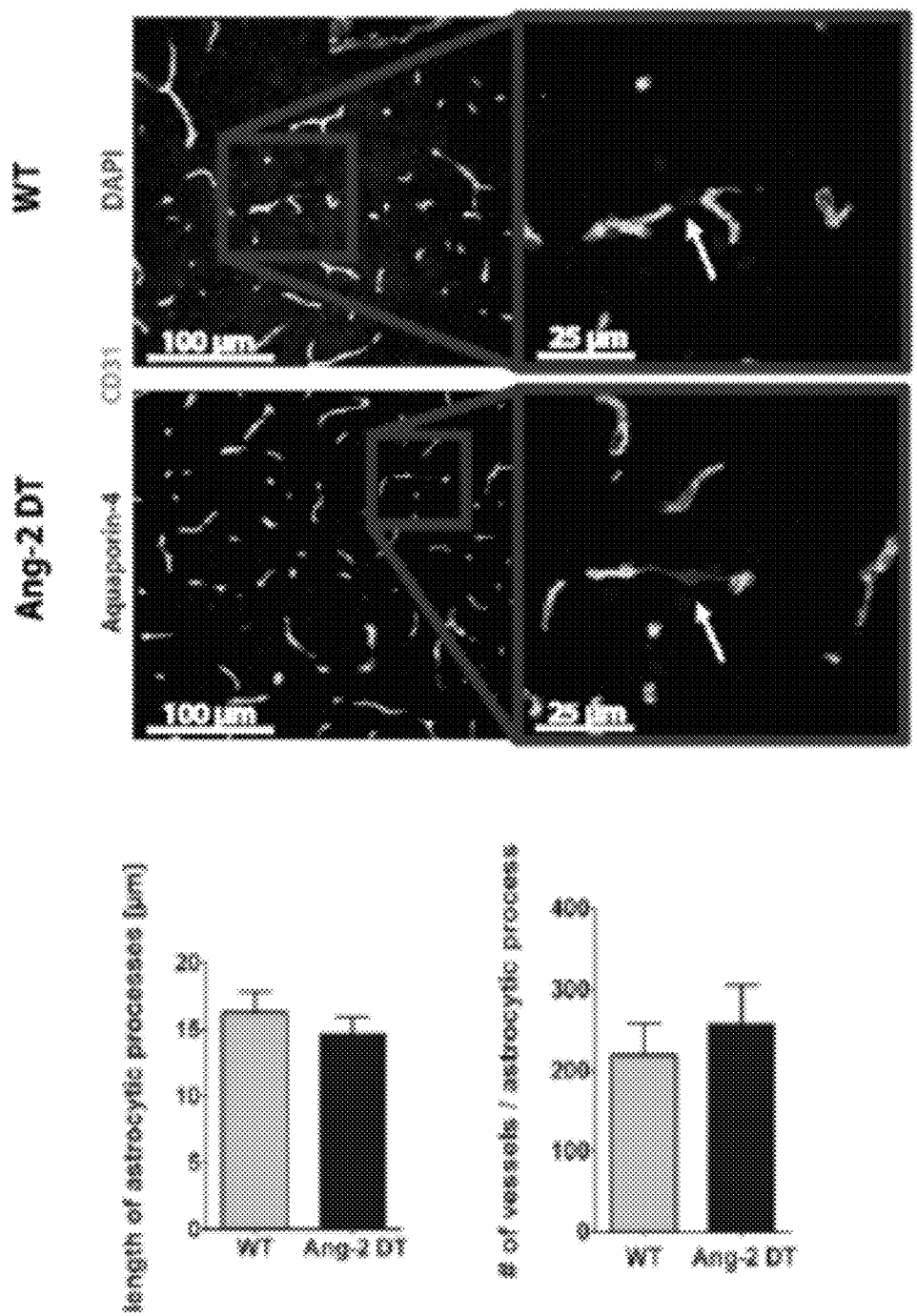
FIG. 17 illustrates the staining of an astrocyte endfeet marker (aquaporin-4, red) and a vessel marker (CD31, green) in cryosections of WT and DT mice.
Figure 18:
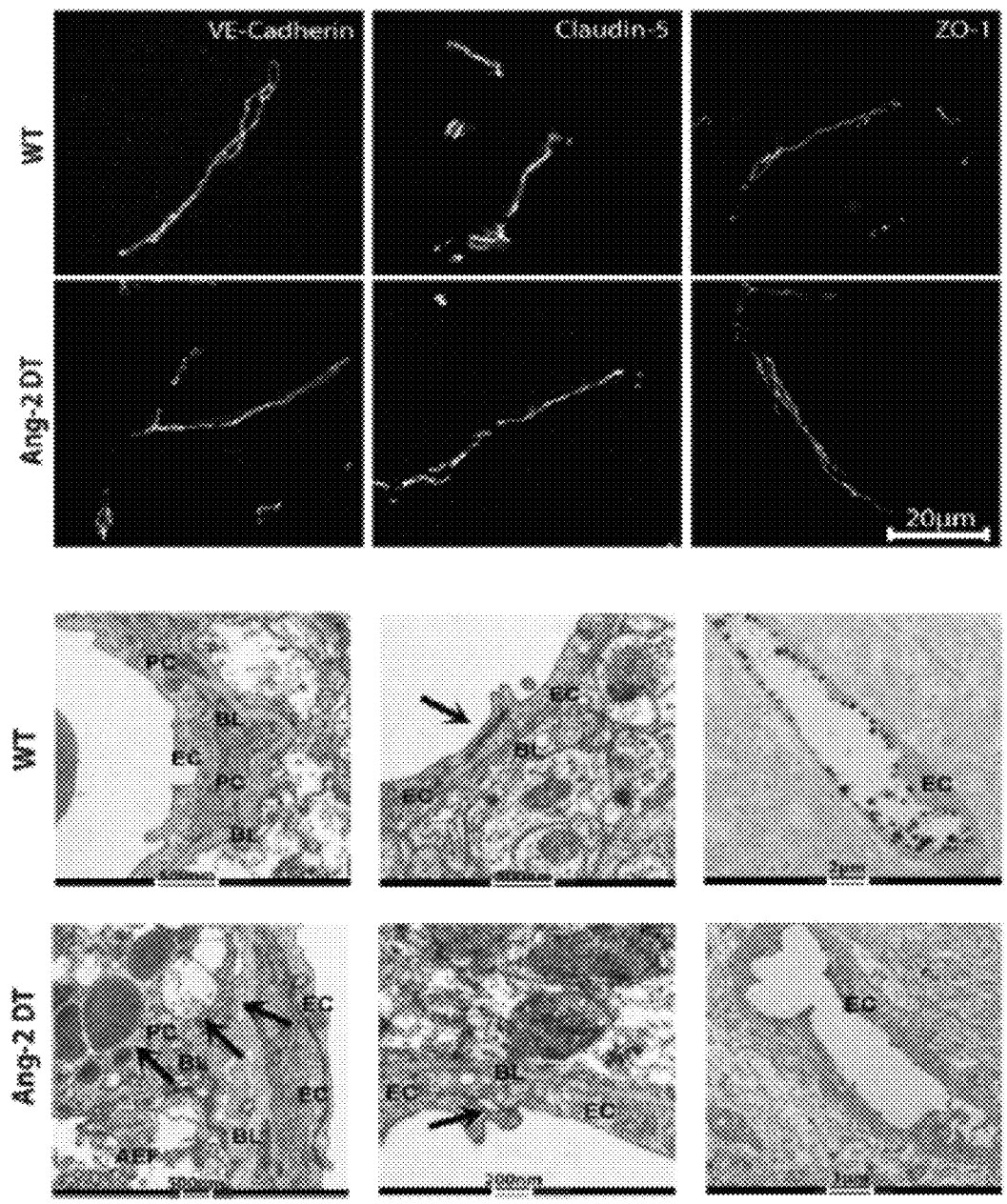
FIG. 18 illustrates representative images of VE-Cadherin, Claudin-5, and ZO-1 of 10 micron (μm) brain slices of WT and Ang-2 DT mice.

Astrocytic endfeet coverage can have an important role in barrier permeability. Pericytes can also be important in maintaining low BBB permeability by preventing caveolae-mediated transcytosis without affecting the intercellular junctions. IHC analysis suggested a dramatic decrease in pericytes (FIG. 4) as previously observed in peripheral vessels. EM analysis suggested neurovascular uncoupling as inferred from astrocytic endfeet swelling (FIG. 5) as well as occasional pericyte degeneration (FIG. 18). The EM analysis indicated increased flask-shaped plasmalemmal vesicles in DT mice (FIG. 5) reminiscent of caveolae that are responsible for higher peripheral endothelial permeability. The EM analysis also revealed decreased complexity of the inter-endothelial junctions with frequent gaps (FIG. 5) which is indicative of an increase in paracellular permeability mediated by Ang-2 as deduced from in vitro permeability assays. Changes were not observed in the in the astrocytic endfeet coverage of DT mice by IHC for aquaporin-4 (FIG. 17).

Figure 7:
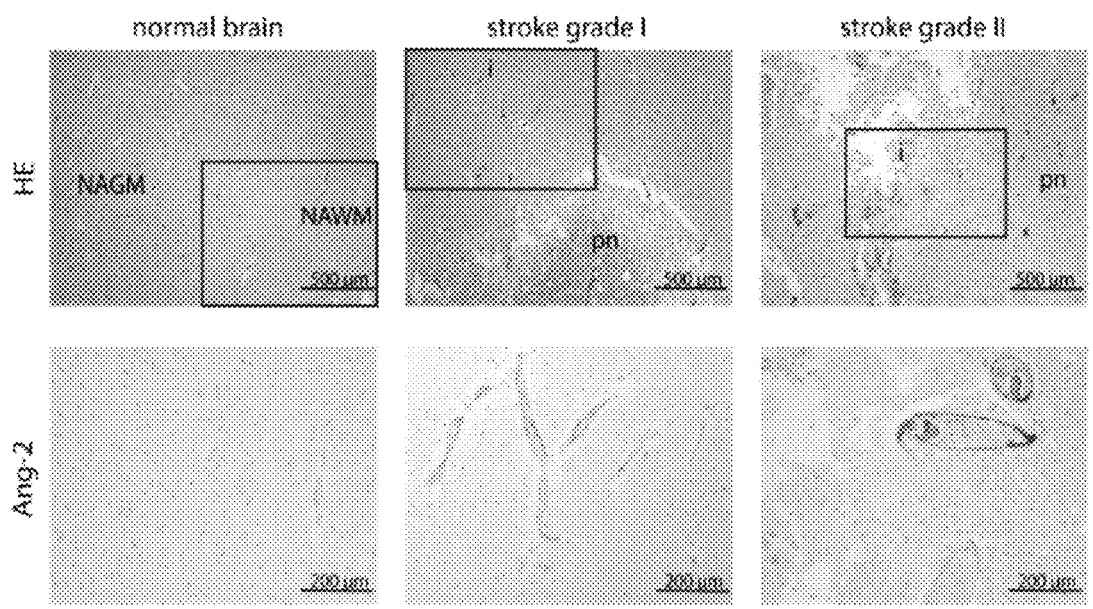
FIG. 7 illustrates brain histology sections in normal and stroke brains.

Additionally, the glycocalyx thickness between DT and WT mice was compared. The glycocalyx in DT mice, compared to WT mice, appeared considerably decreased based on lanthanum nitrate staining (FIG. 7).

Figure 6:
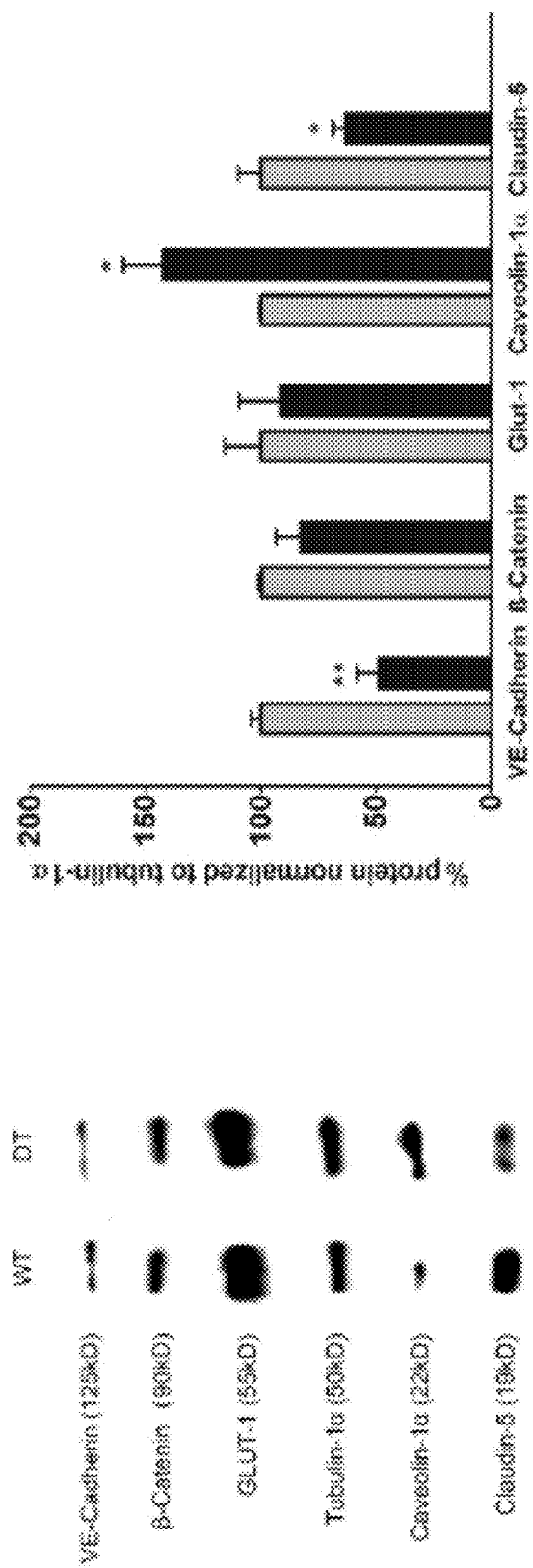
FIG. 6 illustrates Western blot analysis of isolated brain microvessels for VE-cadherin, β-catenin, GLUT-1, tubulin-1α, caveolin-1α, and claudin-5.

Western blotting was used to analyze permeability-related molecules of isolated microvessels. These experiments revealed a downregulation of VE-Cadherin, an important adherens-junctions molecule, and Claudin-5, a tight-junctions member. The expression of β-catenin, another adherens-junctions associated molecule, was not altered. No changes were observed in the expression of GLUT-1, a facilitative glucose transporter suggesting that specific junctional alterations caused by Ang-2 result in the permeability of the BBB (FIG. 6). These data support the EM analysis where gaps in the EC-junctions were observed. Caveolin-1, a scaffolding protein crucial for caveolae formation, appeared upregulated in the Western blots (FIG. 6). This observation supports the EM analysis that showed increased caveolae-like vesicles in the DT animals.

Example 6

Physiological Role of Ang-2 in Normal Human Brain and Stroke Human Brain

The physiological role of Ang-2 in disease was investigated in stroke, a neurological disorder associated with BBB disruption.

Human brain sections were thawed on a 37° C. heating plate for 10 min and washed 3× in PBS for 5 min. After fixation with 4% PFA in PBS for 10 min at room temperature and washes with PBS (3×5 min), sections were blocked in 5% BSA in PBS for 30 min with 0.1% Triton™-X 100 in a humidifying chamber, followed by another blocking step for 1 hour with 20% NGS in PBS with 0.1% Triton™-X 100. Tissue sections were then incubated in primary antibody in 10% NGS/PBS/0.1% Triton™-X 100 for 1.5 hours at room temperature followed by washes in PBS (3×5 min). The secondary antibody was incubated in the same solution as the primary antibody for 1 hour. After washing in PBS (3×5 min), slides were covered with ABC solution from Vectastain® ABC Kit (Vector™). The solution was incubated for 30 min on the objective slides, which were washed afterwards 3×5 min in PBS. Positive chromogenic reaction was observed under the microscope and stopped by washing 3×5 min PBS. Staining of the nuclei was done by Meyer's haematoxylin solution for 20 seconds. Sections were washed again with dH$_2$O and mounted with AquaPoly Mount. A Ventana Benchmark automated system was used for hAng-2 staining utilizing cell conditioning (preluted, Ventana Medical Systems) solution for antigen retrieval. Primary antibody signal was detected with IHC UltraMap AT kit (Ventana Medical Systems™). From the acquired images, Ang-2 positive vessels were counted and given a score from 0-3.

Figure 8:
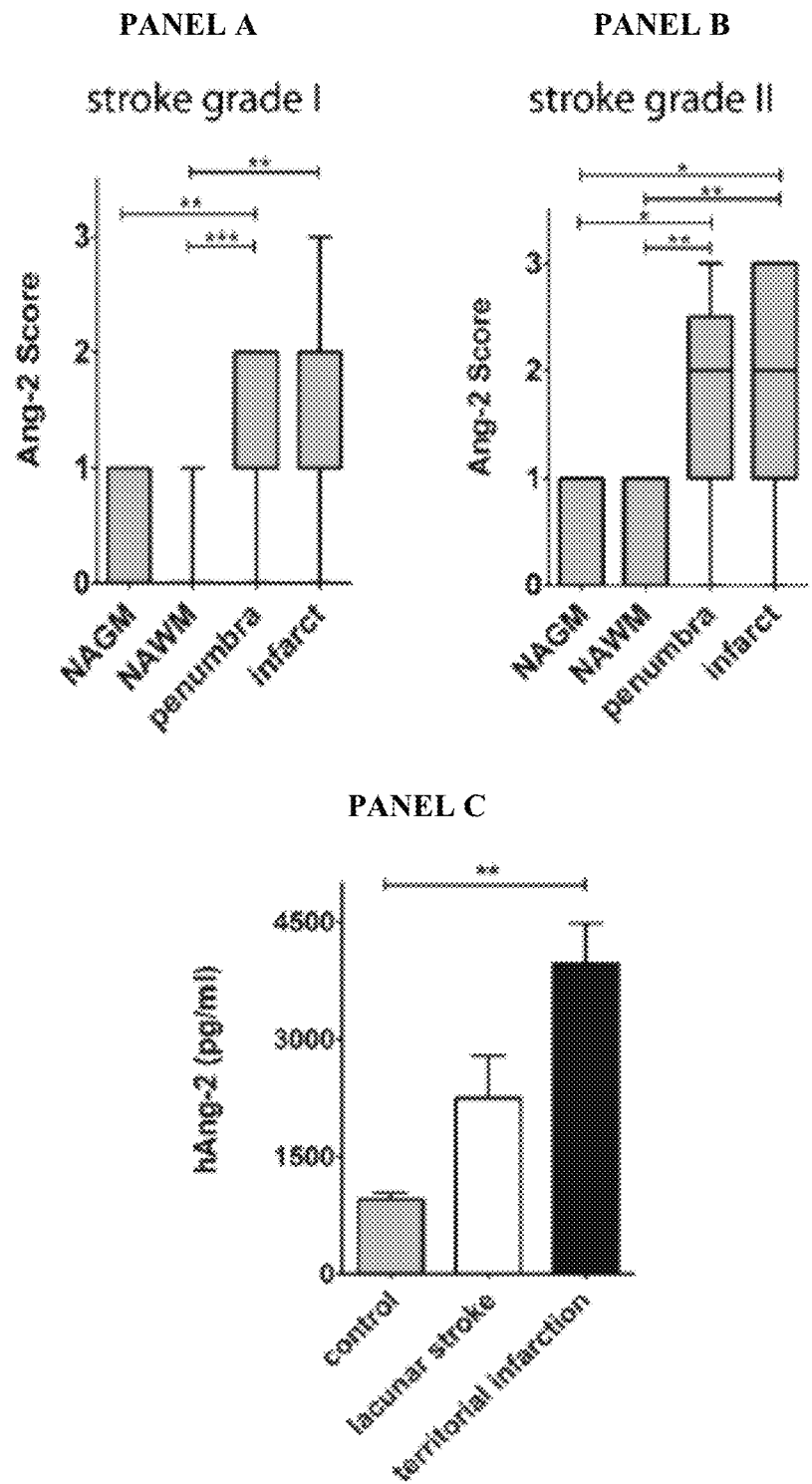
FIG. 8 illustrates graphs quantifying Ang-2 expression levels in normal brain tissue versus stroke brain tissue.

FIG. 7 illustrates brain histology sections in normal and stroke human brains. Human stroke samples were stained with H&E and hAng-2. NAWM=Normal appearing white matter, NAGM=normal appearing grey matter, i=infarct, pn=penumbra. While Ang-2 expression was very low in normal brains, the levels were higher in human stroke cases (FIG. 7, and FIG. 8, PANELS A and B). FIG. 8 illustrates that Ang-2 expression was higher in stroke area compared to the normal brain for both grades (n=13 cases, box-and-whiskers plot (2.5 ¬ 97.5 percentile), Kruskal-Wallis test with Dunn's multiple comparison correction). FIG. 8, PANEL A illustrates the results for stroke grade I. FIG. 8, PANEL B illustrates the results for stroke grade II. Serum analysis indicated a significantly higher expression of hAng-2 in stroke patients compared to healthy humans (FIG. 8, PANEL C).

Example 7

Physiological Role of Ang-2 in a Mouse Model of Cerebral Artery Occlusion

Mice with endothelial-specific overexpression of hAng-2 (DT mice) underwent a permanent middle cerebral artery occlusion (MCAO). After a permanent MCAO was performed, animals were allowed to survive for 24 hours or 72 hours. Mice were anesthetized intraperitoneally (i.p.) with a combination of midazolam/medetomidine/fentanyl (5/0.5/0.05 mg/kg body mass). Anesthesia was terminated by i.p. injection of atipamezol/naloxone/flumazenil 2.5/1.2/0.5 mg/kg body weight). Brains were isolated and frozen down in Tissue TEK® O.C.T. and stored at −80° C. until use. WT mice also underwent the procedure as controls.

Figure 9:
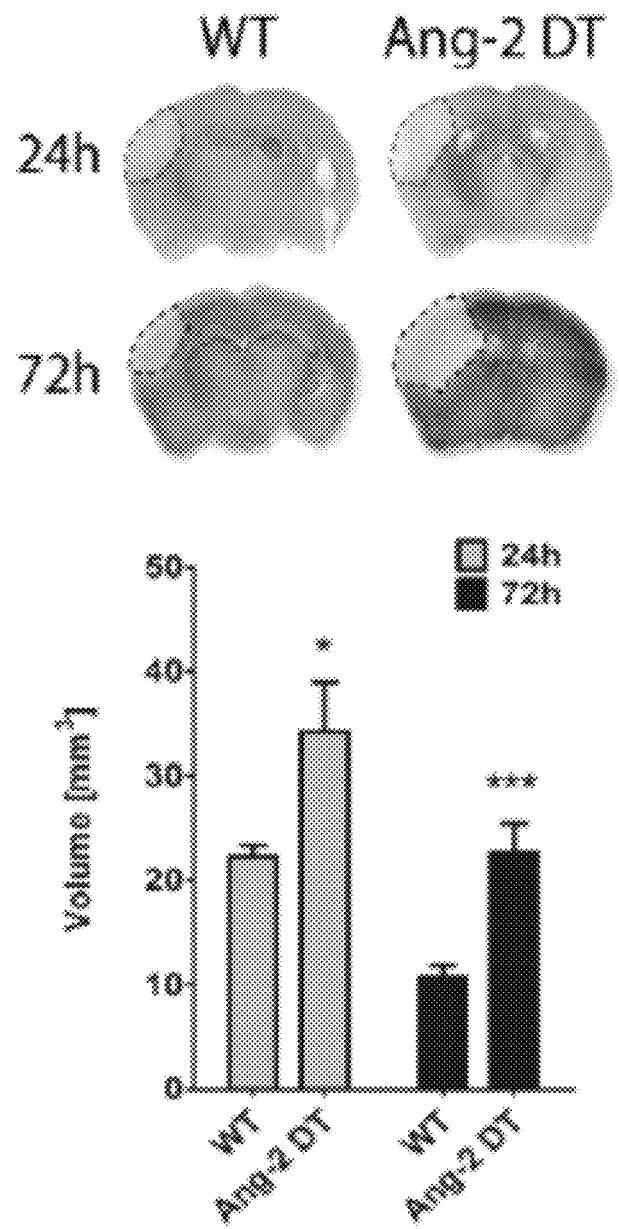
FIG. 9 illustrates the permanent middle cerebral artery occlusion (MCAO) infarct size in DT mice and WT mice.
Figure 10:
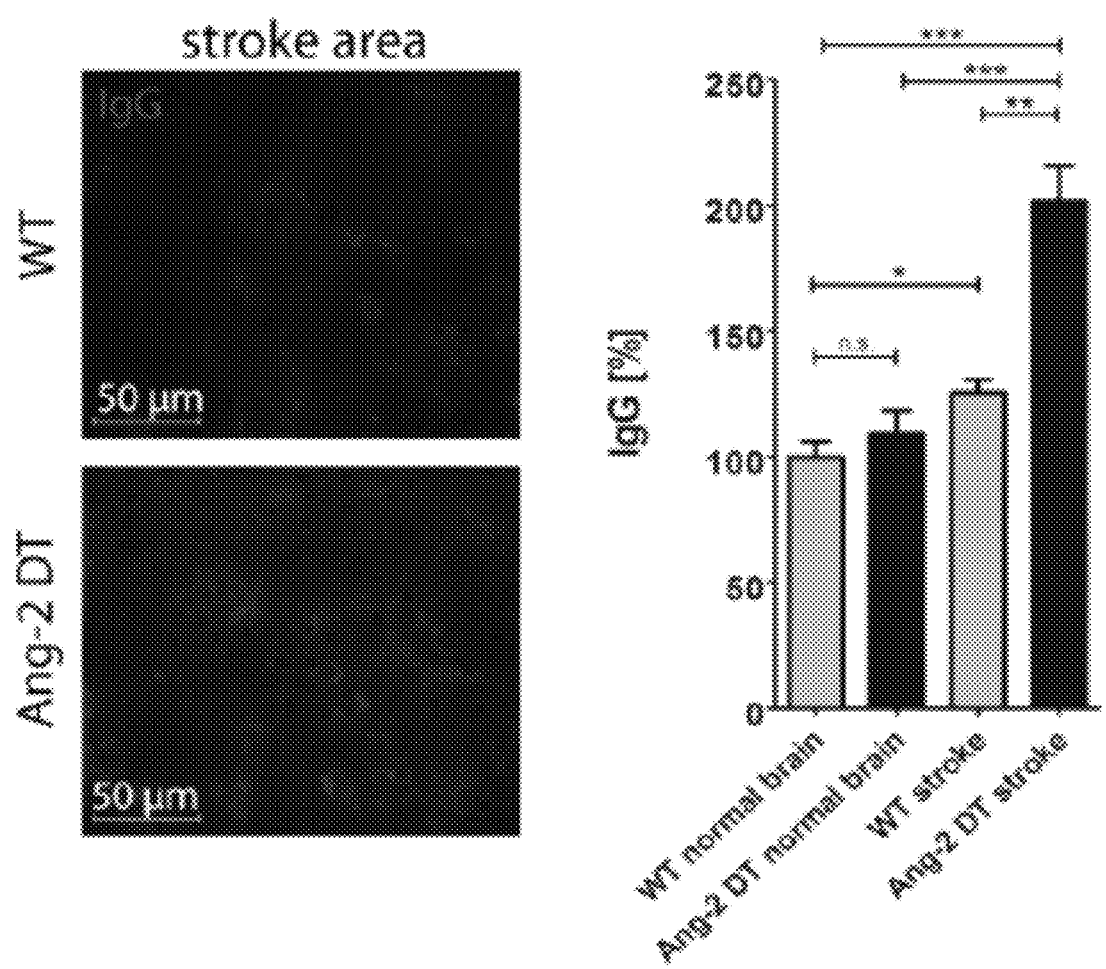
FIG. 10 illustrates the permeability to IgG in the stroke area of DT mice compared to WT mice.

Larger infarcts were detected in DT mice that were subjected to MCAO as compared to WT mice that were subjected to MCAO after 24 hours and 72 hours (FIG. 9). Additionally, the IgG permeability in the stroke area was increased in DT mice (FIG. 10). Mice were treated with a Tie-2 activator shown below:

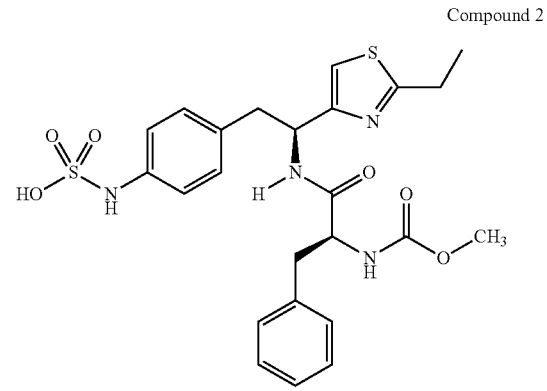

Compound 2

Figure 11:
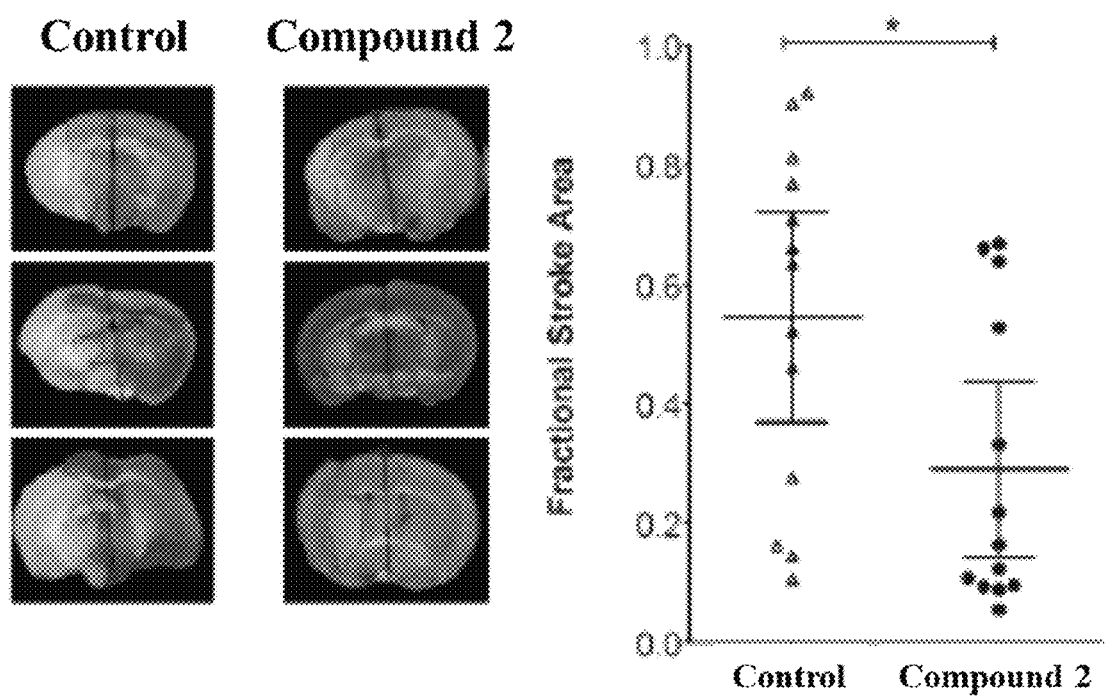
FIG. 11 illustrates representative images from 2,3,5-triphenyltetrazolium chloride (TTC) staining after transient MCAO in CD1 mice.
Figure 12:
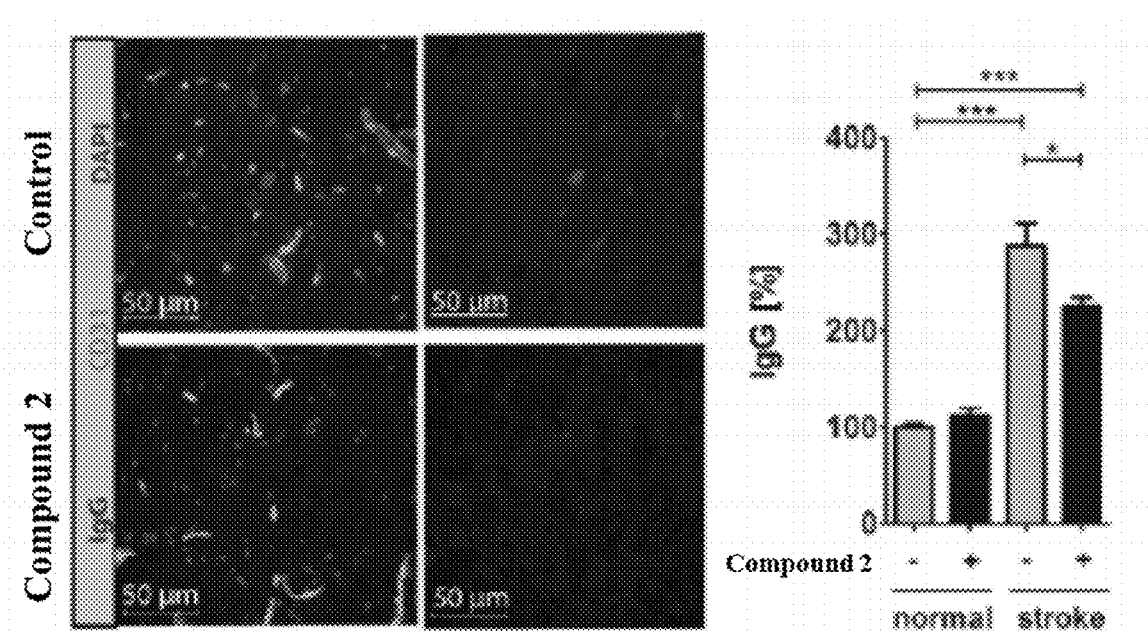
FIG. 12 illustrates the IgG staining in mice treated with a Tie-2 activator as compared to control.
Figure 19:
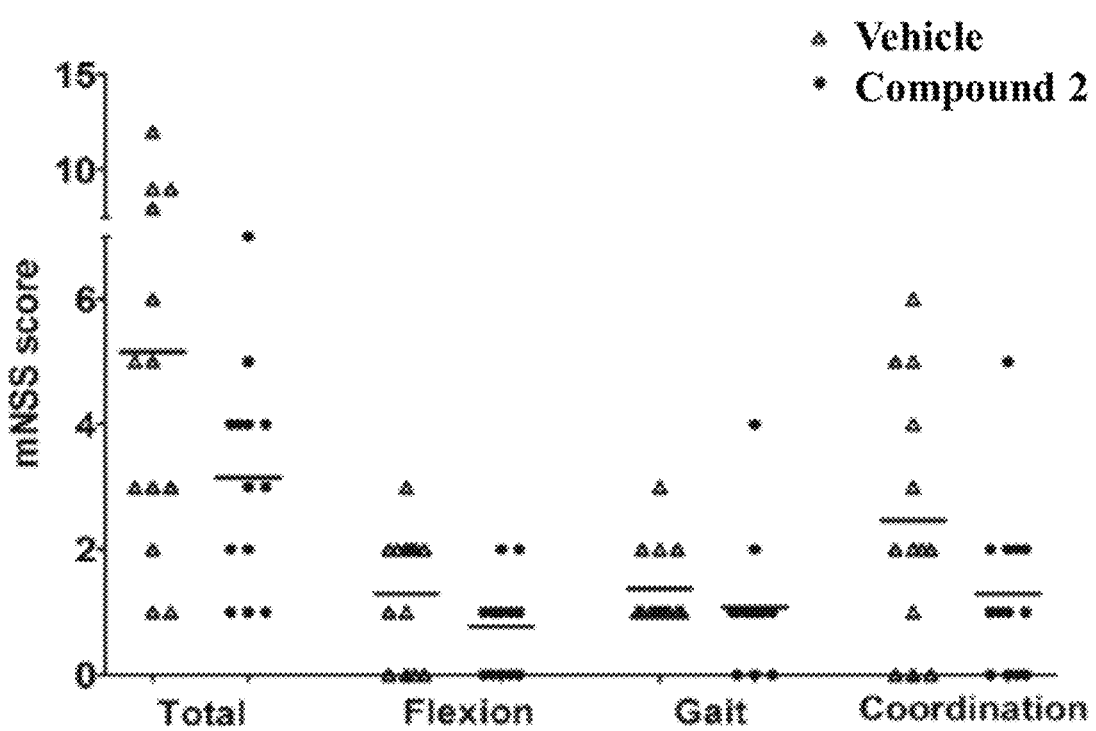
FIG. 19 illustrates a behavior scoring test of control mice and mice treated with a Tie-2 activator.

WT mice displayed significantly decreased stroke sizes as demonstrated via TTC staining compared to control groups that were treated with vehicle dH$_2$O (FIG. 11). Decreased permeability to IgG was also observed in Tie-2 activator treated mice (FIG. 11). An improvement in neurological behavior was observed after stroke (FIG. 19).

Figure 13:
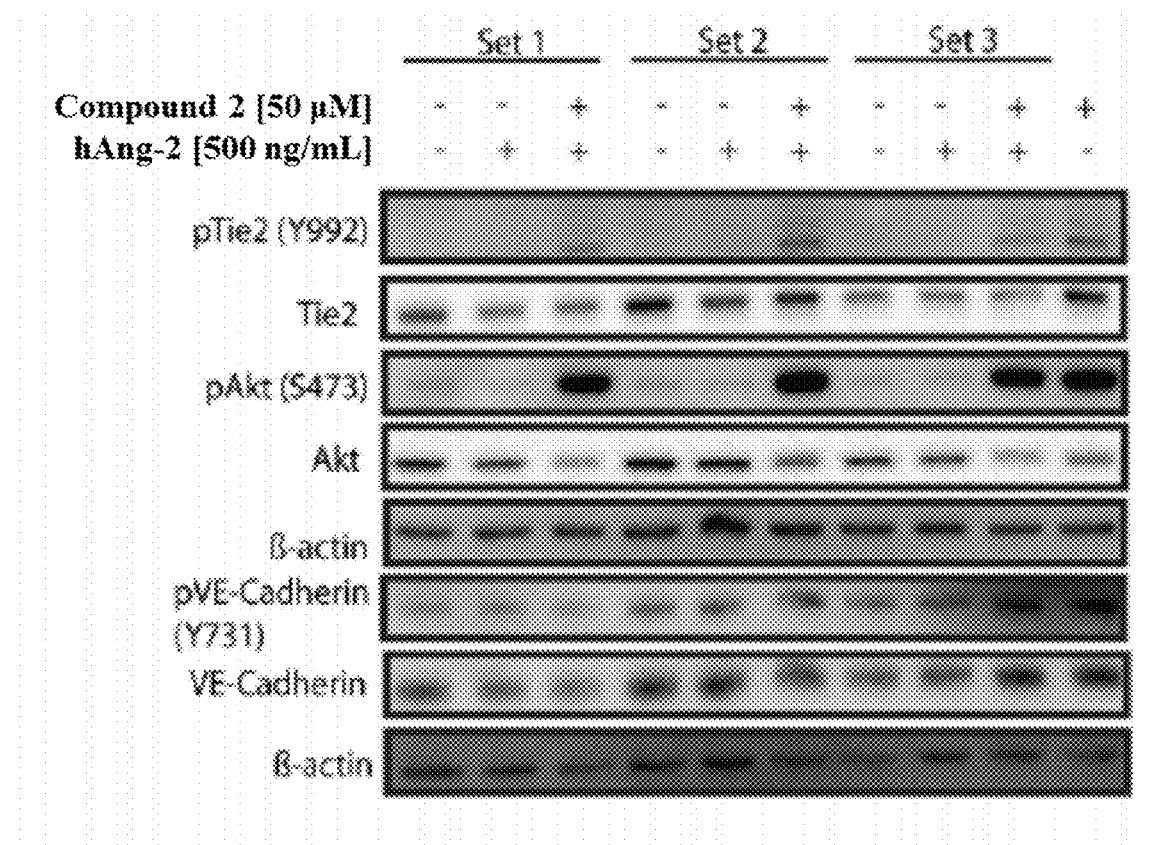
FIG. 13 illustrates Western blot analysis of primary MBMECs pretreated with hAng-2.
Figure 14:
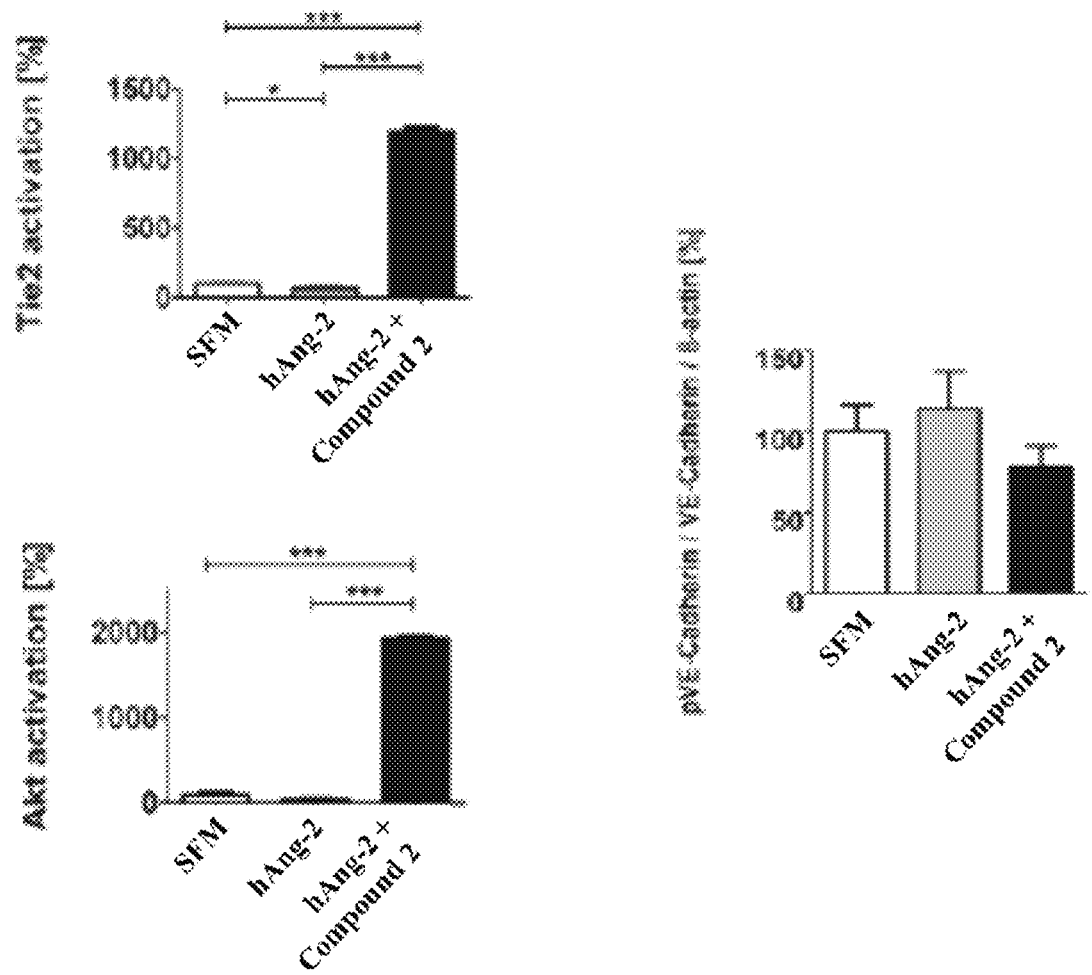
FIG. 14 illustrates graphs quantifying Akt activation, Tie-2 activation, and pVE-cadherin/VE-cadherin levels of primary MBMECs pretreated with hAng-2.

Western Blot analysis of MBMECs pre-treated with hAng-2 (16 h) followed by administration of the Tie-2 activator (10 min) showed an activation of Tie-2 as indicated by the increased levels of pTie-2 and pAkt. Activation of Tie-2/Akt by the Tie-2 activator alone indicates a direct and specific effect of this drug. Phosphorylation of VE-Cadherin responsible for increased junctional permeability was reduced upon treatment with the Tie-2 activator (FIGS. 13 and 14). This observation explains in part the decreased permeability and stroke size in vivo. MBMECs (3 sets) pretreated with hAng-2 (16 h, 500 ng/ml) demonstrated increased Tie-2 and Akt activation upon treatment with the Tie-2 activator (50 µM, 10 min), whereas pVE-Cadherin was decreased in tendency, but not significant (n=3 with 4-6 mice in each set; 2-tailed unpaired t-test).

Figure 15:
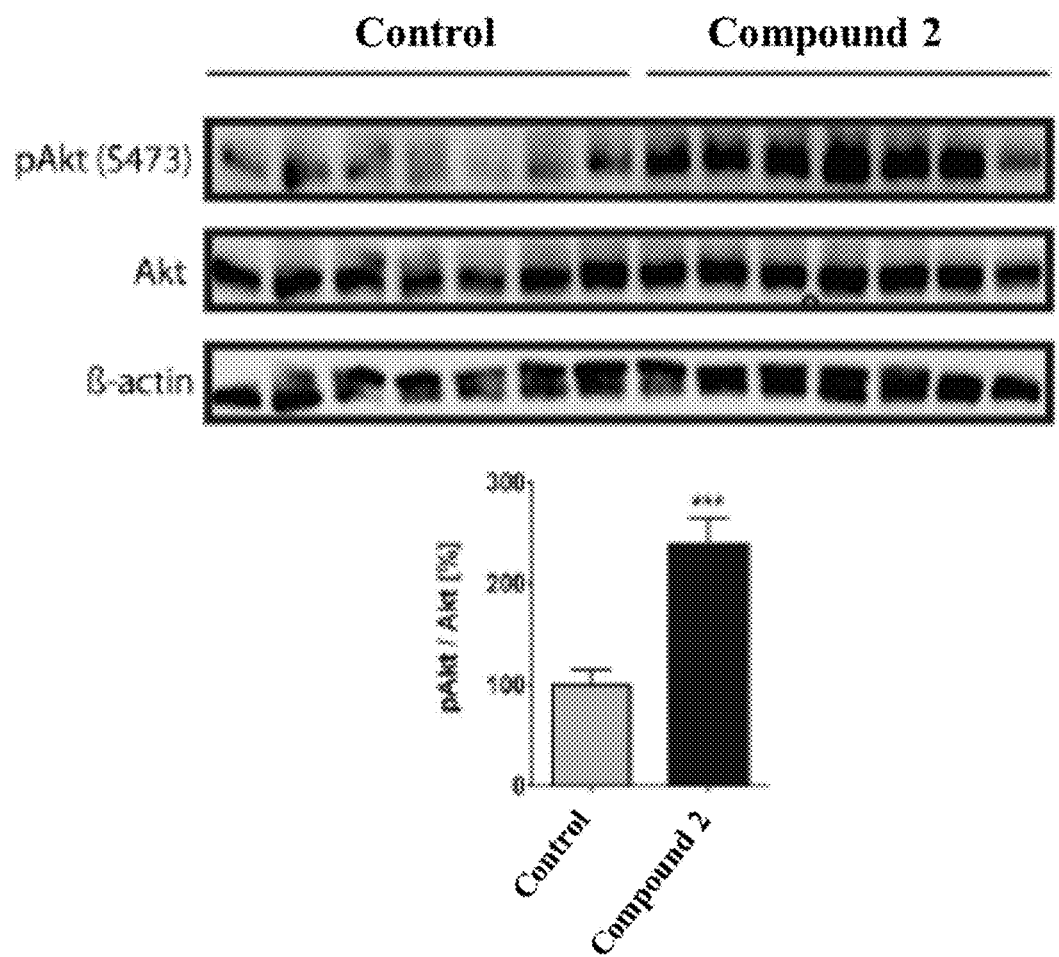
FIG. 15 illustrates Western blot analysis of control brain samples and brain samples treated with a Tie-2 activator.
Figure 16:
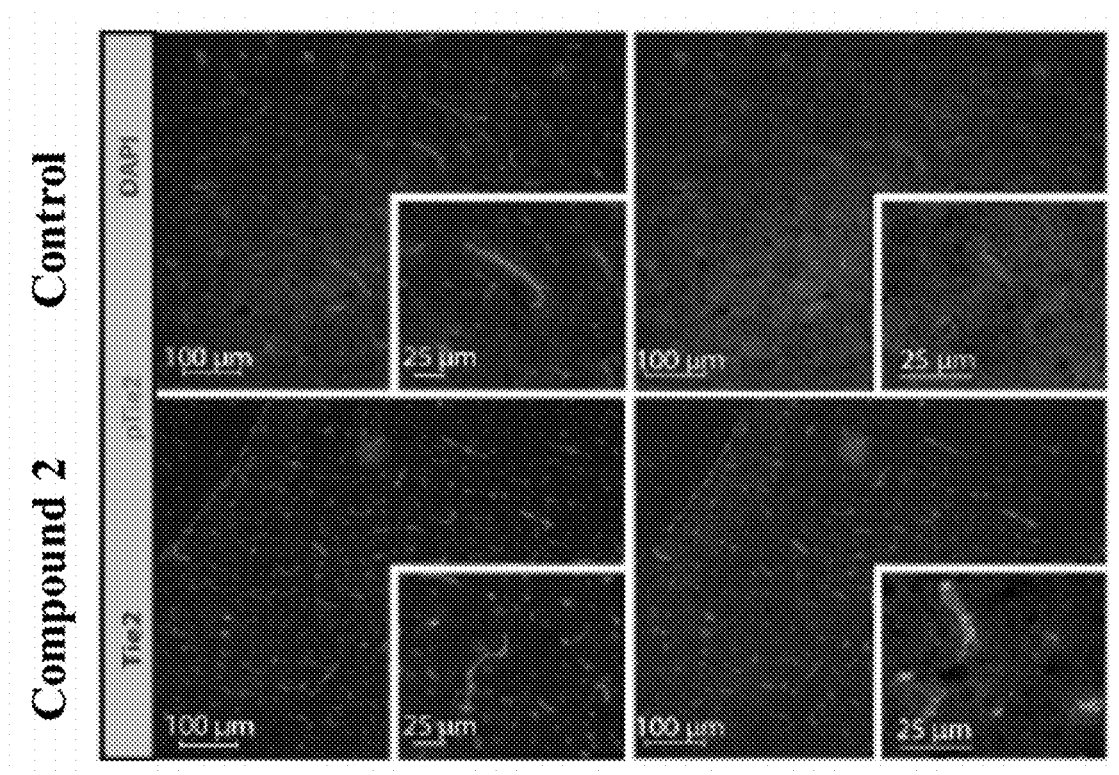
FIG. 16 illustrates representative images of Tie-2 (red) and pTie-2 (green) staining of the stroke hemisphere.

Activation of Tie-2 upon treatment indicated by higher pTie-2 and pAkt levels in stroke hemispheres confirms in vivo activity (FIG. 15). FIG. 15 shows a Western blot analysis of control and Tie-2 activator-treated brain samples from the stroke hemisphere. The result suggests increased Akt activation upon Tie-2 activator treatment (n=7; 2-tailed unpaired t-test). FIG. 16 illustrates representative images (n=2 each group) of Tie-2 (red) and pTie-2 (green) staining of the stroke hemisphere. The result demonstrates increased pTie-2 staining in Tie-2 activator-treated animals compared to controls, and confirms the Western blot data for drug action in vivo.

Example 8

Baseline Safety and Efficacy Study of Combination Therapy for Cancer in a Human Subject with an Oncolytic Virus and a Tie-2 Activator Purpose: to evaluate the outcome of treating human subjects with renal cell carcinoma, lung cancer, melanoma, and advanced metastatic solid tumors with compound 1 and a HSV OV comprising a GM-CSF transgene.

Rationale: administration of a combination treatment of the disclosure can enhance the immunologic responses of renal, lung, skin, and solid tumor cells infected with an HSV OV with a GM-CSF transgene.

Methods: a study is designed with the following experimental arms. 1) experimental arm 1: a dose of a sodium salt of compound 1, 15 mg b.i.d. (total daily dosage of 30 mg/day), in a reconstitution solution comprising HPβ-CD, is administered as a monotherapy to a first group of subjects for 3 months. 2) experimental arm 2: a dose of 100 microliters (µL) comprising $10^{11}$ vector genomes of an HSV OV comprising a GM-CSF transgene is administered intravenously or intratumorally. 3) experimental arm 3: the treatments described in experimental arms 1) and 2) are co-administered either concurrently or sequentially. 4) control arm 4: a first placebo comprised of the reconstitution solution used for compound 1 is administered twice a day for 3 months as a sham monotherapy.

To evaluate safety of the HSV OV, levels of GM-CSF are measured in the subject's tears, blood, saliva, and urine samples at regular intervals post-injection, on Day 0 [baseline], Day 15, Day 30, Day 60, Day 180, and Day 365, using a GM-CSF specific enzyme-linked immunosorbent assay (ELISA).

The presence of the recombinant vector in the subject's tears, blood, saliva, and urine samples is measured at regular intervals post-injection, on Day 0 [baseline], Day 15, Day 30, Day 60, Day 180, and Day 365, using HSV capsid protein quantitation by ELISA or HSV viral genome quantitation by quantitative polymerase chain reaction (qPCR) or digital PCR.

Clinical response of the tumor is determined by measurement of the tumor volume from renal, lung, skin, and solid tumor cells measured as a prolate spheroid. Student's t test is used to assess the significance of the effects of different treatments against the tumors. A reduction in tumor volume with compound 1 and a HSV OV comprising a GM-CSF transgene is used to measure the outcome of treating human subjects with monotherapies versus a combination therapy.

Clinical response is further measured using computed tomography scanning, magnetic resonance imaging, or positron emission tomography (PET), with 18F-fluorodeoxyglucose (18FDG-PET) to determine tumor size and the rate of death of tumors. A reduction in tumor volume with compound 1 and a HSV OV comprising a GM-CSF transgene is used to measure the outcome of treating human subjects with monotherapies versus a combination therapy. Sequential rounds of imaging are performed to determine the durability of clinical response, time to relapse, and sensitivity to additional rounds of therapy.

The imaging-based clinical response can be further determined as the combination of assessments of index and non-index lesions using the following modified WHO criteria: a) complete response is a complete disappearance of all lesions; b) partial response is a decrease relative to baseline of 50% or greater in the sum of the products of the two largest perpendicular diameters of all index lesions, in the absence of complete response; c) stable disease does not meet criteria for complete or partial response, in the absence of progressive disease, or a decrease or tumor stabilization of one or more non-index lesions; d) progressive disease is at least 25% increase in the sum of the products of all index lesions (taking as reference the smallest sum recorded at or following baseline) or the appearance of any new lesion, or progression of a non-index lesion.

Clinical response is further measured by biopsy of the lesion before, during, or after therapy to determine the extent of an immune infiltrate. The biopsy is collected and the number of immune infiltrating cells, for example, cytotoxic T cells, NK cells, type 1 and type 2 macrophages, $T_{regs}$, and myeloid derived suppressor cells, is quantified. A post-treatment increase in cytotoxic T cells, NK cells, or type 1 macrophages, or a decrease in type 2 macrophages, $T_{regs}$, or myeloid derived suppressor cells, indicates that an anti-tumor immune response has initiated. Sequential rounds of immune infiltrate analysis are performed to determine the durability of clinical response, time to relapse, and sensitivity to additional rounds of therapy.

Clinical response is further measured by assessment of circulating tumor DNA (ctDNA) in plasma before, during, or after therapy. An increase in ctDNA during therapy, followed by a decrease after therapy, indicates tumor cell killing in response to therapy. Sequential rounds of ctDNA assessment are performed to determine the durability of clinical response, time to relapse, and sensitivity to additional rounds of therapy.

The overall tumor response is measured based on overall survival of human subjects. Overall survival is obtained with a delayed separation Kaplan-Meier survival curve over a period of at least 6 months.

Example 9

Baseline Safety and Efficacy Study of Combination Therapy for Glioma or Glioblastoma Multiforme (GBM) in a Human Subject with an Oncolytic Virus and a Tie-2 Activator Purpose: to evaluate the outcome of treating human subjects with glioma or GBM with compound 1 and a poliovirus/human rhinovirus type 2 (P/hRT2) hybrid OV.

Rationale: administration of a combination treatment of the disclosure can mitigate the brain tumor related edema (BTRE) associated with morbidity and mortality in human subjects diagnosed with glioma or GBM. Poliovirus is the selected OV due to the high expression of the poliovirus receptor, CD155, on gliomas and GBMs.

Methods: a study is designed with the following experimental arms. 1) experimental arm 1: a dose of a sodium salt of compound 1, 15 mg b.i.d. (total daily dosage of 30 mg/day), in a reconstitution solution comprising HPβ-CD, is administered as a monotherapy to a first group of subjects for 3 months. 2) experimental arm 2: a dose of 100 microliters (μL) comprising $10^{11}$ vector genomes of a P/hRT2 hybrid OV is administered stereotactically, intracranially, or intratumorally. 3) experimental arm 3: the treatments described in experimental arms 1) and 2) are co-administered either concurrently or sequentially. 4) control arm 4: a first placebo comprised of the reconstitution solution used for compound 1 is administered twice a day for 3 months as a sham monotherapy.

The presence of the hybrid OV in the subject's tears, blood, saliva, and urine samples is measured at regular intervals post-injection, for example, on Day 0 [baseline], Day 15, Day 30, Day 60, Day 180, and Day 365, using poliovirus capsid protein quantitation by ELISA or poliovirus viral genome quantitation by quantitative reverse transcription polymerase chain reaction (qRT-PCR) or digital PCR.

Clinical response of the tumor is determined by measurement of the tumor volume from glioma or GBM cells measured as a prolate spheroid. Student's t test is used to assess the significance of the effects of different treatments against the tumors. A reduction in tumor volume with compound 1 and a poliovirus/human rhinovirus type 2 (P/hRT2) hybrid OV is used to measure the outcome of treating human subjects with monotherapies versus a combination therapy.

Clinical response is further measured using computed tomography scanning, magnetic resonance imaging, or positron emission tomography (PET), with MRI contrast agents like gadolinium being used to examine BTRE, as GBM-mediated BTRE allows for specific delivery of gadolinium to the brain upon administration to the subject. Such contrasted MRI is used to determine both tumor size and the vascular permeability of the glioma or GBM. A reduction in tumor volume with compound 1 and a poliovirus/human rhinovirus type 2 (P/hRT2) hybrid OV is used to measure the outcome of treating human subjects with monotherapies versus a combination therapy. Sequential rounds of imaging are used to determine the durability of clinical response, time to relapse, and sensitivity to additional rounds of therapy.

The imaging-based clinical response can be further determined as the combination of assessments of index and non-index lesions using the following modified WHO criteria: a) complete response is a complete disappearance of all lesions; b) partial response is a decrease relative to baseline of 50% or greater in the sum of the products of the two largest perpendicular diameters of all index lesions, in the absence of complete response; c) stable disease does not meet criteria for complete or partial response, in the absence of progressive disease, or a decrease or tumor stabilization of one or more non-index lesions; d) progressive disease is at least 25% increase in the sum of the products of all index lesions (taking as reference the smallest sum recorded at or following baseline) or the appearance of any new lesion, or progression of a non-index lesion.

Clinical response is further measured by biopsy of the lesion before, during, or after therapy to determine the extent of an immune infiltrate. The biopsy is collected and the number of immune infiltrating cells, for example, cytotoxic T cells, NK cells, type 1 and type 2 macrophages, $T_{regs}$, and myeloid derived suppressor cells, is quantified. A post-treatment increase in cytotoxic T cells, NK cells, or type 1 macrophages, or a decrease in type 2 macrophages, $T_{regs}$, or myeloid derived suppressor cells, indicates that an anti-tumor immune response has initiated. Sequential rounds of immune infiltrate analysis are performed to determine the durability of clinical response, time to relapse, and sensitivity to additional rounds of therapy.

The overall tumor response is measured based on overall survival of human subjects. Overall survival is obtained with a delayed separation Kaplan-Meier survival curve over a period of at least 6 months.

Embodiments

The following non-limiting embodiments provide illustrative examples of the invention, do not limit the scope of the invention.

Embodiment 1

A method of treating cancer, the method comprising administering to a subject in need thereof: a) a therapeutically-effective amount of a Tie-2 activator; and b) a therapeutically-effective amount of a modulator of an immune checkpoint molecule.

Embodiment 2

The method of Embodiment 1, wherein the Tie-2 activator binds a phosphatase.

Embodiment 3

The method of any one of Embodiments 1 and 2, wherein the Tie-2 activator inhibits a phosphatase.

Embodiment 4

The method of any one of Embodiments 1-3, wherein the Tie-2 activator binds HPTPβ.

Embodiment 5

The method of any one of Embodiments 1-4, wherein the Tie-2 activator inhibits HPTPβ.

Embodiment 6

The method of any one of Embodiments 1-5, wherein the Tie-2 activator is:

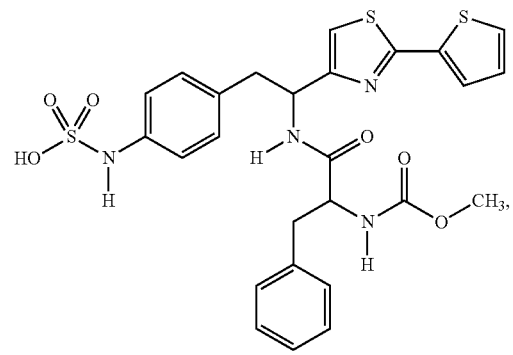 [SMILES: COC(=O)NC(Cc1ccccc1)C(=O)NC(Cc1ccc(NS(=O)(=O)O)cc1)c1csc(-c2cccs2)n1]

or a pharmaceutically-acceptable salt thereof.

Embodiment 7

The method of any one of Embodiments 1-6, wherein the immune checkpoint molecule is LAG3.

Embodiment 8

The method of any one of Embodiments 1-6, wherein the immune checkpoint molecule is BTLA.

Embodiment 9

The method of any one of Embodiments 1-6, wherein the immune checkpoint molecule is KIR.

Embodiment 10

The method of any one of Embodiments 1-6, wherein the immune checkpoint molecule is CTLA4.

Embodiment 11

The method of any one of Embodiments 1-6, wherein the immune checkpoint molecule is ICOS.

Embodiment 12

The method of any one of Embodiments 1-6, wherein the immune checkpoint molecule is TIM3.

Embodiment 13

The method of any one of Embodiments 1-6, wherein the immune checkpoint molecule is A2aR.

Embodiment 14

The method of any one of Embodiments 1-6, wherein the immune checkpoint molecule is PD-1.

Embodiment 15

The method of any one of Embodiments 1-14, wherein the modulator of the immune checkpoint molecule is ipilimumab.

Embodiment 16

The method of any one of Embodiments 1-14, wherein the modulator of the immune checkpoint molecule is nivolumab.

Embodiment 17

The method of any one of Embodiments 1-14, wherein the modulator of the immune checkpoint molecule is tremelimumab.

Embodiment 18

The method of any one of Embodiments 1-14, wherein the modulator of the immune checkpoint molecule is A-dmDT390-bisFv(UCHT1).

Embodiment 19

The method of any one of Embodiments 1-18, wherein the therapeutically-effective amount of the Tie-2 activator is from about 1 mg to about 100 mg.

Embodiment 20

The method of any one of Embodiments 1-18, wherein the therapeutically-effective amount of the Tie-2 activator is about 60 mg.

Embodiment 21

The method of any one of Embodiments 1-20, wherein the Tie-2 activator and the modulator of the immune checkpoint molecule are administered in the same unit dosage form.

Embodiment 22

The method of any one of Embodiments 1-21, wherein the subject is human.

Embodiment 23

A pharmaceutical composition comprising: a) a Tie-2 activator; and b) a modulator of an immune checkpoint molecule, wherein the Tie-2 activator and the modulator of the immune checkpoint molecule are in the same unit dosage form.

Embodiment 24

The pharmaceutical composition of Embodiment 23, wherein the Tie-2 activator binds a phosphatase.

Embodiment 25

The pharmaceutical composition of any one of Embodiments 23 and 24, wherein the Tie-2 activator inhibits a phosphatase.

Embodiment 26

The pharmaceutical composition of any one of Embodiments 23-25, wherein the Tie-2 activator binds HPTPβ.

Embodiment 27

The pharmaceutical composition of any one of Embodiments 23-26, wherein the Tie-2 activator inhibits HPTPβ.

Embodiment 28

The pharmaceutical composition of any one of Embodiments 23-27, wherein the Tie-2 activator is:

or a pharmaceutically-acceptable salt thereof.

Embodiment 29

The pharmaceutical composition of any one of Embodiments 23-28, wherein the immune checkpoint molecule is LAG3.

Embodiment 30

The pharmaceutical composition of any one of Embodiments 23-28, wherein the immune checkpoint molecule is BTLA.

Embodiment 31

The pharmaceutical composition of any one of Embodiments 23-28, wherein the immune checkpoint molecule is KIR.

Embodiment 32

The pharmaceutical composition of any one of Embodiments 23-28, wherein the immune checkpoint molecule is CTLA4.

Embodiment 33

The pharmaceutical composition of any one of Embodiments 23-28, wherein the immune checkpoint molecule is ICOS.

Embodiment 34

The pharmaceutical composition of any one of Embodiments 23-28, wherein the immune checkpoint molecule is TIM3.

Embodiment 35

The pharmaceutical composition of any one of Embodiments 23-28, wherein the immune checkpoint molecule is A2aR.

Embodiment 36

The pharmaceutical composition of any one of Embodiments 23-28, wherein the immune checkpoint molecule is PD-1.

Embodiment 37

The pharmaceutical composition of any one of Embodiments 23-36, wherein the modulator of the immune checkpoint molecule is ipilimumab.

Embodiment 38

The pharmaceutical composition of any one of Embodiments 23-36, wherein the modulator of the immune checkpoint molecule is nivolumab.

Embodiment 39

The pharmaceutical composition of any one of Embodiments 23-36, wherein the modulator of the immune checkpoint molecule is tremelimumab.

Embodiment 40

The pharmaceutical composition of any one of Embodiments 23-36, wherein the modulator of the immune checkpoint molecule is A-dmDT390-bisFv(UCHT1).

Embodiment 41

A method of killing a cancer cell in a human, the method comprising administering to the human an amount of a Tie-2 activator that is effective to kill the cancer cell, wherein the cancer cell is killed in the human by the Tie-2 activator.

Embodiment 42

The method of Embodiment 41, further comprising administering to the human a therapeutically-effective amount of a modulator of an immune checkpoint molecule.

Embodiment 43

The method of any one of Embodiments 41 and 42, wherein the amount of the Tie-2 activator that is effective to kill the cancer cell is from about 1 mg to about 100 mg.

Embodiment 44

The method of any one of Embodiments 41-43, wherein the amount of the Tie-2 activator that is effective to kill the cancer cell is about 30 mg.

Embodiment 45

The method of any one of Embodiments 41-44, wherein the Tie-2 activator binds a phosphatase.

Embodiment 46

The method of any one of Embodiments 41-45, wherein the Tie-2 activator inhibits a phosphatase.

Embodiment 47

The method of any one of Embodiments 41-46, wherein the Tie-2 activator binds HPTPβ.

Embodiment 48

The method of any one of Embodiments 41-47, wherein the Tie-2 activator inhibits HPTPβ.

Embodiment 49

The method of any one of Embodiments 41-48, wherein the Tie-2 activator is:

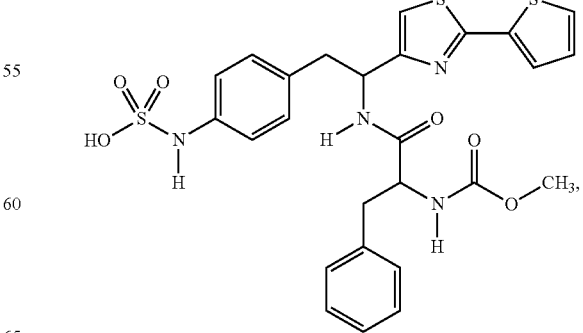

or a pharmaceutically-acceptable salt thereof.

Embodiment 50

The method of any one of Embodiments 41-49, further comprising administering to the human a therapeutically-effective amount of an immunotherapy that acts upstream of IL-2.

What is claimed is:

1. A method of treating cancer, the method comprising administering to a subject in need thereof:
   a) a therapeutically-effective amount of a Tie-2 activator; and
   b) a therapeutically-effective amount of a modulator of an immune checkpoint molecule.
2. The method of claim 1, wherein the Tie-2 activator binds a phosphatase.
3. The method of claim 1, wherein the Tie-2 activator inhibits a phosphatase.
4. The method of claim 1, wherein the Tie-2 activator binds HPTPβ.
5. The method of claim 1, wherein the Tie-2 activator inhibits HPTPβ.
6. The method of claim 1, wherein the Tie-2 activator is:

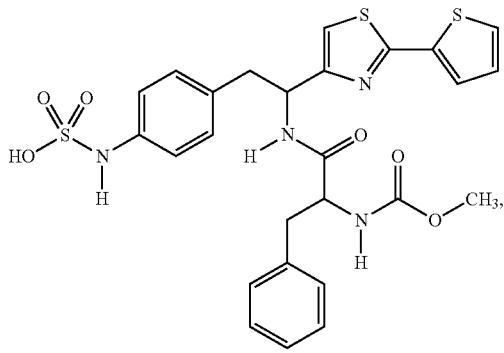 [SMILES: COC(=O)NC(Cc1ccccc1)C(=O)NC(Cc1ccc(NS(=O)(=O)O)cc1)c1csc(-c2cccs2)n1]

or a pharmaceutically-acceptable salt thereof.

7. The method of claim 1, wherein the immune checkpoint molecule is LAGS.
8. The method of claim 1, wherein the immune checkpoint molecule is BTLA.
9. The method of claim 1, wherein the immune checkpoint molecule is KIR.
10. The method of claim 1, wherein the immune checkpoint molecule is CTLA4.
11. The method of claim 1, wherein the immune checkpoint molecule is ICOS.
12. The method of claim 1, wherein the immune checkpoint molecule is TIM3.
13. The method of claim 1, wherein the immune checkpoint molecule is A2aR.
14. The method of claim 1, wherein the immune checkpoint molecule is PD-1.
15. The method of claim 1, wherein the modulator of the immune checkpoint molecule is ipilimumab.
16. The method of claim 1, wherein the modulator of the immune checkpoint molecule is nivolumab.
17. The method of claim 1, wherein the modulator of the immune checkpoint molecule is tremelimumab.
18. The method of claim 1, wherein the modulator of the immune checkpoint molecule is A-dmDT390-bisFv (UCHT1).
19. The method of claim 1, wherein the therapeutically-effective amount of the Tie-2 activator is from about 1 mg to about 100 mg.
20. The method of claim 1, wherein the therapeutically-effective amount of the Tie-2 activator is about 15 mg.
21. The method of claim 1, wherein the Tie-2 activator and the modulator of the immune checkpoint molecule are administered in the same unit dosage form.
22. The method of claim 1, wherein the subject is human.
23. A pharmaceutical composition comprising:
   a) a Tie-2 activator; and
   b) a modulator of an immune checkpoint molecule, wherein the Tie-2 activator and the modulator of the immune checkpoint molecule are in the same unit dosage form.
24. The pharmaceutical composition of claim 23, wherein the Tie-2 activator binds a phosphatase.
25. The pharmaceutical composition of claim 23, wherein the Tie-2 activator inhibits a phosphatase.
26. The pharmaceutical composition of claim 23, wherein the Tie-2 activator binds HPTPβ.
27. The pharmaceutical composition of claim 23, wherein the Tie-2 activator inhibits HPTPβ.
28. The pharmaceutical composition of claim 23, wherein the Tie-2 activator is:

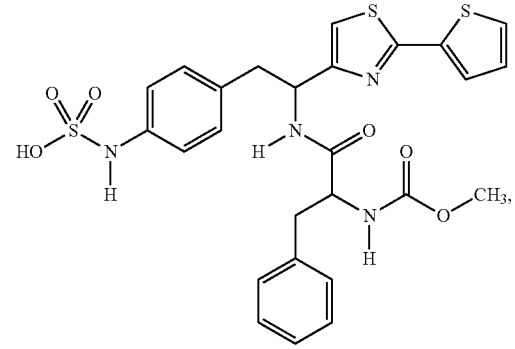 [SMILES: COC(=O)NC(Cc1ccccc1)C(=O)NC(Cc1ccc(NS(=O)(=O)O)cc1)c1csc(-c2cccs2)n1]

or a pharmaceutically-acceptable salt thereof.

29. The pharmaceutical composition of claim 23, wherein the immune checkpoint molecule is LAG3.
30. The pharmaceutical composition of claim 23, wherein the immune checkpoint molecule is BTLA.
31. The pharmaceutical composition of claim 23, wherein the immune checkpoint molecule is KIR.
32. The pharmaceutical composition of claim 23, wherein the immune checkpoint molecule is CTLA4.
33. The pharmaceutical composition of claim 23, wherein the immune checkpoint molecule is ICOS.
34. The pharmaceutical composition of claim 23, wherein the immune checkpoint molecule is TIM3.
35. The pharmaceutical composition of claim 23, wherein the immune checkpoint molecule is A2aR.
36. The pharmaceutical composition of claim 23, wherein the immune checkpoint molecule is PD-1.
37. The pharmaceutical composition of claim 23, wherein the modulator of the immune checkpoint molecule is ipilimumab.
38. The pharmaceutical composition of claim 23, wherein the modulator of the immune checkpoint molecule is nivolumab.
39. The pharmaceutical composition of claim 23, wherein the modulator of the immune checkpoint molecule is tremelimumab.

40. The pharmaceutical composition of claim 23, wherein the modulator of the immune checkpoint molecule is A-dmDT390-bisFv(UCHT1).

* * * * *

UNITED STATES PATENT AND TRADEMARK OFFICE
CERTIFICATE OF CORRECTION

PATENT NO. : 9,539,245 B2  
APPLICATION NO. : 14/819871  
DATED : January 10, 2017  
INVENTOR(S) : Kevin Peters Page 1 of 1

It is certified that error appears in the above-identified patent and that said Letters Patent is hereby corrected as shown below:

In the Claims

In Claim 7, Column 61, Line 44, please replace -LAGS- with --LAG3--.

Signed and Sealed this  
Eighth Day of August, 2017

Joseph Matal  
*Performing the Functions and Duties of the*  
*Under Secretary of Commerce for Intellectual Property and*  
*Director of the United States Patent and Trademark Office*